(12) United States Patent
Ulitin et al.

(10) Patent No.: US 11,447,574 B2
(45) Date of Patent: Sep. 20, 2022

(54) METHOD FOR TREATMENT OF AN IL-17A-MEDIATED DISEASE THROUGH ANTIBODY ADMINISTRATION SPECIFIC TO HUMAN IL-17A

(71) Applicant: JOINT STOCK COMPANY "BIOCAD", Saint Petersburg (RU)

(72) Inventors: Andrey Borisovich Ulitin, Puschino (RU); Stanislav Rudolfovich Evdokimov, Puschino (RU); Valeriy Vladimirovich Soloviev, Puschino (RU); Yulia Sergeevna Chernykh, Solikamsk (RU); Olga Vladimirovna Goncharova, Lyubuchany (RU); Dmitriy Valerievich Korzhavin, St.Petersburg (RU); Tatyana Veniaminovna Chernovskaya, Lyubuchany (RU); Timofey Aleksandrovich Nemankin, St.Petersburg (RU); Roman Alexeevich Ivanov, Moscow (RU); Dmitriy Valentinovich Morozov, Moscow (RU); Victoria Mikhailovna Ekimova, Tyumen (RU); Ekaterina Vladimirovna Sofronova, The Republic of Tatarstan Kazan (RU); Yakov Yurevich Ustyugov, Berezniki Perm obl. (RU)

( * ) Notice: Subject to any disclaimer, the term of this patent is extended or adjusted under 35 U.S.C. 154(b) by 62 days.

(21) Appl. No.: 16/564,148

(22) Filed: Sep. 9, 2019

(65) Prior Publication Data
US 2020/0031952 A1      Jan. 30, 2020

Related U.S. Application Data

(60) Division of application No. 15/254,225, filed on Sep. 1, 2016, now Pat. No. 10,442,869, which is a continuation of application No. PCT/RU2015/000163, filed on Mar. 23, 2015.

(30) Foreign Application Priority Data

Sep. 26, 2014 (RU) .......................... RU2014138740

(51) Int. Cl.
| | |
|---|---|
| *A61K 39/395* | (2006.01) |
| *C07K 16/46* | (2006.01) |
| *A61K 45/06* | (2006.01) |
| *C07K 16/24* | (2006.01) |

(52) U.S. Cl.
CPC ........ *C07K 16/461* (2013.01); *A61K 39/3955* (2013.01); *A61K 39/39591* (2013.01); *A61K 45/06* (2013.01); *C07K 16/244* (2013.01); *C07K 2317/22* (2013.01); *C07K 2317/24* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01)

(58) Field of Classification Search
CPC .......................... C07K 16/461; C07K 16/244; C07K 2317/56; A61K 39/3955
See application file for complete search history.

(56) References Cited

U.S. PATENT DOCUMENTS

| | | |
|---|---|---|
| 2011/0053865 A1 | 3/2011 | Saunders et al. |
| 2012/0225065 A1 | 9/2012 | Jaspers et al. |
| 2014/0205613 A1 | 7/2014 | Voss et al. |

FOREIGN PATENT DOCUMENTS

| | | |
|---|---|---|
| RU | 2426741 C2 | 8/2011 |
| WO | 2012156219 A1 | 11/2012 |

OTHER PUBLICATIONS

Matsuzaki et al. Interleukin-17 as an Effector Molecule of Innate and Acquired Immunity against Infections. MicrobiolImmunol., 2007;51(12):1139-47.*
Benchetritetal. Interleukin-17 inhibits tumor cell growth by means of a T-cell-dependent mechanism. Blood, Mar. 15, 2002, vol. 99, No. 6, pp. 2114-2121.*
Wrdbel et al. Interleukin-17 in acute myeloid leukemia. J Cell Mol Med., Oct.-Dec. 2003;7(4):472-4.*
Fan et al. The prevalence of Th17 cells in patients with acute myeloid leukemia.Zhonghua Xue Ye Xue Za Zhi. Sep. 2010; 31(9):617-620 (abstrac).*
International application No. PCT/RU2015/000163 search report with English translation dated Oct. 22, 2015.
International application No. PCT/RU2015/000163 written opinion with English translation dated Oct. 22, 2015.
International application No. PCT/RU2015/000163 IPRP1 dated Oct. 22, 2015.
European application No. 15843607 extended search report and opinion dated Aug. 24, 2018.
Japanese application No. 2016-555526 office action with English translation dated Mar. 11, 2019.
Japanese application No. 2016-555526 office action with English translation dated Aug. 15, 2019.
Japanese application No. 2016-555526 office action with English translation dated Jan. 8, 2020.
Canadian application No. 2941656 office action dated Jul. 25, 2017.
Canadian application No. 2941656 office action dated Jun. 15, 2018.
Canadian application No. 2941656 office action dated Jul. 3, 2019.
U.S. Appl. No. 15/254,225 office action dated Apr. 18, 2018.
U.S. Appl. No. 15/254,225 office action dated Dec. 27, 2018.
Porter, "Structural Studies of Immunoglobulins", Science, May 18, 1973, vol. 180, pp. 713-716.

(Continued)

*Primary Examiner* — Dong Jiang
(74) *Attorney, Agent, or Firm* — Anglehart et al.

(57) ABSTRACT

The monoclonal IgG-type antibodies were suggested comprising variable domains represented by a combination of VHH-derivative with a variable domain of the light chain $V_L$. Said antibodies can comprise amino acid substitutions at positions 44 and 45 (Kabat numbering) or combinations thereof. Antibodies of the invention possess increased affinity and improved aggregation stability.

18 Claims, 24 Drawing Sheets

Specification includes a Sequence Listing.

(56) References Cited

OTHER PUBLICATIONS

Padlan, "Review, Anatomy of the Antibody Molecule", Molecular Immunology, 1994, vol. 31, No. 3, pp. 169-217.
Burton, "Review, Immunoglobulin G: Functional Sites", Molecular Immunology, 1985, vol. 22, No. 3, pp. 161-206.
Hamers-Casterman et al., "Naturally Occurring Antibodies Devoid of Light Chains", Nature, Jun. 3, 1993, vol. 363, pp. 446-448.
Tillib, ""Camel Nanoantibody" is an Efficient Tool for Research, Diagnostics and Therapy", Molecular Biology, 2011, vol. 45, No. 1, pp. 66-73.
Nguyen et al., "Loss of Splice Consensus Signal is Responsible for the Removal of the Entire CHI Domain of the Functional Camel IGG2A Heavy-Chain Antibodies", Molecular Immunology, 1999, vol. 36, pp. 515-524.
Woolven et al., "The Structure of the llama Heavy Chain Constant Genes Reveals a Mechanism for Heavy-Chain Antibody Formation", Immunogenetics, 1999, vol. 50, pp. 98-101.
Nguyen et al., "Camel Heavy-Chain Antibodies: Diverse Germline VHH and Specific Mechanisms Enlarge the Antigen-Binding Repertoire", The EMBO Journal, 2000, vol. 19, No. 5, pp. 921-930.
De Genst et al., "Antibody Repertoire Development in Camelids", Developmental and Comparative Immunology, 2006, vol. 30, pp. 187-198.
S. Muyldermans et al. Recognition of antigens by single-domain antibody fragments: the superfluous luxury of paired domains, Trends in Biochemical Sciences, 2001, vol. 26, No. 4, pp. 230-235.
De Genst et al., "Molecular Basis for the Preferential Cleft Recognition by Dromedary Heavy Chain Antibodies", PNAS, Mar. 21, 2006, vol. 103, No. 12, pp. 4586-4591.
Nguyen et al., "Functional Heavy-Chain Antibodies in Camelidae", Advances in Immunology, 2001, vol. 79, pp. 261-296.
Dorota Smolarek et al: "Variable fragments of heavy chain antibodies (VHHs): a new magic bullet molecule of medicine?* Zmienne fragmenty przeciwcial ciezkolancuchowych (VHH): nowa magiczna kula medycyny? Full-textPDF: Introduction", Postepy Hig Med Dosw, vol. 66, Apr. 12, 2012 (Apr. 12, 2012), pp. 348-358, XP055454152.
Diana Gil et al: "Strategies to stabilize compact folding and minimize aggregation of antibody-based fragments", Advances in Bioscience and Biotechnology, vol. 4, Jan. 1, 2013 (Jan. 1, 2013), pp. 73-84, XP055325678, ISSN:2156-8456, DOI: 10.4236/abb.2013. 44A011.
Peter Bannas et al: "Nanobodies and Nanobody-Based Human Heavy Chain Antibodies as Antitumor Therapeutics", Frontiers in Immunology, vol. 8, Nov. 22, 2017 (Nov. 22, 2017), XP055454260, CH ISSN: 1664-3224, DOI: 10.3389/fimmu.2017.01603.
De Genst et al., "Strong in Vivo Maturation Compensates for Structurally Restricted H3 Loops in Antibody Repertoires", The Journal of Biological Chemistry, 2005, vol. 280, No. 14, pp. 14114-14121.
Lauwereys et al., "Potent Enzyme Inhibitors Derived from Dromedary Heavy Chain Antibodies", The EMBO Journal, 1998, vol. 17, No. 13, pp. 3512-3520.
Kontermann, "Strategies to Extend Plasma Half-Lives of Recombinant Antibodies", Biodrugs, 2009, vol. 23(2), pp. 93-109.
Coppieters et al., "Formatted Anti-Tumor Necrosis Factor Alpha VHH Proteins Derived from Camelids Show Superior Potency and Targeting to inflamed Joints in a Murine Model of Collagen-Induced Arthritis, Arthritis & Rheumatology, Jun. 6, 2016, vol. 54, No. 6, pp. 1856-1866.
Richard et al., "In Vivo Neutralization of a-Cobratoxin with High-Affinity Llama Single-Domain Antibodies (VhHs) and A VhH-Fc Antibody", PLOS One, Jul. 2013, vol. 8, Issue 7, pp. 1-14.
Andersen et al., "Selection of Nanobodies that Target Human Neonatal Fc Receptor", Scientific Reports, 2012, vol. 3 : 1118, pp. 1-7.
Vincke et al., "General Strategy to Humanize a Camelid Single-Domain Antibody and Identification of a Universal Humanized Nanobody Scaffold", The Journal of Biological Chemistry, 2009, vol. 284, No. 5, pp. 3273-3284.
Barthelemy et al., "Comprehensive Analysis of the Factors Contributing to the Stability and Solubility of Autonomous Human Vh Domains", The Journal of Biological Chemistry, 2008, vol. 283, No. 6, pp. 639-3654.
Conrath et al., "Antigen Binding and Solubility Effects upon the Veneering of a Camel VHH in Framework-2 to Mimic a VH", J. Mol. Biol., 2005, vol. 350, pp. 112-125.
Hermeling et al., "Structure-Immunogenicity Relationships of Therapeutic Proteins", Pharmaceutical Research, Jun. 2004, vol. 21, No. 6, pp. 897-903.
Haard et al., "A Large Non-immunized Human Fab Fragment Phage Library That Permits Rapid Isolation and Kinetic Analysis of High Affinity Antibodies", The Journal of Biological Chemistry, Jun. 25, 1999, vol. 274, No. 26, pp. 18218-18230.
Koch-Nolte et al., "Single Domain Antibodies from llama Effectively and Specifically Block T Cell Ecto-ADP-Ribosyltransferase ART2.2 in vivo", The FASEB Journal, Nov. 2007, vol. 21, pp. 3490-3498.
Sidhu et al., "Phage Display for Selection of Novel Binding Peptides", Methods in Enzymology, 2000, vol. 328, pp. 333-363.
Marks et al., "By-Passing Immunization: Human Antibodies from V-gene Libraries Displayed on Phage", J. Mol. Biol., Dec. 1991, vol. 222, pp. 581-597.
Vaughan et al., "Human Antibodies with Sub-nanomolar Affinities Isolated from a Large Non-immunized Phage Display Library", Nature Biotechnology, Mar. 1996, vol. 14, pp. 309-314.
Tominaga et al., "Determination of Essential and Variable Residues in Pediocin PA-1 by NNK Scanning", Applied and Environmental Microbiology, Feb. 2006, vol. 72, No. 2, pp. 1141-1147.
Votsmeier et al., "Femtomolar Fab Binding Affinities to a Protein Target by Alternative CDR Residue Co-Optimization Strategies without Phage or Cell Surface Display", MABS, 2012, vol. 4, Issue 3, pp. 341-348.
Cummings et al., "Universal Screening Methods and Applications of ThermoFluor", Journal of Biomolecular Screening, 2006, vol. 11(7), pp. 854-863.

* cited by examiner

High-affinity aggregation non-resistant VHH-based antibody

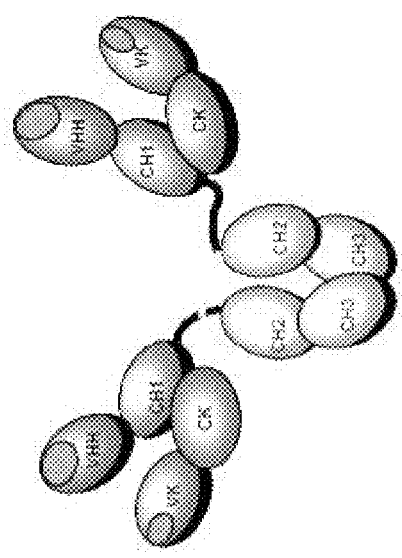

High-affinity aggregation resistant antibody on the basis of mutant VHH

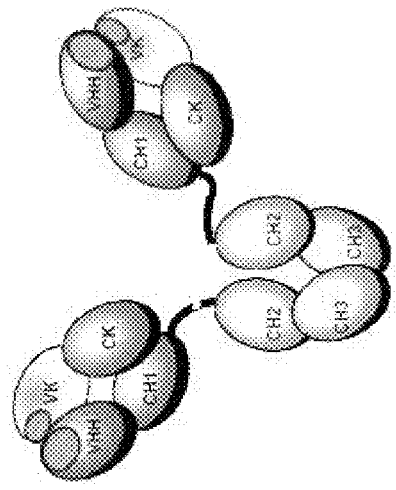

Mutagenesis by VHH position 44+45 plus light chain shuffling

Display libraries and selection under tight conditions (low antigen concentrations, long-term washing, incubation with competitors, increased temperature, etc.). High-performance robotic screening including the testing of affinity and aggregation stability

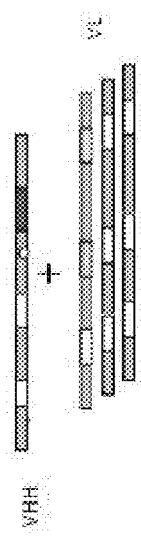

Fig. 1

A - Human recombinant IL17A-His6-FLAG product (15% PAGE+ β-ME).

1) 9E10 0.25 μg+ β-ME
2) 9E10 0.5 μg + β-ME
3) 9E10 1 μg + β-ME
4) ---
5) Enzyme marker unstained
6) Medium before application to IMACBioRad
7) Medium after application to IMACBioRad
8) Washing 1
9) Washing 2
10) Washing 3
11) Elution.5 μL
12) Elution 5 μL
13) Elution 10 μL.

B - VHHIgG1 products with various amino acid substitutions at position 45 of VHH domain (12% PAGE+β-ME).

1) Control IgG1  2.5 µg
2) Control IgG1  5 µg
3) Control IgG1  10 µg
4) -
5) Enzyme PW marker unstained
6) VHHIgG1 aIL17 A45/K8 5 µL
7) VHHIgG1 aIL17 D45/K8 5 µL
8) VHHIgG1 aIL17 F45/K8 5 µL
9) -
10) VHHIgG1 aIL17 G45/K8 cult liq before 5 µL
11) VHHIgG1 aIL17 G45/K8 cult liq after 5 µL
12) VHHIgG1 aIL17 G45/K8 5 µL
13) -
14) VHHIgG1 aIL17 H45/K8 5 µL.
15) VHHIgG1 aIL17 I45/K8 5 µL.

C - Products with various amino acid substitutions at position 45 of VHH domain (8% PAGE, free of β-ME).

1) Control IgG1 2.5 μg
2) Control IgG1 5 μg
3) Control IgG1 10 μg
4) –
5) Enzyme PW marker unstained
6) –
7) VHHIgG1 aIL17 A45/K8 5 μL
8) VHHIgG1 aIL17 D45/K8 5 μL
9) VHHIgG1 aIL17 F45/K8 5 μL
10) –
11) VHHIgG1 aIL17 G45/K8 cult liq before 5 μL
12) –
13) VHHIgG1 aIL17 H45/K8 cult liq after 5 μL
14) –
15) VHHIgG1 aIL17 I45/K8 5 μL

A

1VHH
QVQLQQSGGGSVQTGGSLTLTCAASGLTFEANSLGWFRQSPGKEREFVAAVSFTKRIDYADSVK
GRFFISRDNTMNTVYLQMNSLKPEDTGIYTCAADPLLISNKRANI-----WGQGTMVTVSS

2VHH
QVQLVQSGGGLVQPGGSLRLSCAASPRVISIHDMAWYRQAPGKERELVAGITTRGITDYGYSVK
GRFTISRDDAKNTLFLQMNDLKPEDTAVYYCNLRHYEV------------WGQGTLVTVSS

3VHH
QVQLQQSGGGSVQAGGSLRLSCAASGGTFATSPMGWFRQAPGKEREGVAAISPSGGDRIYDDSV
KGRFTISRDNAGYFIYLQMNSLKPEDTARYYCAVRRRFDGTSYYTGDYDSWGQGTLVTVSS

VK4B11DVVMTQSPSSVTASAGETVTINCKSSQSVAYKSNQKNYLAWYQQRPGQSPRLLIYYAS
TRTSGVPDRFSGSGSTTDFTLTISSFQPEDAAVYYCQQGYSAPYSFGSGTKLEIK

VLB5
AVLTQLSSMSGSPGQTVTITCTGSITNIGQYRVNWYQHLPGTAPKLLIYSNANRVSGVPDRFSG
SKSGSTASLTIAGVQAEDEADYYCSAWDGSLNGYVFGGGTKVTVLQR

VLF4QAVLTQPPSVSGSPGQTVTISCTGTSDDVGSGNYVSWYQQVPGMAPKLLIYNAGTRRAGI
TGRFSASKSGNTASLTISGLQSEDEADYYCASYRKINKYVFGGGTKLTVLQR

Wild 3VHHFab

QVQLQQSGGGSVQAGGSLRLSCAASGGTFATSPMGWLRQAPGK<u>ER</u>EFVAAISPS
GGDRIY<u>D</u>DSVKGRFTISRDNAGYFIYLQMNSLKPEDTARYYCAVRRRFDGTSYY
TGDYDSWGQGTLVTVSS mut1

QVQLQQSGGGSVQAGGSLRLSCAASGGTFATSPMGWLRQAPGK<u>GL</u>EFVAAISPS
GGDRIY<u>A</u>DSVKGRFTISRDNAGYFIYLQMNSLKPEDTARYYCAVRRRFDGTSYY
TGDYDSWGQGTLVTVSS mut2

QVQLQQSGGG<u>L</u>VQAGGSLRLSCAASGGTFATSPMGWLRQAPGK<u>GR</u>E<u>W</u>VAAISP
SGGDRIY<u>A</u>DSVKGRFTISRDNAGYFIYLQMNSLKPEDTARYYCAVRRRFDGTSY
YTGDYDSWGQGTLVTVSS mut3

QVQLQQSGGGSVQAGGSLRLSCAASGGTFATSPMGWLRQAPGKE<u>L</u>EFVAAISPS
GGDRIY<u>A</u>DSVKGRFTISRDNAGYFIYLQMNSLKPEDTARYYCAVRRRFDGTSYY
TGDYDSWGQGTLVTVSS mut4

QVQLQQSGGG<u>L</u>VQAGGSLRLSCAASGGTFATSPMGWLRQAPGK<u>G</u>REFVAAISP
SGGDRIY<u>A</u>DSVKGRFTISRDNAGYFIYLQMNSLKPEDTARYYCAVRRRFDGTSY
YTGDYDSWGQGTLVTVSS

VK1A7
EIVLTQSPASLSASVGDRVDITCQASQSINNKIAWYQQKPGKPPKVLIYAASKLP
TGVPSRFSGSGSGTDFTLTISSLQAEDVATYYCLQDYNWPWTFGAGTKLEIK

VK3c18
EIVLTQSPGTLSLSPGERATLSCRASQSVSSSYLAWYQQKPGQAPRLLIYDASSR
ATGIPDRFSGSGSGTDFTLTISRLEPEDFAVYYCQQYSYSPVTFGQGTKVEIK

VK3c118
EIVLTQSPGTLSLSPGERATLSCRASQSVSSSYLAWYQQKPGQAPRLLIYGASSR
ATGIPDRFSGSGSGTDFTLTISRLEPEDFAVYYCQQSYYYPVTFGQGTKVEIK

VK4E12
DIQLTQSPSSLSASAGETASINCKSSQSVLYSSNNKNYLAWYQQKPGQPPKLLIY
WASTRESGVPDRFSGSGSGTDFTLTISSLQSEDAAVYYCQQGYSTPHTFGQGTKV
EIK

Fig. 16

Gel electrophoresis in 12% PAGE + β-ME

1) IgG1 control, 2.5 µg
2) Ferments unstained marker
3) 44V45T VHHIgG1c8 culture liquid before purification 10 µL
4) 44V45T VHHIgG1c8 culture liquid after purification 10 µL
5) 44V45T VHHIgG1c8 5 µL
6) 44D45T VHHIgG1c8 5 µL
7) 44T45T VHHIgG1c8 5 µL
8) 44A45T VHHIgG1c8 5 µL
9) 44S45T VHHIgG1c8 5 µL
10) 44V45V VHHIgG1c8 5 µL
11) 44D45V VHHIgG1c8 5 µL
12) 44A45V VHHIgG1c8 5 µL
13) 44T45V VHHIgG1c8 5 µL.

Gel electrophoresis in 12% PAGE + β-ME

1) IgG1 control, 2.5 μg
2) IgG1 control, 5 μg
3) IgG1 control, 10 μg
4) Fermentos unstained PW marker
5) 44V45T VHHIgG1c8 5 μL
6) 44D45T VHHIgG1c8 5 μL
7) 44T45T VHHIgG1c8 5 μL
8) 44A45T VHHIgG1c8 5 μL
9) 44S45T VHHIgG1c8 5 μL
10) 44V45V VHHIgG1c8 5 μL
11) 44D45V VHHIgG1c8 5 μL
12) 44A45V VHHIgG1c8 5 μL
13) 44T45V VHHIgG1c8 5 μL.

Dashed thick lines correspond to the combinations providing the maximum balanced aggregation stability and functional activity values; Dashed thin lines correspond to the suitable aggregation stability values with the high affinity remained.

Human anti-IL17ABCD-109 cIL17 Fc

| Conc. (nM) | Response | KD (M) | kon(1/Mc) | konError | kdis(1/c) | kdisError | Full R^2 |
|---|---|---|---|---|---|---|---|
| 68,6 | 1,2363 | <1.0E-12 | 2,00E+05 | 3,28E+03 | <1.0E-07 | | 0,383582 |
| 34,3 | 1,06 | <1.0E-12 | 2,61E+05 | 3,72E+03 | <1.0E-07 | | 0,744563 |
| 17,1 | 0,845 | 4,40E-12 | 2,82E+05 | 6,65E+03 | 1,24E-06 | 2,61E-07 | 0,775434 |

Fig. 23A

Macaque anti-IL17A BCD-109 c IL17 Fc

| Conc. (nM) | Response | KD (M) | kon(1/Mc) | konError | kdis(1/c) | kdisError | Full R^2 |
|---|---|---|---|---|---|---|---|
| 68,7 | 1,3497 | <1.0E-12 | 3,24E+05 | 3,22E+03 | 2,36E-07 | 1,71E-07 | 0,672159 |
| 34,4 | 1,2814 | <1.0E-12 | 4,26E+05 | 8,35E+03 | <1.0E-07 | | 0,061979 |
| 17,2 | 1,127 | <1.0E-12 | 5,71E+05 | 7,48E+03 | <1.0E-07 | | 0,753773 |

Fig. 23B

-------- Chromatographic profile obtained with the antibody before heating

---------- Chromatographic profile obtained with the antibody after heating

Protein concentrations were aligned and equaled 10 mg/mL in PBS

METHOD FOR TREATMENT OF AN IL-17A-MEDIATED DISEASE THROUGH ANTIBODY ADMINISTRATION SPECIFIC TO HUMAN IL-17A

CROSS-REFERENCE

The present application is a divisional patent application of U.S. patent application Ser. No. 15/254,225, now U.S. Pat. No. 10,442,869, that claims convention priority to Russian Utility Patent Application No. 2014138740, filed on Sep. 26, 2014, entitled "ВЫСОКОА ФФИНЫЕ И АГРЕГАЦИОННО СТАБИЛЬНЫЕ АНТИТЕЛА НА ОСНОВЕ ВАРИАБЕЛЬНЫХ ДОМЕНОВ VL И ПРОИЗВОДНОГО VHH". This application is incorporated by reference herein in its entirety. The present application is a continuation of International Patent Application no. PCT/RU2015/000163, filed on Mar. 23, 2015, entitled "HIGH AFFINITY AND AGGREGATIVELY STABLE ANTIBODIES ON THE BASIS OF VARIABLE DOMAINS VL AND A DERIVATIVE VHH". This application is incorporated by reference herein in its entirety.

INTRODUCTION

Antibodies, also referred to as immunoglobulins (Ig), are soluble blood or interstitial fluid glycoproteins that play a key role in humoral immunity of the Vertebrata. Antibodies are produced by B-cells in response to the foreign biological and chemical substances (antigens) of various structure. Due to high specificity and high affinity to the certain antigen, and to ability of producing antibodies against the unlimited antigen repertoire, antibodies and their derivatives are one of the most important reagents to be used in both fundamental and applied medical research.

Classical antibodies [1, 2] are represented by large multimeric proteins (IgG ~150 KDa) which comprise two identical heavy H-chains (one variable VH domain, three constant domains CH1, CH2 and CH3, and a hinged domain between CH1 and CH2) and two identical light L-chains (comprising of the variable domain VL and constant domain CL). A four-chain molecule has non-covalent and covalent (disulfide) bonds connecting the chains. Papain protease can be used to break down an antibody molecule into two fragments: Fab (Fragment antigen binding) and Fc (Fragment crystallizable). Therefore, one region of the molecule (Fab) defines its antigen-related specificity, and another region (Fc) exercises the effector functions targeted to antigen elimination [3, 4]. CH1 and CH2 domains of H-chain are spaced by a hinge region that assures the mobility of Fab-region and the interaction of IgG molecule with Ig effector receptors exposed on the cells. CH2 domain contains the regions binding with FcY receptors that mediate the cell activation (ADCC and ADCP) and with complement system molecules (CDC). In addition, this domain contains the site that is an attach point for carbohydrates for all immunoglobulin isotypes. CH3-domain pretty much determines the stability of IgG dimer and interacts with FcRn-receptor on the cell surface establishing the pharmacokinetic properties of antibodies as well as their metabolism and distribution in the body. The combination of complementarity determining regions (CDR) of the variable domain of the heavy chain (VH) and the variable domain of the light chain (VL) forms an antigen-binding fragment, while the framework regions of the variable domains and the constant domains are not directly involved in antigen recognition. A minimized Fab-derivative for classical antibodies is a single-chain construct in which variable domains of the heavy and light chains are connected with a linker sequence (scFv).

Finding of significant amounts of specific non-classical antibodies of simplified structure in the blood of Camelidae animals (camels, llamas, vicunas) was a valuable discovery [5]. Such antibodies (heavy chain antibody, HCAb) consist of a dimeric single shortened heavy chain (without CH1 domain) with no light chain at all. Antigen-binding fragment of HCAb is formed by only one heavy chain variable domain (VHH), which is connected through the hinged region to Fc-domain. Rather often VHH is called a single-domain antibody, "nanobody", "mini-antibody" or "nano-antibody". It appeared that in addition to the small size (12-15 KDa), such isolated mono-domain structure has a number of advantages compared to classical IgG antibodies, namely aggregation, chemical and thermal stability. VHH antibodies can be successfully cloned and expressed in bacterial and yeast cells. Having said properties, these antibodies were developed in therapeutic direction by Ablynx Company and in the direction of laboratory and industrial chromatography (CaptureSelect affinity products).

Heavy chain antibodies comprising a dimer of a single Ig heavy chain were first discovered by electrophoretic analysis of immunoglobulins in the serum obtained from various representatives of Camelidae family [5]. The relative fraction of HCAb varies from about 15-25% (of all IgG) in llamas and vicunas to about 60-80% in camels [6].

It is assumed that non-classical HCAb, at least in case of Camelidae, resulted from relatively recent evolution of the genes of classical antibodies. Two heavy chain constant domains, CH2 and CH3, in case of HCAb and classical antibodies are highly conserved. In HCAb there is no domain corresponding to the first constant domain CH1 of classical antibodies. Dromedary genome contains a cluster of about fifty VH- and forty VHH-generative genes followed by multiple genes of D-segments, J-segments and genes encoding the constant regions (Cμ, Cγ, Cε and Cα). It is clear that some of Cγ-genes serve to form HCAb (mutations result in the loss of CH1-domain), and others—to form classical antibodies (with remained CH1-domain). The same genes of D- and J-segments may randomly connect to either one of VH-genes or one of VHH-genes. This indicates that VH- and VHH-genes are located in the same gene locus [7-10].

The organization of variable domains of non-classical antibodies (VHH) and variable domains of classical antibodies (VH) is very similar, as human VH-domains of IgG3 subclass have high homology to VH and VHH of Camelidae. In both cases, V-domains comprise four conservative framework regions FR surrounding three hypervariable complementary-determining regions (CDR). In addition, in both cases a 3-D structure typical for immunoglobulin V-domain is formed of two β-layers, one of which comprises 4 amino acid sequences and another—of 5 amino acid sequences [11, 12]. All three CDRs in this structure form a cluster on one side of V-domain, where they participate in antigen recognition and are located in the loops connecting β-structures. However, there are several important distinctions related to the functioning of single-domain VHH. Thus, CDR1 and CDR3 of VHH are significantly enlarged. Complementary-determining regions of VHH often contain cysteine residues in two fragments at a time (usually in CDR1 and CDR3, less often—in CDR2 and CDR3). The studies of VHH crystal structures have shown that these cysteine residues form disulfide bonds and provide additional stability to the loop structure of these antibodies [12]. The most strong and reproducible distinguishing feature of VHH is represented by four substitutions of hydrophobic amino acid residues by hydrophilic ones in the second framework region (Val37Phe, Gly44Glu, Leu45Arg, Trp47Gly according to the Kabat numbering [13]). This framework region of VH-domain is highly conservative enriched with hydrophobic amino acid residues and is essential for linking to the light chain variable domain VL. VHH-domain differs greatly in this aspect: substitutions of hydrophobic amino acids by hydrophilic makes the association of VHH and VL impossible. These substitutions also explain the high solubility of VHH (nano-antibody) when it is obtained as a recombinant protein [14].

It appears that the repertoires of paratopes (antigen-binding parts of an antibody) possible for HCAb and classical antibodies may be significantly different. Since these two antibody types co-exist in the same organism, it can be assumed that they do not compete but are complementary to each other. For example, it was repeatedly noted that both antibody types could occur in parallel, exclusively or in different ratios with regard to various epitopes of the antigen material upon immunization of the very same animal. Despite the suspected lower variety of paratopes possible for single-domain antibodies compared to the classical two-domain antibodies, many publications have clearly demonstrated that HCAb can be obtained against the most diverse epitopes of a rather wide range of antigens [15]. Apparently, this is due to enlarged CDR1 and CDR3 regions. We also should note the surprisingly large (compared to V-domains of classical antibodies) number of somatic hypermutations in VHH that are likely to accumulate during the affine maturation of the antibody during the immunization [16]. X-ray diffraction analysis revealed that antigen-binding loop regions of VHH are able to form structures unusual for classical V-domains [12, 16]. In case of VH- and VL-domains of classical antibodies, all six CDRs contribute almost the same to antigen binding; while in case of VHH, CDR3 is usually the most important for the formation of a paratope. It has been shown that CDR3 in VHH (but not in VH or VL) is capable of forming uncommonly long finger-structures that can deepen into the antigen structure and, in particular, detect the active sites of enzymes [12]. Small size of the antigen-binding region of VHH and its ability to form unusual emerging paratopes explain how HCAb can be obtained able to recognize epitopes inaccessible for the classical antibodies (for example, production of antibodies that effectively inhibit enzymes) [17].

For all the high potential of the specificity unique compared to the classical IgG antibodies, the therapeutic use of a single-domain VHH is sometimes limited due to its rapid elimination form the organism. There are several solutions designed to improve the pharmacokinetics of VHH structures, including the chemical conjugation with PEG and covalent binding to polypeptides mediating the reduced clearance (such as HSA or Fc-fusion proteins that possess the half-life of up to three weeks) [18,19,20]. Small peptides attached to VHH by the recombinant technology and capable of high-affinity non-covalent interaction with said components (HSA and IgG) in human blood have been successfully used [21]. However, the technological effectiveness and immunogenicity of these approaches remain questionable, and the feasibility of using thereof in either clinical or earlier study phases is now under investigation.

In addition, the largest limitations of using antibodies as medicinal agents are due to their aggregation and chemical stability affinity and immunogenicity. Since the majority of monoclonal antibodies are obtained on the basis of murine ones, the regular use of such antibodies in humans causes the development of immune response to antibody therapy (for example, allergic reactions). These types of immune response finally result in the lack of efficacy at least, and in potential anaphylactic reactions at worst. From the other hand, aggregation- or chemically unstable therapeutic antibodies reduce the therapeutic properties of the drug product over time and may increase its immunogenicity upon administration to human patients.

According to aforesaid, it is important to develop VHH-based antibodies with improved (in comparison to previously known antibodies) functional and therapeutic features, particularly increased aggregation, chemical and thermal stability and improved affinity, which would at the same time be easily obtained on industrial scale.

BACKGROUND OF THE INVENTION

The background of the invention provides the information on various antibody constructs containing the VHH domain.

PCT/EP2008/066368 publication describes antibodies that comprise separate variable domains linked with Fc-fragment. Nano-bodies can be used as variable domains with Fc obtained from IgE type antibodies. Said domain and Fc fragments can be connected through a linker located in the hinge domain.

Patent application US 2009/0202979 disclosed antibodies comprising complete VHH antibodies or parts thereof directly connected to the constant regions of human antibodies.

In addition, amino acid substitutions are known that affect the physical-chemical and biological properties of antibodies.

For example, application US 20110028348 describes the heavy chain variable domains wherein amino acid substitutions were introduced in positions 35, 45, 47, 93-100 and 100a to improve the hydrophilic properties of the antibody obtained.

Now, the methods have been developed to optimize the structure of isolated VHH and VH mono-domains in order to reduce the immunogenicity and improve the aggregation stability thereof.

Thus, Vincke at al. [22] have found that Glu-49→Gly and Arg-50→Leu substitutions in characteristic amino acids result in the obtainment of a new domain that is more stable yet less soluble. Other substitutions in the framework region FR-2 Phe-42→Val and Gly/Ala-52→Trp are crucial for antibody affinity to the antigen due to re-orientation of H3-loop, so that the dissociation constant increases 6-10-fold ($6.85 \cdot 10^{-3}$ l/sec). Phe-42→Val substitution caused the reduced stability of antibodies obtained. The substitution of Gly-49 and Leu-50 in VH-sequence resulted in the lower stability of the domain, while Glu-49 and Arg-50 humanization in VHH allows obtaining the stable variable domains.

It is known from the literature, that in the presence of short HCDR3 regions neutralizing the shading effect of the conformation of classical VHH, and upon introduction of VH-characteristic Trp-47→Gly-47 substitution as well as Tyr-37→Val-37, Glu-4→Gly-44 and Arg-45→Leu-45, the isolated VHH domains can regenerate the ability to bind with VJ domain [24].

The relationship between the increased aggregation stability of therapeutic antibodies of classical IgG structure and the reduced immunogenicity thereof was demonstrated in multiple studies and summarized in the review by Hermeling et al., 2004 [25]. Yet there were no antibodies revealed that comprise VHH domains but were linked to the variable domains of the light chains within the full-size human IgG.

Therefore, there is a need for development of a new format of antibodies that would have improved stability and affinity, good expression and low immunogenicity Besides, no approaches were earlier described with regard to the development of such molecules that would be easy to obtain, have improved aggregation stability, increased affinity and high expression level in the mammal cell culture.

According to previously mentioned, this invention is the first to describe antibodies comprising VHH-derivatives that are able to bind to variable domains of the light chains of the full-size human IgG, which results in the formation of a construct that is similar to the native one (and, hence, having low immunogenicity) but has improved aggregation stability, increased affinity, and a structure of a therapeutic monoclonal antibody.

BRIEF DESCRIPTION OF DRAWINGS

FIG. 1 shows the scheme for development and optimization of an aggregation-resistant VHH-based antibody.

FIG. 2 shows human recombinant IL-17A-His6-FLAG product (15% PAGE+β-ME), wherein: Lane 1: $9^{10}$ 0.25 µg+β-ME; Lane 2: $9^{10}$ 0.5 µg+β-ME; Lane 3: $9^{10}$ 1 µg+β-ME; Lane 4: ---; Lane 5: Enzyme marker unstained; Lane 6: Medium before application to IMACBioRad; Lane 7: Medium after application to IMACBioRad; Lane 8: Washing 1; Lane 9: Washing 2; Lane 10: Washing 3; Lane 11: Elution 5 µL; Lane 12: Elution 5 µL; and Lane 13: Elution 10 µL. FIG. 3 shows VHHIgG1 products with various amino acid substitutions at position 45 of VHH domain (12% PAGE+β-ME). Lane 1: Control IgG1 2.5 µg; Lane 2: Control IgG1 5 µg; Lane 3: Control IgG1 10 µg; Lane 4: -; Lane 5: Enzyme PW marker unstained; Lane 6: VHHIgG1 aIL17 A45/K8 µL; Lane 7: VHHIgG1 aIL17 D45/K8 5 µL; Lane 8: VHHIgG1 aIL17 F45/K8 5 µL; Lane 9: -; Lane 10: VHHIgG1 aIL17 G45/K8 cult liq before 5 µL; Lane 11: VHHIgG1 aIL17 G45/K8 cult liq after 5 µL; Lane 12: VHHIgG1 aIL17 G45/K8 5 µL; Lane 13: -; Lane 14: VHHIgG1 aIL17 H45/K8 5 µL; and Lane 15: VHHIgG1 aIL17 I45/K8 5 µL. FIG. 4 shows products with various amino acid substitutions at position 45 of VHH domain (8% PAGE, free of β-ME). Lane 1: Control IgG1 2.5 µg; Lane 2: Control IgG1 5 µg; Lane 3: Control IgG1 10 µg; Lane 4: -; Lane 5: Enzyme PW marker unstained; Lane 6: -; Lane 7: VHHIgG1 aIL17 A45/K8 5 µL; Lane 8: VHHIgG1 aIL17 D45/K8 5 µL; Lane 9: VHHIgG1 aIL17 F45/K8 5 µL; Lane 10: -; Lane 11: VHHIgG1 aIL17 G45/K8 cult liq before 5 µL; Lane 12: -; Lane 13: VHHIgG1 aIL17 H45/K8 cult liq after 5 µL; Lane 14: -; and Lane 15: VHHIgG1 aIL17 I45/K8 5 µL.

FIG. 7A shows amino acid sequences for 3 different VHH sequences that demonstrate binding affinity with IL-17A, and 7B shows three VL sequences for pairing with 3VHH sequences.

FIG. 9 shows the Amino acid sequences for 4 different VHH mutants. The sequence listings shown at FIG. 9 correspond to SEQ ID Nos 17-21.

FIG. 16 illustrates four sequences of the variable domains of human light chains VK1A7, VK3c8, VK3c18 and VK4c1E12 that were combined with high-affinity mut4 VHHFab. The sequence listings shown at FIG. 16 correspond to SEQ ID Nos 22-25.

FIG. 18 shows gel electrophoresis in 12% PAGE+β-Me. Lane 1: IgG1 control, 2.5 µg; Lane 2: Ferments unstained marker; Lane 3: 44V45T VHHIgG1c8 culture liquid before purification 10 µL; Lane 4: 44V45T VHHIgG1c8 culture liquid after purification 10 µL; Lane 5: 44V45T VHHIgG1c8 5 µL; Lane 6: 44D45T VHHIgG1c8 5 µL; Lane 7: 44T45T VHHIgG1c8 5 µL; Lane 8: 44A45T VHHIgG1c8 5 µL; Lane 9: 44S45T VHHIgG1c8 5 µL; Lane 10: 44v45V VHHIgG1c8 5 µL; Lane 11: 44D45V VHHIgG1c8 5 µL; Lane 12: 44A45V VHHIgG1c8 5 µL; and Lane 13: 44T45V VHHIgG1c8 5 µL. FIG. 19 show gel electrophoresis in 12% PAGE+b-Me. Lane 1: IgG1 control, 2.5. µg; Lane 2: IgG1 control, 5 µg; Lane 3: IgG1 control, 10 µg; Lane 4: Fermentos unstained PW marker; Lane 5: 44V45T VHHIgG1c8 5 µL; Lane 6: 44D45T VHHIgG1c8 5 µL; Lane 7: 44T45T VHHIhG1c8 5 µL; Lane 8: 44A45T VHHIgG1c8 5 µL; Lane 9: 44S45T VHHIgG1c8 5 µL; Lane 10: 44V45V VHHIgG1c8 5 µL; Lane 11: 44D45V VHHIgG1c8 5 µL; Lane 12: 44A45V VHHIgG1c8 5 µL; and Lane 12: 44T45V VHHIgG1c8 5 µL.

FIGS. 23A-23B show the Results obtained for kinetic parameters of BCD109 interaction with IL17A of various origins.

DEFINITIONS

Figure 2:
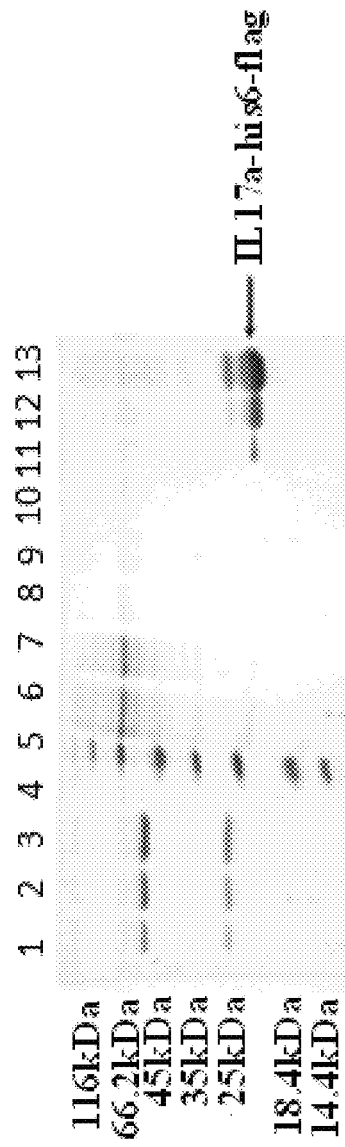
FIGS. 2, 3, 4 illustrate SDS gel electrophoresis of VHHIgG1 antibodies comprising various amino acid substitutions.

"Monoclonal antibody" as used herein relates to an antibody obtained from llama, chimeric antibody, humanized antibody or fully human antibody, unless otherwise stated in the present application. Monoclonal antibodies according to the invention can be produced using, for example, recombinant technology, phage display technology, synthetic technology or the combinations of these or other technologies well known from the prior art.

"Monoclonal antibody" refers to an antibody obtained from a single copy or a clone including, for example, any eukaryotic, prokaryotic or phage clone, rather than to production method thereof. "Monoclonal antibody" can be an intact antibody (with full or full-length Fc-region), actually intact antibody, an antibody part or fragment comprising an antigen-binding region, for example, Fab-fragment, Fab'-fragment or F(ab')2-fragment from llama or chimeric, humanized or human antibody. "Fab"-fragment comprises a variable light chain domain and a constant light chain domain as well as a variable heavy chain domain and first constant heavy chain domain (CH1). "F(ab')2" antibody fragment contains a pair of Fab-fragments which are mostly covalently bound by hinged cysteine residues at C-terminal regions. Other chemical bonds between antibody fragments are also well known from the state of art.

In addition, "monoclonal antibody" as used herein can be a single-chain Fv that can be obtained by binding DNA encoding VHH and VL with a linker sequence. As long as the protein keeps its ability of specific or preferable binding to the target (for example, epitope or antigen), it is covered by the term "antibody". Antibodies can be either glycosylated or not and are within the frames of the invention.

The term "derivative" or antibody "variant", as used herein, refers to a molecule the amino acid sequence of which differs from the parental sequence by adding, deletion and/or, substitution of one or more amino acid residues in the sequence of parental antibody. In the preferred embodiment, an antibody contains at least one (for example, from one to about ten preferably 2, 3, 4, 5, 6, 7 or 8) amino acid substitutions in FR- or CDR-regions of the parental antibody. This application defines the identity or homology regarding the sequence of a variant antibody as the percentage of amino acid residues in a variant antibody sequence that are identical to residues in parental antibody after aligning the sequences and, if needed, cutting in order to achieve the maximum percentage identical sequence.

An antibody derivative (from parental one) keeps its ability to bind the same antigen or, preferably, epitope as that with which the parental antibody binds, or, preferably, exhibits at least one property or biological activity exceeding that of the parental antibody. For example, the antibody preferably has a better aggregation stability, more strong affinity, improved pharmacokinetics or increased ability to inhibit the antigen biological activity, compared to parental antibody.

The term "VHH-derivative", as used herein, refers to the derivatives of VHH antibodies the amino acid sequence of which differs from the sequence of parental VHH antibody by substitution of one or more amino acid residues in the sequence of parental antibody. In the preferred embodiment, VHH antibody contains at least one (for example, from one to about ten preferably 2, 3, 4, 5, 6, 7 or 8) amino acid substitutions in FR- or CDR-regions of the parental antibody.

An antibody derivative keeps its ability to bind the same antigen or, preferably, epitope as that with which the parental antibody binds, or, preferably, exhibits at least one property or biological activity exceeding that of the parental antibody. For example, the antibody preferably has a better aggregation stability, more strong affinity, improved pharmacokinetics or increased ability to inhibit the antigen biological activity, compared to parental antibody.

"Parental VHH antibody" or "initial VHH antibody", or "wild VHH antibody" as used herein refers to VHH antibody isolated from an immunized or non-immunized Camelidae animal encoded with amino acid sequence that is used to produce a VHH variant. Parental antibody can have a framework sequence originating from Camelidae (with respect to VHH variable domain), but preferably the frame sequence of the light chain variable domain is of completely or substantially human origin.

"Parental", "initial", or "wild" antibody as used herein refers to an antibody encoded with amino acid sequence that is used to produce a variant. Parental antibody can have a framework sequence originating from Camelidae (with respect to VHH variable domain), but preferably the frame sequence of the light chain variable domain is of completely or substantially human origin.

As used herein, the term "specifically binds" refers to such a situation in that one party involved in the process of specific binding does not significantly bind molecules other than its specific binding partner (partners). This term also applies if, for example, an antigen-binding site of the antibody according to the invention is specific for particular epitope that is carried by a number of antigens; in this case, the specific antibody with an antigen-binding site will be able to bind specifically with various epitope-carrying antigens. Thus, the monoclonal antibody according to the invention specifically binds to human IL-17 (IL-17A), while it does not specifically bind human IL-17B, IL-17C, IL-17D or IL-17E. Moreover, a monoclonal antibody of the invention specifically binds human IL-17 and IL-17 from cynomolgus monkey, but does not specifically bind neither rat IL-17 nor murine IL-17.

As used herein, the term "preferably binds" refers to such a situation in that an antibody binds a specific antigen at least by 20% more, preferably by about 50%, or 2-fold, 20-fold, 50-fold or 100-fold more than it binds any other antigen, as measured according to the procedures known from the prior art (for example, competitive ELISA or $K_D$ measurements obtained using Octet apparatus). Antibody can preferably bind one epitope within an antigen but not bind another epitope of the same antigen. Thus, an antibody of the invention preferably binds human IL-17 but not rabbit IL-17.

As used herein, the term "epitope" refers to the molecule part that can be recognized by and bind an antibody via one or several antigen-binding sites of an antibody. Epitopes often comprise the chemically surface-active groups of molecules such as amino acids or sugar side chains, and have specific 3-D structural characteristics. "Inhibiting epitope" and/or "neutralizing epitope" means an epitope that, as in the context of an intact antigen molecule and binding an antibody specific to said epitope, causes in vivo or in vitro loss or reduction of activity of the molecule or organism that contains the molecule.

As used herein, the term "epitope" also refers to a polypeptide fragment, having antigenic and/or immunogenic activity in animals, preferably in mammals such as mice and humans. The term "antigenic epitope" as used herein is a polypeptide fragment which can specifically bind the antibody and can be detected by any technique well known from the prior art (for example, by means of the standard immunoassay). Antigen epitopes are not necessary immunogenic, but they can possess immunogenicity. "Immunogenic epitope" as used herein is defined as a polypeptide fragment that evokes an antibody response in animals, as determined by any method of the prior art. "Nonlinear epitope" or "conformational epitope" contains nonadjacent polypeptides (amino acids) within the antigen protein, which binds with epitope-specific antibody.

Expressed "functional activity" or "functional characteristics" or the terms "biological activity" or "activity" referring to an antibody according to the invention are interchangeable as used herein, and include but not limited to: epitope/antigen affinity and specificity; ability to neutralize or be an antagonist to IL-17 in vivo or in vitro; $IC_{50}$; antibody stability and in vivo immunogenicity of the antibody. Other biological properties or antibody characteristics identified from the prior art include, for example, the cross-reactivity (i.e. reaction with non-human homologs of the target peptide or with other proteins or targets) and ability to retain high levels of protein expression in mammal cells. Aforementioned properties or characteristics may be observed, measured or evaluated using the procedures recognized in the prior art, including but not limited to ELISA, competitive ELISA, Octet analysis, neutralization assay in vitro or in vivo without limitation, receptor binding, production and/or release of cytokine or growth factor, signal transduction and immune histochemical study of tissue sections obtained from various sources including humans, primates or any other source.

The population of "monoclonal antibodies" as used herein refers to a homogenous or essentially homogeneous antibody population (i.e. at least or 96%, but more preferably no less than about 97 or 98%, or further preferably at least 99% of antibodies in the population will compete for the same antigen/epitope in ELISA, or further preferably antibodies are identical regarding their amino acid sequences).

A native full-size antibody is represented by immunoglobulin molecule comprising four polypeptide chains (two heavy H chains of about 50-70 KDa for the full length, and two light L chains of about 25 KDa for the full length) linked via disulfide bonds. Amino-terminal part of each chain comprises a variable domain of about 100-110 or more amino acids that are responsible for binding an antigen. Carboxyl-terminal domain of each chain determines the constant region that is mostly responsible for the effector function. Light chains are classified as kappa and lambda and have specific constant regions. Each light chain is characterized in comprising a variable N-terminal light chain region (hereafter referred to as VL or VK) and a constant light chain region that consists of a single domain (CL or CK). Heavy chains are classified as γ, δ, α, μ and ε and define classes of immunoglobulins: IgG, IgM, IgA, IgD and IgE, respectively; some of them can be additionally divided into sub-classes (isotypes) such as IgG1, IgG2, IgG3, IgG4, IgA1 and IgA2. Each heavy chain type is characterized by a specific constant region Fc. Each heavy chain comprises a variable N-terminal region (hereafter referred to as VH) and constant region CH. Constant heavy chain region consists of three domains (CH1, CH2 and CH3) for IgG, IgD and IgA, and of 4 domains (CH1, CH2, CH3 and CH4) for IgM and IgE. VH, VHH and VL can also be divided into so-called hypervariable regions (complementarity determining regions, CDR) interspersing with more conservative framework regions (FR). Each variable domain comprises three CDRs and FRs located in the following order from N-terminus to C-terminus: FR1, CDR1, FR2, CDR2, FR3, CDR3 and FR4.

In the present application, 3 heavy chain CDRs are referred to as "HCDR1, HCDR2 and HCDR3", while 3 light chain CDR are referred to as "LCDR1, LCDR2 H LCDR3". CDRs contain the majority of amino acid residues specifically interacting with an antigen. CDR-residues are numbered and positioned in compliance with Kabat Numbering Scheme.

The term "antigen" refers to an antigen target against which an antibody can be reactive; it is used herein in the same way as specialists use it in the this technical field, and includes but is not limited to, polypeptides, peptides, polysaccharides, glycoproteins, polynucleotides (for example, DNA), or chemical antigens, receptors or interleukins. Interleukins can include interleukins of various groups, such as interleukin 1 (alfa and beta), interleukin 2, interleukin 3, interleukin 4, interleukin 5, interleukin 6, interleukin 7, interleukin 8, interleukin 9, interleukin 10, interleukin 11, interleukin 17, interleukin 18 and interleukin 33.

The term "antigen" can also be used to describe the material that is used for immunization of animals (for example, llama) with the purpose of production of antibodies of the invention. In that context, "antigen" can have a broader meaning and may cover purified forms of an antigen as well as non-purified or not fully isolated, or purified antigen products such as cells, cell lysates, or supernatants, cell fractions, for example, cell membranes etc. with added haptens conjugated with a protein-carrier. Antigen used for immunization does not necessary mean an antigen structurally identical to an antigen target to which, finally, an antibody of the invention is able to bind. Usually, antigen used for immunization is a downsized version of an antigen target, for example, a fragment comprising an immunogenic epitope. More details about antigens used for immunization are described in the literature and may be familiar to the specialist in this technical field.

Variable regions of each light/heavy chain pair form antigen-binding sites of an antibody. Thus, an intact IgG antibody has two binding sites. Except for bi-functional or bi-specific antibodies, two binding sites are identical. According to the present application, "antigen-binding region" or "antigen-binding site", or "antigen-binding domain", are interchangeable, as used herein, with refer to an antibody region comprising amino acid residues interacting with an antigen and giving the antibody its specificity and affinity to an antigen. This antibody fragment includes the frame amino acid residues necessary for maintaining the proper conformation of antigen-binding residues.

Preferably, CDR of VHH antigen-binding region or the entire antigen-binding region of an antibody of the invention fully originates from Camelidae family or is substantially of Camelidae origin, and comprises specific amino acid residues changed, for example, substituted with various amino acid residues (for example, refer to Table 6) in order to improve the particular properties of an antibody (for example, $K_D$, $k_{off}$ or $IC_{50}$). Preferably, the antibody framework regions in accordance with the invention are of Camelidae origin or of human origin, or substantially of a human origin (at least by 80, 85, 90, 95, 96, 97, 98 or 99% of human origin), and comply with Kabat numbering.

"Antibody fragment" may be represented by an antibody fragment or antibody fragment that has the activity of a full-size antibody. Said antibody fragment may be represented by F(ab')2, F(ab)2, Fab', Fab Fv and scFv.

"Interleukin 17", also referred to as "IL-17" or "IL-17A", is a 20-30 kD homo-dimeric glycoprotein. The gene of human IL-17 encodes the protein consisting of 155 amino acids and having a 19 amino acid signal sequence and 136 amino acid mature segment. Amino acid sequence of human IL-17A is by 80%, 63% and 58% similar to amino acid sequences of rabbit, mouse and rat, respectively. Amino acid sequence of human IL-17A is by 97% identical to IL-17A of cynomolgus monkey.

The term "antibody" when applied in relation to anti-IL-17 monoclonal antibody of the invention (hereafter referred to as an "antibody of the invention"), as used herein, means a monoclonal antibody.

As used herein, the terms "inhibit" or "neutralize" regarding to the activity of an antibody of the invention shall mean the ability to block, prevent, restrict, slow down, stop, reduce or reverse significantly, for example, the development or severity of inhibition subject, including but not limited to biological activity (such as activity of IL-17) or property, disease or condition. Binding of an antibody according to the invention with IL-17 results in the inhibition or neutralization of IL-17 activity preferably of at least 20, 30, 40, 50, 60, 70, 80, 90, 95% or higher.

The term "separated" or "isolated" with regard to nucleic acids or protein products (such as an antibody) refers to the nucleic acid molecule or protein molecule that is identified and separated from at least one of contaminating substances to which it is usually combined in the natural source. Preferably, an "isolated antibody" is an antibody that substantially contains no other antibodies that have particular antigenic specificity (for example, pharmaceutical compositions of the invention contain an isolated antibody that specifically binds IL-17A and substantially contain no antibodies that specifically bind antigens other than IL-17A).

The term "Kabat numbering scheme" or "numbering according to Kabat" as used herein refers to the system for numbering of amino acid residues that are more variable (i.e. hypervariable) than other amino acid residues in variable regions of heavy and light chains of an antibody (Kabat et al. Ann. NY Acad. Sci., 190:382-93 (1971); Kabat et al. Sequences of Proteins of Immunological Interest, Fifth Edition, U.S. Department of Health and Human Services, NIH Publication No. 91-3242 (1991)).

Polynucleotide is "functionally bound" if it has functional linkages to other polynucleotide. For example, promoter or enhancer is functionally bound to the coding sequence if it affects the sequence transcription. Polypeptide is "functionally bound" to another polypeptide if polynucleotides coding thereof are functionally bound, preferably if they are located in the same open reading frame.

The term "DNA construct", as used herein, refers to DNA or its fragment coding an antibody of the invention. Generally, DNA or its fragment that codes an antibody (for example, an antibody of the invention) is functionally (operably) bound, within an open reading frame, to at least one other DNA fragment that codes an additional polypeptide (for example, domain or region of a receptor for another cytokine, such as IL-2-receptor), and then is inserted into an appropriate expressing vector. Normally, DNA constructs are formed in such a way that several DNA fragments coding certain antibody sites are functionally associated within a reading frame to obtain a solid construct that codes either an entire antibody or its functional fragment. For example, DNA construct would encode an antibody from N-terminus to C-terminus. Such antibodies can be expressed, isolated and evaluated regarding their activity.

The term "vector" refers to nucleic acids that were obtained synthetically and via biotechnology and contain a certain and known in the present field set of sequence functional elements. Certain vectors can autonomously replicate in host cells to which they were introduced, while other vectors can integrate into host cell genome and replicate together with the host genome. Moreover, some vectors can mediate the expression of genes to which they are functionally bound. In this application such vectors are called "recombinant expression vectors" (or "expression vectors"); exemplary vectors are well known from the prior art.

As used herein, the terms "cell", "host cell", "cell line" and "cell culture" are interchangeable and refer to an individual cell or cell culture that is a recipient of any isolated polynucleotide according to the invention or any recombinant vector (recombinant vectors) that contains the sequence of an antibody of the invention. Host cells involve generations obtained from an individual host cell; generations may not necessary be completely identical (regarding the morphology or full DNA complement) to original host cell due to natural, accidental or intended mutations and/or variations. A host cell includes cells that were transformed, transduced or infected with recombinant vector, or a monoclonal antibody that expresses a polynucleotide according to the invention or its heavy or light chain. Host cell that contains a recombinant vector according to the invention (either incorporated into host chromosomes or not) can also be called "recombinant host cell". Preferable host cells to be used in the invention are CHO cells (for example, ATCC CRL-9096), NS0 cells, SP2/0 cells, COS cells (ATCC, for example, CRL-1650, CRL-1651) and HeLa (ATCC CCL-2). Additional host cells to be used in the invention include plant cells, yeast cells, other mammalian cells and prokaryotic cells.

The term "Specific binding" between an antibody and an antigen target (antigen) refers to immunological specificity. Antibody can specifically bind an antigen target if it binds an antigen epitope stronger than other antigen epitopes. Specific binding does not exclude the cross-reactivity with other antigens that carry similar antigen epitopes.

VL domains in antibodies of the invention can be either VL lambda type or VL kappa type. The term "VL domain" covers both VL lambda and VL kappa isotypes that contain one or more amino acid substitutions, insertions or deletions.

The term "pharmaceutical composition" covers the formulation and/or composition containing a therapeutically effective amount of an antibody of the invention plus excipients (carriers, diluents, vehicles, solvents and other excipients such as water for injection with a pH that was brought to 5.5 with citric acid, water containing mannitol as a lyoprotectan, etc.).

The term "use" or "treatment" applies to the ability of using an antibody of the invention or a pharmaceutical composition containing thereof to treat, relief the course of the disease, expedite the remission or reduce the recurrence rate for the disease or disorders mediated by receptors with which an antibody of the invention can bind.

DESCRIPTION OF THE INVENTION

The present invention proposes humanized monoclonal antibodies, preferably IgG type, which have an increased affinity and improved aggregation stability, wherein variable domains are represented by a combination of VHH-derivative with a variable domain of the light chain $V_L$.

In one embodiment, VHH-derivative of an antibody of the invention may comprise amino acid substitutions at positions $44X_2 45X_3$, where $X_2$=G, A, V, S, T; a $X_3$=A, V, T, H; or combinations thereof (44 and 45 designate the positions for amino acid substitutions). Hereinafter the position of amino acid substitution is indicated using Kabat numbering scheme (http://www.bioinf.org.uk/abs/).

Another embodiment involves an antibody of the invention that has improved aggregation stability of VHH-derivative compared to initial IgG antibody comprising VHH isolated from an immunized animal, wherein an immunized animal can be from Camelidae.

Another embodiment of the invention involves an antibody that comprises $V_{HH}$-derivative that is a variable domain of the heavy chain of an antibody isolated from an immunized animal from Camelidae family. Herein $V_{HH}$-derivative can have additional amino acid substitutions typical for humans at any positions, except for the following substitutions at positions 44 and 45:
a) $44X_2$, wherein X2=G, A, V, S, T;
b) $45X_3$, wherein X3=A, V, T, H;
or combinations thereof.

Another embodiment involves an antibody of the invention that comprises $V_{HH}$-derivative that can be represented by a heavy chain variable domain isolated from non-immunized animal from Camelidae family. Herein $V_{HH}$-derivative can have additional amino acid substitutions typical for humans at any positions, except for the following substitutions at positions 44 and 45:
a) $44X_2$, wherein X2=G, A, V, S, T;
b) $45X_3$, wherein X3=A, V, T, H;
or combinations thereof.

Another embodiment involves an antibody of the invention that comprises a light chain variable domain $V_L$ that is a derivative of a human antibody. In additional embodiment of the invention, the light chain variable domain $V_L$ is a humanized fragment of an animal antibody.

Another embodiment involves an antibody of the invention that comprises a $V_{HH}$-derivative that contains cysteine-44 (Kabat numbering scheme), and a light chain variable domain $V_L$ that contains cysteine-100 (Kabat numbering scheme).

Another embodiment of the invention involves an antibody of any of the following isotypes: IgG1, IgG2, IgG3 or IgG4.

Another embodiment involves an antibody of the invention that comprises a non-native modified Fc as a part of IgG.

Another embodiment involves an antibody of the invention that has such aggregation stability that when used in concentrations over 10 mg/ml and stored for >6 months at a temperature of 4° C. the content of aggregates increases by not more than 5% of their initial content in the solution. In additional embodiment of the invention, an antibody has such aggregation stability that when used in concentrations over 10 mg/ml and stored for >2 weeks at a temperature of 37° C. the content of aggregates increases by not more than 5% of their initial content in the solution. Another additional embodiment of the invention involves an antibody that has such aggregation stability that when used in concentrations over 10 mg/ml and stored for >48 h at a temperature of 42° C. the content of aggregates increases by not more than 5% of their initial content in the solution. One more additional embodiment of the invention involves an antibody that has such aggregation stability that when used in concentrations over 10 mg/ml and stored for >6 h at a temperature of 50° C. the content of aggregates increases by not more than 5% of their initial content in the solution.

One embodiment involves an antibody with dissociation constant $K_D \leq 10^{-9}$ M. Another embodiment involves an antibody of the invention that has an antibody-antigen interaction association constant $kon(1/Ms) \geq 10^5$ 1/Ms. One more embodiment of the invention involves an antibody that has a antigen-antibody dissociation constant $dis(1/s) \leq 10^{-4}$ 1/s.

In addition, the invention suggests an antibody fragment. This antibody fragment can be represented by a light chain, heavy chain, variable domains of the light and/or heavy chain that are a part of an antibody sequence, which includes a bio-specific antibody variant. Another embodiment of the invention involves an antibody fragment that is represented by a light chain, heavy chain, variable domains of the light and/or heavy chain that are parts of Fab. The antibody fragment of the invention may be represented by a light chain, heavy chain, variable domains of the light and/or heavy chain that are parts of scFv.

In addition, the invention suggests the methods of production of antibodies of the invention. Said method of antibody production can involve phases selected from the following: directed mutagenesis, display methods, genetic engineering, biochemistry and high-performance biotechnology methods well known for the art, which can include the methods for directed mutagenesis in different positions of VHH domain of Camelidae antibodies.

In addition, the invention provides a DNA construct encoding the antibodies claimed or fragments thereof, and an expression vector comprising one or several DNA constructs of the invention.

Moreover, the invention suggests a cell line comprising said expression vector or DNA construct.

In addition, the invention suggests the method of production of a humanized monoclonal antibody of fragment thereof, which involves the cell line culture in a culture medium under the conditions sufficient to obtain said antibody or fragment thereof, followed by the isolation and purification of obtained antibody or its active fragment.

Moreover, the invention suggests the pharmaceutical composition that contains an antibody or fragment thereof in combination with one or several pharmaceutically suitable excipients, diluents or carriers. Details of the techniques for composition obtainment are described in special biotechnology guidelines, for example in [25].

Another embodiment of the invention involves an antibody or fragment thereof within an active molecule that specifically binds to human IL-17A, wherein said antibody of fragment thereof comprises a derivative of Camelidae heavy chain variable domain ($V_{HH}$) that comprises 3 hypervariable regions HCDR1, HCDR2 and HCDR3, wherein:

HCDR1 comprising the amino acid sequence of SEQ ID NO: 1:
G-T-F-A-T-X32-X33-X34-X35 (numbering according to Kabat index), wherein
X32 is an amino acid selected from the group comprising S, N, K, R, E, W, Q, D, A, V and F;
X33 is an amino acid selected from the group comprising P and S;
X34 is an amino acid selected from the group comprising M and I;
X35 is an amino acid selected from the group comprising G, N, S, A, L, I, R, V and Q;
HCDR2 comprising the amino acid sequence of SEQ ID NO: 2:
X50-I-X52-X52a-S-G-X55-D-R-I-Y-A-D-S-V-K-G, wherein
X50 is an amino acid selected from the group comprising A, G and L;
X52 is an amino acid selected from the group comprising S, D and E;

X52a is an amino acid selected from the group comprising P and A;

X55 is an amino acid selected from the group comprising G, S, T, L, R, D, E, K, A and W;

HCDR3 comprising the amino acid sequence of SEQ ID NO: 3:

C-A-X94-X95-X96-X97-F-X99-X100-X100a-X100b-X100c-X100d-X100e-X100f-D-Y-D-S, wherein X94 is an amino acid selected from the group comprising K, S, T, V, D and G;

X95 is an amino acid selected from the group comprising R and K;

X96 is an amino acid selected from the group comprising G, R, Y, H, D, W and K;

X97 is an amino acid selected from the group comprising R, A, V, S, L and H;

X99 is an amino acid selected from the group comprising D, E, G, A, R, V, K and Q;

X100 is an amino acid selected from the group comprising G, S and N;

X100a is an amino acid selected from the group comprising is an amino acid selected from the group comprising G, T, P, V, R, N and K;

X100b is an amino acid selected from the group comprising V, S, T, L, Y, A, H, G and I;

X100c is an amino acid selected from the group comprising Y, W and S;

X100d is an amino acid selected from the group comprising R, V, L, Y, A, W, K, G, Q and I;

X100e is an amino acid selected from the group comprising T, L, A and S;

X100f is an amino acid selected from the group comprising T, L, G, P, N, A, Q, F, I and D;

b) A variable domain of the light chain (VL) of a human antibody or a variable domain of the light chain of a humanized antibody.

An alternative embodiment involves an antibody or fragment thereof that specifically binds human IL-17A and comprises a derivative of the heavy chain variable domain ($V_{HH}$) comprising 3 hypervariable regions, wherein:

HCDR1 comprising the amino acid sequence of G-T-F-A-T-S-P-M-G (SEQIDNO: 4);

HCDR2, comprising the amino acid sequence of A-I-S-P-S-G-G-D-R-I-Y-A-D-S-V-K-G (SEQ ID NO: 5);

HCDR3 comprising the amino acid sequence of C-A-V-R-R-R-F-D-G-T-S-Y-Y-T-G-D-Y-D-S(SEQIDNO: 6);

b) A variable domain of the light chain ($V_L$) of a human antibody or a variable domain of the light chain of a humanized antibody.

An alternative embodiment involves an antibody that specifically binds human IL-17A and comprises a derivative of the heavy chain variable domain ($V_{HH}$) comprising an amino acid sequence of SEQIDNO: 7 and A variable domain of the light chain ($V_L$) of a human antibody or a variable domain of the light chain of a humanized antibody.

An alternative embodiment involves an antibody or fragment thereof that specifically binds human IL-17A and comprises Vi-derivative, wherein said variable domain comprises an amino acid sequence at least 90% identical to SEQ ID NO: 7.

An alternative embodiment involves an antibody that specifically binds human IL-17A and contains a $V_{HH}$-derivative comprising the amino acid sequence of SEQ ID NO: 7; and a variable domain of the light chain ($V_L$) of a human antibody comprising the amino acid sequence of SEQ ID NO: 8.

An alternative embodiment involves an antibody or fragment thereof that specifically binds human IL-17A and comprises $V_{HH}$-derivative and a variable region of the light chain ($V_L$) of a human antibody wherein said variable domains comprise an amino acid sequence at least 90% identical to SEQ ID NO: 8.

An alternative embodiment involves an antibody that specifically binds human IL-17A and contains the heavy chain comprising SEQ ID NO: 9 amino acid sequence, and the variable domain of a human antibody light chain ($V_L$) comprising SEQ ID NO: 10 sequence. Another embodiment involves an antibody that specifically binds human IL-17A and contains the heavy chain and the light chain, wherein said chains comprise amino acid sequences at least 90% identical to SEQ ID NO: 9 and/or SEQ ID NO: 10.

An alternative embodiment involves an antibody of the invention that specifically binds human IL-17A, wherein said antibody has the binding affinity to human IL-17A characterized with $K_D$ of $\leq 10^{-10}$ M. Another embodiment involves an antibody that specifically binds human IL-17A, wherein the kinetic association constant kon(l/Ms) for human IL-17A is at least $10^5$ l/Msec. Another embodiment involves an antibody that specifically binds human IL-17A, wherein the kinetic dissociation constant dis(l/c) for human IL-17A is not more than $10^{-5}$ l/sec. An alternative embodiment involves an antibody that specifically binds human IL-17A and inhibits the activity of human IL-17A by no less than 50% with respect to any parameter examined by any specific activity testing.

An alternative embodiment involves an antibody that specifically binds human IL-17A, wherein said antibody is produced by mammalian, yeast or bacterial cells.

An alternative embodiment involves an antibody that specifically binds human IL-17A and contains one or more additional amino acid substitutions in Fc-region compared to the native Fc, wherein said substitutions improve physical-chemical and pharmacokinetic properties of an antibody, as compared to an antibody with the native Fc, and do not result in the loss of antibody's ability to bind IL-17A.

An alternative embodiment suggests a DNA construct encoding an antibody that specifically binds human IL-17A. Moreover, the invention suggests an expression vector comprising one or more DNA constructs encoding an antibody that specifically binds human IL-17A. In addition, a host cell was suggested comprising a vector for obtainment of an antibody that specifically binds human IL-17A.

In addition, the invention suggests a method for the production of an antibody that specifically binds human IL-17A, characterized by culturing host cells comprising a DNA construct in a culture medium under conditions suitable to obtain said antibody or fragment thereof, and further isolation and purification of said antibody or active fragment thereof.

Moreover, a pharmaceutical composition was suggested comprising an antibody that specifically binds human IL-17A, and one or more pharmaceutically suitable excipients, diluents or carriers. Said composition can comprise further active pharmaceutical ingredients selected from TNF-α inhibitors. Said composition can be used in the treatment of an IL-17A-mediated disease or disorder. An IL-17A-mediated disease or disorder is selected from: rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroadenitis, asthma, allergic disorders, psoriasis, dermatitis, systemic sclerosis, graft-versus-host disease, graft rejection, acute or chronic immune disease associated with organ grafting, sarcoidosis, atherosclerosis, disseminated intravascular coagulation, Kawasaki disease, Graves'disease, nephrotic syndrome, chronic fatigue syndrome, Wegener's disease, Henoch-Schonlein purpura, microscopic polyangiitis with renal involvement, chronic active hepatitis, uveitis, septic shock, toxic shock syndrome, sepsis syndrome, cachexia, infections, invasions, acquired immune deficiency syndrome, acute transverse myelitis, Huntington chorea, Parkinson disease, Alzheimer disease, stroke, primary biliary cirrhosis, hemolytic anemia, malignancies, heart failure, myocardial infarction, Addison disease, polyglandular autoimmune syndrome type I and type II, Schmidt's syndrome, acute respiratory distress syndrome, alopecia, alopecia areata, seronegative arthropathy, arthropathy, Reiter's syndrome, psoriatic arthropathy, arthropathy associated with ulcerative colitis, enteropathic synovitis, arthropathy associated with *Chlamydia, Yersinia* and *Salmonella*, spondyloarthropathy, atheromatosis disease/coronary sclerosis, atopic allergy, autoimmune bullous disease, pemphigus, pemphigus *foliaceus*, pemphigoid, linear IgA diseases, autoimmune hemolytic anemia, Coombs positive hemolytic anemia, acquired pernicious anemia, juvenile pernicious anemia, Myalgic encephalomyelitis/chronic fatigue syndrome, chronic active hepatic inflammation, cranial giant arteritis, primary sclerosing hepatitis, cryptogenic autoimmune hepatitis, acquired immune deficiency syndrome (AIDS), AIDS-associated diseases, hepatitis B, hepatitis C, common variable immunodeficiency (common variable hypogammaglobulinemia), dilated cardiomyopathy, female sterility, ovarian insufficiency, Premature ovarian failure, pulmonary fibrosis, cryptogenic fibrosing alveolitis, post inflammatory interstitial lung pathologies, interstitial pneumonitis, connective tissue disease associated with interstitial lung disease, mixed connective tissue disease associated with interstitial lung disease, systemic scleroderma associated with interstitial lung disease, rheumatoid arthrisit associated with interstitial lung disease, systemic lupus erythematosus associated with lung disease, dermatomyositis/polymuositis associated with lung disease, Sjogren disease associated with lung disease, ankylosing spondylitis associated with lung disease, diffuse pulmonary vasculitis, hemosiderosis associated with lung disease, drug-induced interstitial lung disease, fibrosis, radiation-induced fibrosis, obliterating bronchiolitis, chronic eosinophilic pneumonia, lung disease with lymphocyte infiltration, post infectious interstitial lung pathologies, gouty arthritis, autoimmune hepatitis, autoimmune hepatitis type I (classic autoimmune or lupoid hepatitis), autoimmune hepatitis type II (associated with anti-LKM antibody), autoimmune hypoglycemia, type B insulin resistance with acanthokeratodermia, hypoparathyroidism, acute graft-associated immune disease, chronic graft-associated immune disease, osteoarthrosis, primary sclerosing cholangitis, type I psoriasis, type II psoriasis, idiopathic leukopenia, autoimmune neutropenia, NOS-kidney diseases, glomerulonephritis, microscopic renal polyangiitis, Lyme disease, discoid lupus erythematosus, idiopathic of NOS-male sterility, antisperm immunity, multiple sclerosis (all types), sympathetic ophthalmia, pulmonary hypertension secondary to connective tissue disease, Goodpasture syndrome, pulmonary manifestations of polyarteritis *nodosa*, acute rheumatic fever, rheumatoid spondylitis, Still's disease, systemic scleroderma, Sjogren's Syndrome, Takayasu disease/arthritis, autoimmune thrombocytopenia, idiopathic thrombocytopenia, autoimmune thyroid disorders, hyperthyroid, autoimmune hypothyroidism (Hashimoto disease), atrophic autoimmune hypothyroidism, primary myxedema, phacogenic uveitis, primary vasculitis, vitiligo, acute hepatic disease, chronic hepatic disease, alcoholic cirrhosis, alcohol-induced liver damage, cholestasis, idiosyncratic hepatic disease, drug-induced hepatitis, non-alcoholic steatohepatitis, allergies and asthma, group B streptococcal infection (GBS), mental disorders (including depressions and schizophrenia), Th1- and Th2-mediated disease, acute and chronic pain (various forms), malignancies such as lung cancer, breast cancer, stomach cancer, bladder cancer, colorectal cancer, pancreatic cancer, ovarian cancer, prostate cancer and hematopoietic malignancies (leukemia and lymphomas), abetalipoproteinaemia, acrocyanosis, acute and chronic infections and infestations, acute leukemia, acute lymphoblastic leukemia, acute myeloid leukemia, acute or chronic bacterial infection, acute pancreatitis, acute renal failure, adenocarcinoma, atrial ectopics, AIDS dementia complex, alcohol-induced hepatitis, allergic conjunctivitis, allergic contact dermatitis, allergic rhinitis, allograft rejection, alpha-I antitrypsin deficiency, lateral amyotrophic sclerosis, anemia, angina, anterior horn cell degeneration, anti-CD3 therapy, antiphospholipid syndrome, hypersensitivity reactions against receptors, aortic and peripheral aneurysms, aortic dissection, arterial hypertension, coronary sclerosis, arteriovenous fistula, ataxia, atrial fibrillation (constant or paroxysmal), atrial flutter, atrioventricular block, B-cell lymphoma, bone graft rejection, bone marrow transplant (BMT) rejection, bundle branch block, Burkitt lymphoma, burns, cardiac arrythmia, myocardial stunning syndrome, cardiac tumor, cardiomyopathy, inflammatory response to bypass, cartilage graft rejection, brain cortex degeneration, cerebellar disorder, chaotic or multifocal atrial tachycardia, chemotherapy-induced disorders, chronic myelocytic leukemia (CML), chronic alcohol addiction, chronic inflammatory pathologies, chronic lymphatic leukemia (CLL), chronic obstructive pulmonary disease, chronic salicylate intoxication, rectocolic carcinoma, congestive cardiac failure, conjunctivitis, contact dermatitis, pulmonary heart, coronary artery disease, Creutzfeldt-Jakob Disease, culture-negative sepsis, cystic fibrosis, cytokine therapy-induced disorders, boxer's encephalopathy, demyelinating disease, dengue hemorrhagic fever, dermatitis, dermatological conditions, diabetes, diabetes mellitus, diabetes-related atherosclerotic vascular disease, diffuse Lewy body disease, congestive dilated cardiomyopathy, basal ganglia disease, Down's syndrome in middle age, motor disorders induced by CNS dopamine blockers, drug sensitivity, eczema, encephalomyelitis, endocarditis, endocrinopathy, epiglottiditis, Epstein-Barr viral infection, erythralgia, extrapyramidal and cerebellar symptoms, familial hemophagocytic lymphohistiocytosis, fetal thymus graft rejection, Friedreich's ataxia, peripheral artery disease, fungal sepsis, gas phlegmon, gastric ulcer, glomerulonephritis, any organ or tissue graft rejection, gram negative sepsis, gram positive sepsis, granulomas due to intracellular organisms, hairy-cell leukemia, Hallervorden-Spatz disease, Hashimoto's thyroiditis, hay fever, heart transplant rejection, hemochromatosis, hemodialysis, hemolytic uremic syndrome/thrombotic thrombocytopenic purpura, bleeding, hepatitis (A), bundle branch arrhythmia, HIV-infections/HIV-neuropathies, Hodgkin disease, hyperkinetic motor disorders, hypersensitivity reactions, hypersensitivity-associated pneumonitis, hypertension, hypokinetic motor disorders, examination of hypothalamo-pituitary-adrenal axis, idiopathic Addison's disease, idiopathic pulmonary fibrosis, antibody-mediated cytotoxicity, asthenia, infantile muscular atrophy, aortal inflammation, influenza virus A, exposure to ionizing radiation, iridocyclitis/uveitis/optic neuritis, ischaemia/reperfusion-induced disorders, ischaemic stroke, juvenile rheumatoid arthritis, juvenile spinal muscular atrophy, Kaposi's sarcoma, renal transplant rejection, legionellosis, leishmaniasis, leprosy, corticospinal damage, lipoedema, liver transplant rejection, lymphoedema, malaria, malignant lymphoma, malignant histiocytosis, malignant melanoma, meningitis, meningococcemia, metabolic/idiopathic diseases, migraine, multiple system mitochondrial disorders, mixed connective-tissue disease, monoclonal gammapathy, multiple myeloma, multiple system degeneration (Mencel Dejerine-Thomas Shi-Drager and Machado-Joseph), myasthenia gravis, intracellular *Mycobacterium avium, Mycobacterium tuberculosis*, myelodysplastic syndrome, myocardial infarction, myocardial ischemic disease, nasopharyngeal cancer, neonatal chronic lung disease, nephritis, nephrotic, neurodegenerative disorders, neurogenic muscular atrophy I, neutropenic fever, non-Hodgkin's lymphomas, abdominal aortic branch occlusion, arterial occlusive disease, OKT3® treatment, orchitis/epididymitis, orchitis/vasectomy reversal operations, organomegaly, osteoporosis, pancreatic graft rejection, pancreatic carcinoma, paraneoplastic disease/tumor-related hypercalcemia, parathyroid graft rejection, pelvic inflammatory disease, perennial rhinitis, pericardial disease, peripheral atherosclerosis (atherlosclerotic) disease, peripheral vascular disease, peritonitis, pernicious anemia, *Pneumocystis carinii* pneumonia, POEMS syndrome (polyneuropathy, organomegaly, endocrinopathy, monoclonal plasma-proliferative disorder and skin changes), postperfusion syndrome, pump head syndrome, post-cardiotomy post-infarction syndrome, preeclampsia, progressive supranuclear paralysis, primary pulmonary hypertension, radiation therapy, Raynaud's phenomenon and disease, Raynoud's disease, Refsum's disease, regular narrow QRS tachycardia, renal vascular hypertension, reperfusion injury, restrictive cardiomyopathy, sarcoma, scleroderma disease, senile chorea, Dementia with Lewy bodies, seronegative arthritis, shock, sickle cell disease, skin allograft rejection, skin changes, small intestinal graft rejection, solid tumors, specific arrhythmias, spinal ataxia, spinocerebellar degradations, streptococcal myositis, cerebellar structural damage, subacute sclerosing panencephalitis, syncope, cardiovascular syphilis, systemic anaphylaxis, a comprehensive systemic inflammatory response syndrome, systemic-onset juvenile rheumatoid arthritis, T cells or FAB ALL, telangiectasia, thrombosis obliterans, thrombocytopenia, toxicity, grafting, trauma/bleeding, hypersensitivity reactions type III, hypersensitivity reactions type IV, unstable angina, uremia, urinary sepsis, urticaria, valvular heart disease, varicose veins, vasculitis, venous diseases, venous thrombosis, ventricular fibrillation, viral and fungal infections, vital encephalitis/aseptic meningitis, vital hemophagocytic syndrome, Wernicke-Korsakoff syndrome, Wilson's disease, heterograft rejection for any organ or tissue, acute coronary syndrome, acute idiopathic polyneuritis, acute inflammatory demyelinating radicular neuropathy, acute ischemia, adult-onset Stills disease, alopecia areata, anaphylaxis, antiphospholipid antibody syndrome, aplastic anemia, coronary sclerosis, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatrical pemphigoid, clinically isolated syndrome (cis) with the risk for multiple sclerosis, conjunctivitis, childhood-onset mental disorders, chronic obstructive pulmonary disease (COPD), dacryocystitis, dermatomyositis, diabetic retinopathy, diabetes mellitus, herniated disk, prolapse of intervertebral disc, drug-induced immune haemolytic anaemia, endocarditis, endometreosis, entophthalmia, episcleritis, erythema multiform, severe erythema multiform, gestational pemphigoid, Guillain-Barre syndrome (GBS), hay fever, Hughes syndrome, idiopathic Parkinson's disease, idiopathic interstitial pneumonia, IgE-mediated allergy, autoimmune hemolytic anemia, inclusion body myositis, infectious ocular inflammatory disease, inflammatory demyelinating disease, inflammatory heart disease, inflammatory kidney disease, idiopathic pulmonary fibrosis/ usual interstitial pneumonia, iritis, keratitis, keratoconjunctivitis sicca, Kussmaul disease or Kussmaul-Meier Disease, Landry palsy, Langerhans' cell histiocytosis, marbled skin, macular degeneration, microscopic polyangiitis, Bechterew disease, motor neuron disease, mucosal pemphigoid, multiple organ failure, myasthenia gravis, spinal cord dysplasia syndrome, myocarditis, nerve root disorders, neuropathy, non-A, non-B hepatitis, optic neuritis, osteolysis, ovarian cancer, oligoarticular JIA, peripheral arterial occlusive disease, peripheral vascular disease, peripheral artery disease (PAD), phlebitis, polyarteritis *nodosa*, polychondritis, polymyalgia rheumatica, poliosis, polyarticular juvenile idiopathic arthritis, multiple endocrine deficiency, polymyositis, polymyalgia rheumatica (PMR), post pump syndrome, primary parkinsonism, prostate and rectal cancer and hematopoietic malignancies (leukemia and lymphoma), prostatitis, pure red-cell aplasia, primary adrenal insufficiency, relapsing neuromyelitis optica, restenosis, rheumatic heart disease, SAPHO (synovitis, acne, pustulosis, hyperstosis and osteitis), sclerodermia, secondary amyloidosis, shock lung, scleritis, ischias, secondary adrenal insufficiency, silicon-associated connective tissue disease, Sneddon-Wilkinson disease, ankylosing spondylitis, Stevens-Johnson syndrome, systemic inflammation response syndrome, cranial arteritis, *Toxoplasma* rhinitis, toxic epidermal necrolysis, transverse myelitis, TRAPS (tumor necrosis factor receptor-associated periodic syndrome), allergic reactions type I, diabetes type II, urticaria, usual interstitial pneumonia, vasculitis, vernal conjunctivitis, viral retinitis, Vogt-Koyanagi-Harada syndrome (VKH syndrome), wet macular degeneration, wound healing, and *Yersinia*- or *Salmonella*-associated arthropathy.

A pharmaceutical composition comprising an antibody that specifically binds human IL-17A can be administered in a therapeutically effective amount to treat an IL-17A-mediated disease or disorder.

An invention suggests a method for the treatment of an IL-17A-mediated disease or disorder using an antibody that specifically binds human IL-17A. The treatment method can involve further administration of TNF-α inhibitors.

Further examples demonstrate the present invention, yet are not intended to limit the present invention to those examples per se.

Description of the present application includes the references to all information sources.

EXAMPLES

Example 1

The Flowchart for Obtainment of VHH-Based Antibodies
FIG. 1 demonstrates the flowchart for obtainment and optimization of VHH-based antibody.

Example 2

Producing Recombinant Antigens and Antibodies in Suspension Mammal Cell Culture

Antibodies and antigens were generated in established cell line obtained from Chinese hamster ovary cells (CHO-K1) according to published protocols [26; 27]. Cells constitutively expressing the gene of EBNA1 protein (Epstein-Barr virus nuclear antigen 1) were used. Suspension culture was conducted in flasks on orbital shaker using serum-free media from Life Technologies Corporation and in accordance with manufacturer's guidelines. For transient expression, cells in a concentration of $2*10^6$/ml were transfected by means of linear polyethyleneimine (PEI MAX, Polysciences). DNA/PEI ratio was 1:3-1:10. In 5-7 days after transfection, cell culture was centrifuged under 2000 g for 20 min and filtered through 0.22 μm filter. Target proteins from culture liquid were isolated by affine HPLC.

Figure 3:
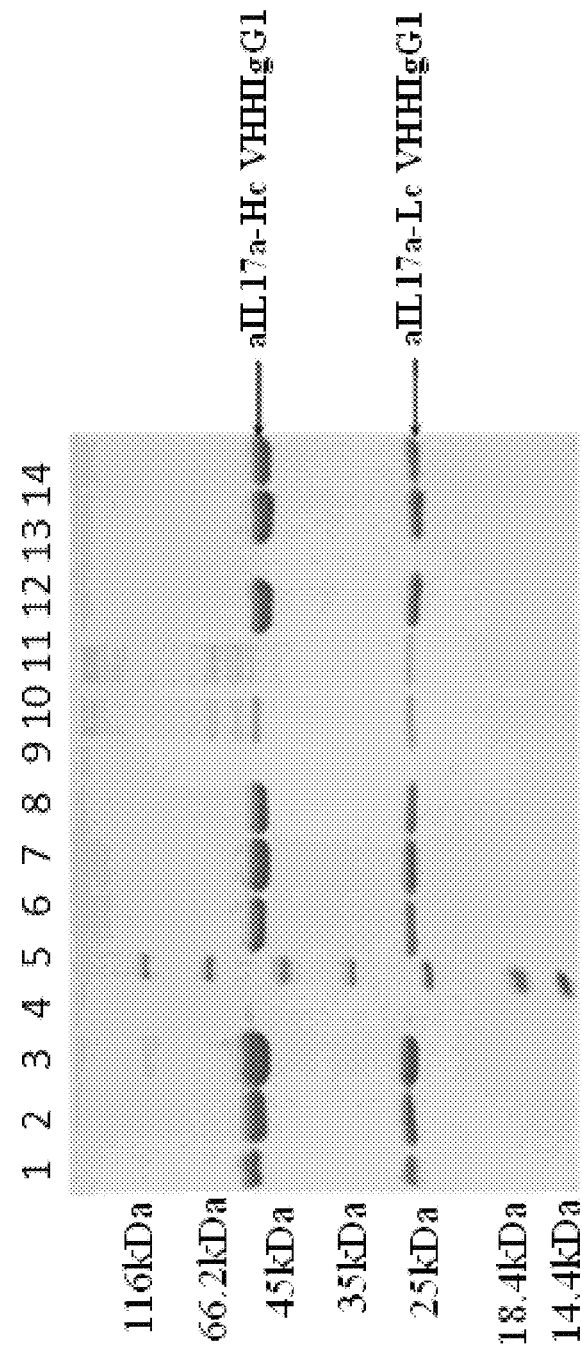
Figure 4:
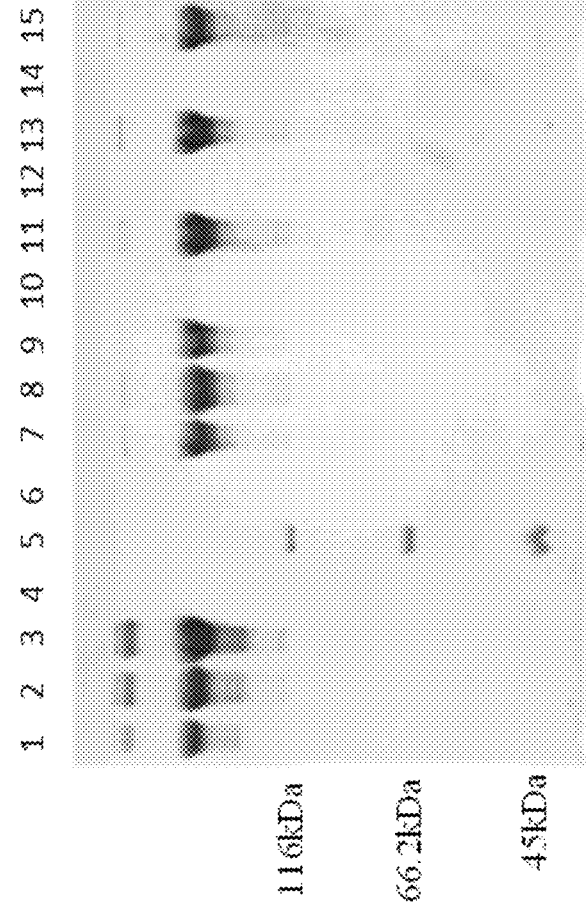

Recombinant IL-17A protein containing 6 His amino acids in C-terminal region was isolated and purified from culture liquid on Profinity IMAC Ni-charged resin (Bio-Rad). Prior to purification procedures, $NiCl_2$ was added to culture liquid to a concentration of 1 mM. Then 5 ml of Profinity IMAC Ni-charged was added to culture liquid and mixed on a shaker for 1 h at room temperature. Sorbent was transferred to 5 ml Thermo scientific Polypropylene columns and washed with column volumes of PBS to remove non-specifically bound components. Bound antigen was eluted with 0.3 M imidazole (pH 8) and 150 mM NaCl. Then the protein was dialyzed into PBS (pH 7.4) by means of SnakeSkin Dialysis Tubing technique, filtered (0.22 m), transferred into tubes and stored at −70° C. Purity of the protein obtained was evaluated by SDS-PAGE (FIGS. 2, 3 and 4).

Test and control IgG1 antibodies were purified on 1 ml Hi Trap rProteinA FF column (GE Healthcare) in accordance with the procedure aforementioned for IL-17A-Fc. Purity of the protein obtained was evaluated by SDS-PAGE (FIGS. 2, 3 and 4).

Example 3

Llama Immunization with Human IL-17A and Generation of Fab-Library of Phage-Displayed Llama Antibodies

*Lama Glama* was immunized 5 times in succession by means of subcutaneous administration of antigen material mixed with an equal volume of complete (first injection) or incomplete Freund's adjuvant (all injections except for the first one). A mixture of recombinant proteins (0.2 mg of each protein per injection) one of which was human IL-17A (Kit from R&D Systems) was used as an antigen. Second injection (immunization stage) was performed 3 weeks after the first one; three more immunizations were performed with a 2-week interval. Blood samples (50 ml) were collected 5 after each injection starting from the third one.

Drawn blood was 2-fold diluted with PBS containing 1 mM EDTA. Then 35 ml of diluted blood were layered over 15 ml of Histopaque®-1077 medium (Sigma, density of 1.077 g/ml) and centrifuged for 20 min under 800 g. Mononuclear cells (lymphocytes and monocytes) were selected from plasma/Histopaque medium interphase zone and washed with PBS containing 1 mM EDTA.

Total RNA from mononuclear llama cells was isolated using RNeasy Mini Kit in accordance with the protocol (QIAGEN). RNA concentration assay was performed using Nanovue (GE Healthcare); the quality of isolated RNA was tested by means of 1.5% agarose gel electrophoresis.

Reverse transcription reaction was conducted using MMLV RT kit (Evrogen) according to the recommended protocol with MMuLV reverse transcriptase and random hexamer primers.

Figure 5:
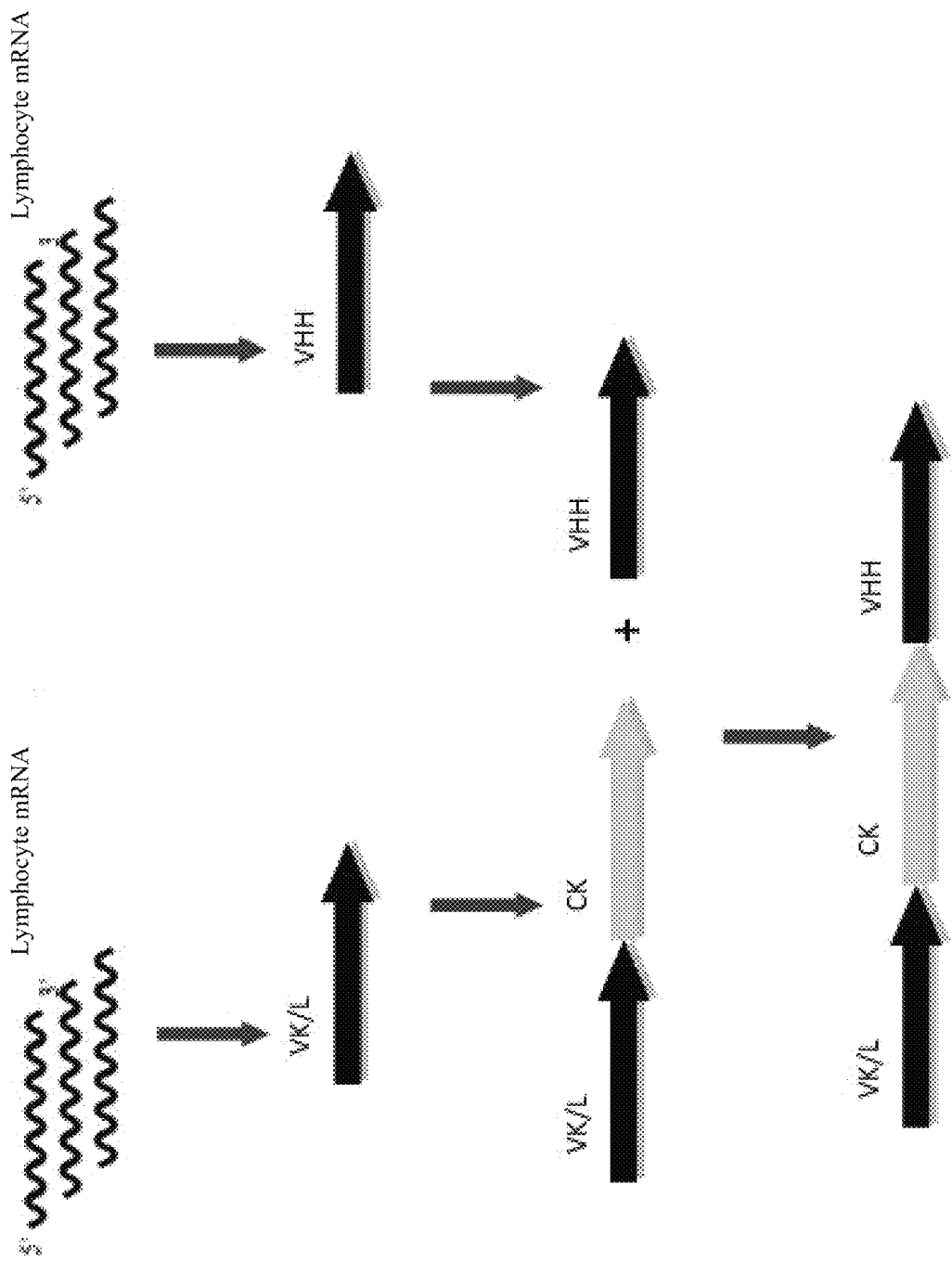
FIG. 5 shows the scheme of the synthesis of llama combinatorial Fab library.
Figure 6:
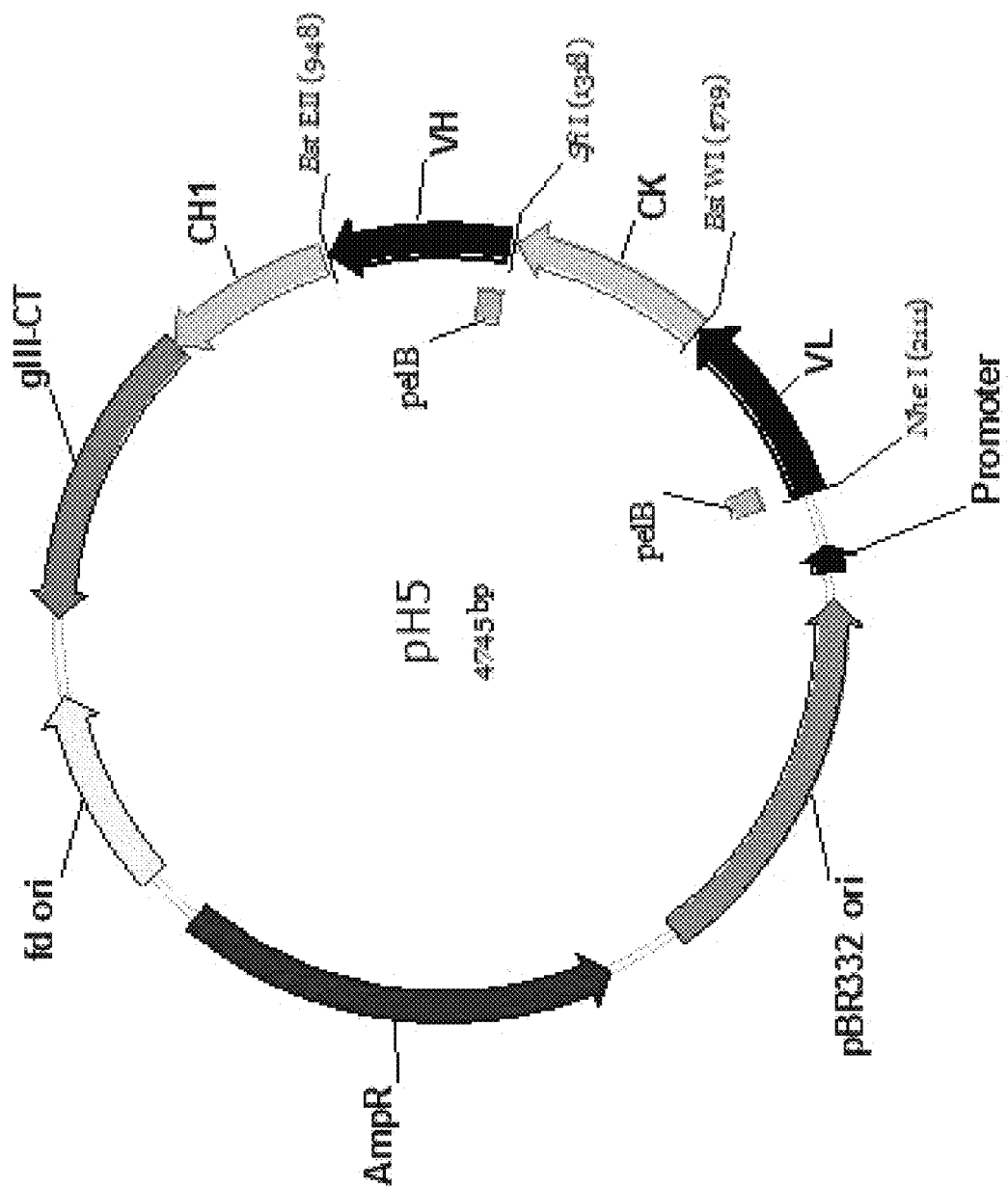
FIG. 6 shows Phagemid for cloning of phage display Fab libraries.

Reverse transcription products were used as a matrix in a two-stage polymerase chain reaction to obtain the genes of variant domains flanked with restriction sites; reaction was performed using oligonucleotide kit and protocols by [27; 28; 29]. Further, genes encoding variable domains of the light and heavy chains were put together in one fragment by means of sequential reactions of restriction, ligation and amplification as shown in FIG. 5. Heavy chain genes were attached separately to kappa and lambda light chain genes. In this case, the estimated count of matrix molecules in all reactions was no less than $10^{11}$. The DNA product obtained (VL-CK-VH) was treated with NheI/Eco91I restriction enzymes and ligated into original phagemid pH 5. Phagemid structure is presented in FIG. 6. Ligation products were transformed into SS320 electrocompetent cells prepared in accordance with protocols [30]. The repertoire of constructed kappa and lambda Fab libraries was $5.1*10^8$ and $3.7*10^8$, respectively. The product of naïve phage-display library was prepared in accordance with the earlier described procedure [31].

Example 4

Selection of Fab-Libraries of Phage-Display Antibodies
Specific anti-IL17A phage-display Fab-antibodies were selected from a phage Fab-display library using a recombinant human IL-17A (a kit from R&D Systems); a series of selection cycles was performed as was described above [27; 31; 32]. To perform the selection process by panning method, human IL-17A in 50 mM carbonate buffer (pH 9.5) was adsorbed overnight at 4° C. on the surface of HighSorb tubes (Nunc). Further, tubes were washed with PBS (pH 7.4)

and then blocked with solution containing PBS (pH 7.4)—fat-free milk (0.5% weight/volume) for 1 hour. Then, 2-4 ml of phage solution ($10^{12}$ phage particles per ml) in PBS (pH 7.4)—fat free milk (0.5% w/vol) were transferred to the tube with the antigen, and the system was incubated for 1 h under stirring. Unbound phages were removed by a series of washing cycles with PBS (pH 7.4)—Tween 20 (0.1% vol./vol.). The number of washing cycles was increased from the first round to the third one—20-30-40 times, respectively. Phage particles that remained bound were eluted with 100 mM Gly-HCl solution (pH 2.5) during 15 min under stirring, and then neutralized with 1 M TRIS-HCl (pH 7.6). E. coli TG1 bacteria were infected with phages obtained; further, phages were isolated and used in the next cycle.

After the second and third round of selection, ELISA performed for the polyclonal phage product has shown the significant enrichment. Pooled clones enriched with human Fab were re-cloned to expression plasmid LL comprising myctag and His6 tag on C-terminus of CHIgene of the heavy chain.

Example 5

Analysis of Fab Specific Binding with Human IL-17A

ELISA was used to measure the binding of studied Fab-fragments with human IL-17A. Fab with published AIN457 sequence (Novartis) was used as a positive control. ELISA plate wells (Nunc ImmunoMaxisorp) were coated with 50 µl (0.5 µg/ml in 1× coating carbonate buffer) IL-17A-Fc, hermetically closed and incubated overnight at 4° C. All further stages were conducted in accordance with the standard ELISA protocol with high-performance systems such as GenetixQ-pix2xt (Molecular Devices) and Tecan Freedom EVO 200 (Tecan). Non-specific binding was blocked by adding the blocking buffer BB (200 µl 0.5% fat-free milk in PBS). Plates were incubated on a shaker for 1 h at room temperature. After washing with PBS-Tween, each cell was coated with 50 µl of test Fab-containing cell supernatant mixed with the equal volume of BB. Plates were incubated on a shaker for 1 hour at room temperature; further, each plate well was 5 times washed with PBS-Tween buffer. After washing, each well was coated (50 µl/well) with anti-human Fab HRP-conjugated secondary antibody (Pierce-ThermoScientific) in PBS-Tween (1:5000). Plates were transferred to rotation shaker (50 min at room temperature) and then 5 times washed with PBS-Tween buffer as described above. Colorimetric signal was obtained by adding TMB (100 µl/well) until saturated (average of 3-5 min); further color development was blocked by adding the stop solution (100 µl/well, 10% sulfuric acid). Absorbance was measured at 450 nm using an appropriate Tecan-Sunrise plate reader (Tecan). Antibody binding was proportional to the signal produced. Those clones for which the color signal exceeded the baseline signal by more than 5 times were tested in competitive ELISA in order to reveal antagonistic Fab blocking the interaction between IL-17A ligand and receptor.

Example 6

Competitive ELISA of Blocking the Interaction of IL17A Ligand and IL17R Receptor Competitive ELISA technique was used to test the antagonistic capacity of previously selected Fab specific against human IL-17A. Fab with published AIN457 sequence (Novartis) was used as a positive antagonist control. Wells ELISA plate (Nunc Immuno Maxisorp) were covered with 50 µl/well IL-17RA-Fc receptor (R&D Systems; 1 µg/ml solution in 1× coating carbonate buffer) and incubated overnight at 4° C. All further stages were performed in accordance with standard ELISA protocols with high-performance systems such as GenetixQ-pix2xt (Molecular Devices) and Tecan Freedom EVO 200 (Tecan). Non-specific binding was blocked by adding the blocking buffer BB (200 µl 0.5% fat-free milk in PBS). Plates were incubated for 1 hour on a shaker at room temperature.

In parallel, 50 µl of test Fab-containing cell supernatant in non-binding 96-well plate were mixed with 50 µl of IL-17A-His6-Flag (0.4 µg/ml in 1% milk diluted with PBS-Tween). The plate was incubated for 1 hour at 37° C. on a shaker under 500 rpm.

After the plate containing IL-17RA-Fc receptor was washed of BB solution, it was coated with the reaction mixture of Fab and IL-17A-His6-Flag in the amount of 90 µl per well. Plates were incubated under shaking for 45 min at room temperature, and each well was 5 times washed with PBS-Tween buffer. Further, 50 µl/well of 1 µg/ml anti-FLAG murine M2 antibody (Sigma) were added, and plates were incubated for 45 min at room temperature. After incubation, each plate well was 5 times washed with PBS-Tween then was coated with 50 µl/well of antimurine-IgG HRP-conjugated secondary antibody (Pierce-ThermoScientific) 1:5000 diluted with PBS-Tween. Plates were incubated on rotation shaker for 45 min at room temperature and 5 times washed with PBS-Tween, as mentioned above. Colorimetric signal was obtained by adding TMB (100 µl/well) until saturated (average of 3-5 min); further color development was blocked by adding the stop solution (100 µl/well, 10% sulfuric acid). Absorbance was measured at 450 nm using an appropriate Tecan-Sunrise plate reader (Tecan). Antibody binding was proportional to the signal produced.

Those clones that demonstrated blocking at the level corresponding to that of control Fab antibody AIN457 were marked as positive and used in further tests. Genes of the variable domains of positive clones were subject to sequencing in accordance with standard protocols on *Applied Biosystems* 3130 Genetic Analyzer (*Applied Biosystems*) followed by appropriate analysis. Clones comprising 3 VHHFab variable domain, corresponding to sequence listings SEQ ID Nos: 11-13 were selected for further studies (FIG. 7, part A). In addition, it was found that 3VHHFab clone is represented in combination with 23 light chain domains of various sequences, three of which are shown in FIG. 7, part B, corresponding to SEQ ID Nos: 14-16. This indicates its relative structural resistance and the fact that VHH domain particularly, rather than the light chain, contributes to IL-17A binding.

Example 7

Comparative $k_{off}(k_{diss})$-Screening of Anti-IL-17A VHHFab Candidates

Comparative $k_{off}$ screening for anti-IL-17A Fab-candidates was performed using Pall Forte Bio Octet Red 96 system. Anti-FABCH1 biosensors were rehydrated for 30 min in a working buffer comprising 10 mM PBS (pH 7.2-7.4), 0.1% Tween-20 and 0.1% BSA. 10× working buffer was added to test samples of *E. coli* supernatants up to 1× final concentration. Then anti-FABCH1 biosensors were steeped into *E. coli* supernatants containing Fab-fragments of candidate antibodies and incubated for 12 hours at a temperature of 4° C. Sensors coated with Fab-fragments were transferred to wells with working buffer, and a baseline was registered (60 sec). Then sensors were transferred to wells with analyte solution (IL-17A, 30 μg/ml) to achieve the antigen-antibody association (300 sec). After that, sensors were returned into wells with working buffer for further dissociation (300 sec). Used sensors were subject to regeneration after each test: they were three times placed into regenerating buffer (Gly-HCl, pH 1.7) and then were applicable for use in further experiments. The curves obtained were analyzed using Octet Data Analysis (version 7.0) according to the standard procedure with 1:1 interaction model.

Figure 8A:
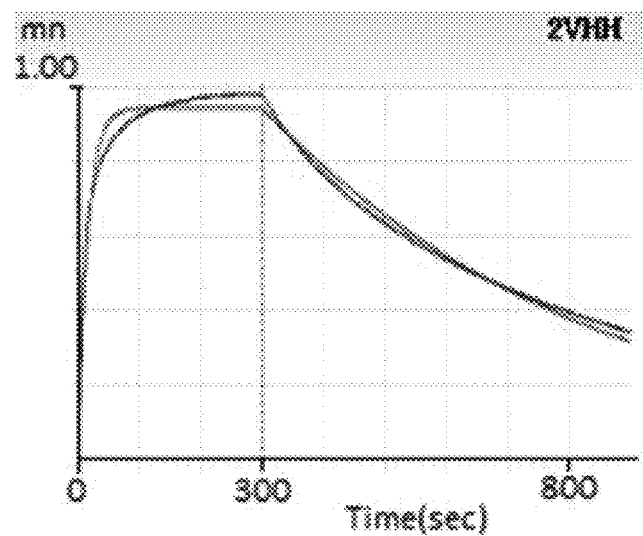
FIGS. 8A-8C show the sensograms for examining the comparative kinetic characteristics of VHHFab clones for binding with IL-17A.
Figure 8B:
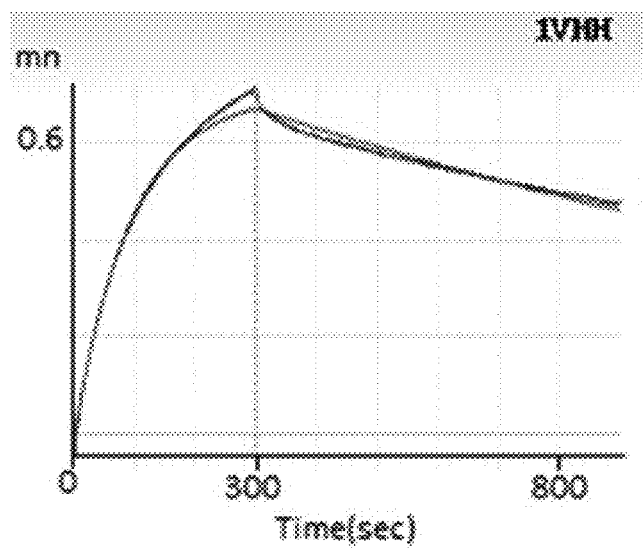
Figure 8C:
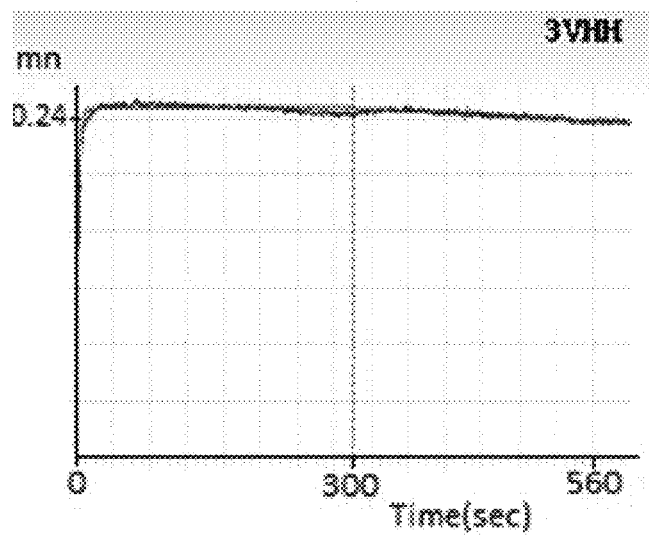

Results obtained for $k_{off}$-screening of anti-IL-17A Fab candidates are presented in FIGS. 8 A-C and Table 1. Specific and high-affinity binding of all unique VHHFab with human IL-17A was demonstrated, wherein 3VHHFab showed very fast $k_{on}$ and very slow $k_{dis}$(l/c) that was beyond the detection limit of the apparatus.

TABLE 1

VHHFab affinity to human IL-17A

| | $K_D$ (M) | $k_{on}$(1/Mc) | $k_{dis}$(1/c) |
|---|---|---|---|
| 1VHH | 2.485E−08 | 2.498E04 | 6.206E−04 |
| 2VHH | 1.352E−08 | 1.628E05 | 2.201E−03 |
| 3VHHVK4B11 | — | — | <2.272E−06 |

Thus, based on the analytical results obtained, 3VHHVK4B11 candidate was selected for further investigation.

Example 8

Generation of VHHIgG1 Antibodies with Mutations in FR1 and FR2 of VHH Variable Domain Genes of the variable domain of the light and heavy VHH chains of 3VHHVK4B1 candidate were cloned in pEE-HcHpEE-Lc plasmid for joint transient expression in CHO-EBNA cells as described in Example 3. Further, substitutions at positions 44 and 45 (Kabat numbering scheme) were introduced by means of oligonucleotide-directed mutagenesis using PfuUltraHS polymerase (Stratagene) in accordance with Protocol [Q5® Site-Directed Mutagenesis Kit (NEB)] and procedure described in [34]. Plasmid pEE-3VHH was used as a matrix. PCR products were fractioned on low-melting agarose and purified on appropriate columns. After ligation, DNA was transformed to *E. coli*. Upon selection of mutant clones with correct sequences, plasmids with mutations in 3VHH were co-transfected with pEE-LcVK4B11 (refer to FIG. 9 and Table 2).

TABLE 2

Samples of 3VHHFabVK4B11 mutant clones

| Name | Mutations compared to initial 3VHHFabVK4B11 |
|---|---|
| mut1 | E44G, R45L |
| mut2 | S11L, E44G, R45L |
| mut3 | R45L |
| mut4 | S11L, E44G |

Example 9

Figure 10A:
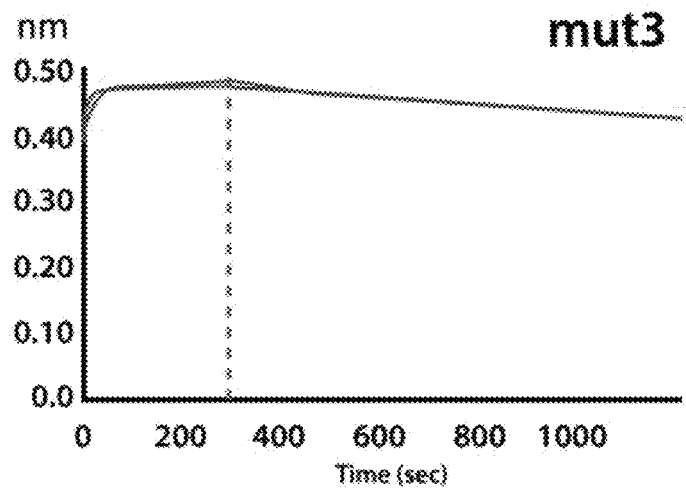
FIGS. 10A-10C and 11A-11B show Aggregation stability of three VHH mutants.
Figure 10B:
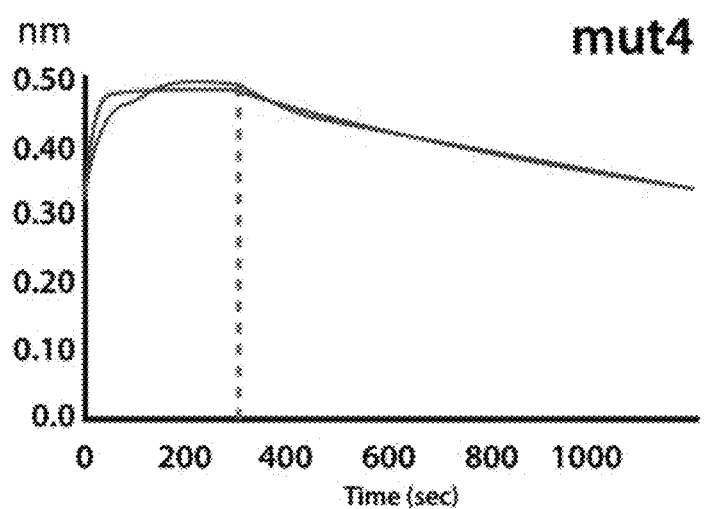
Figure 10C:
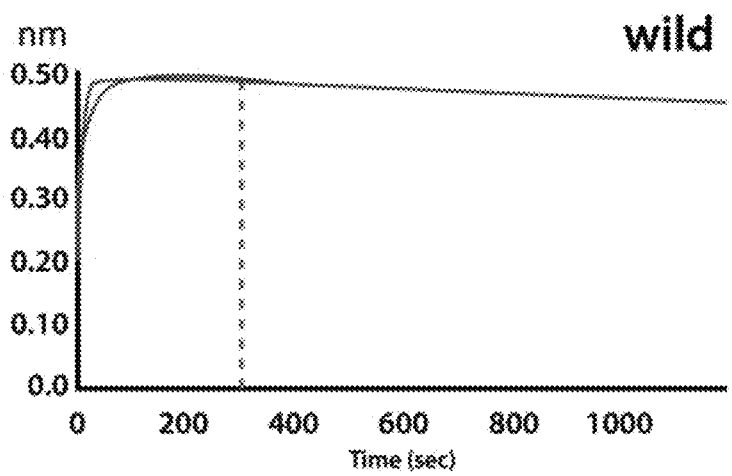
Figure 11A:
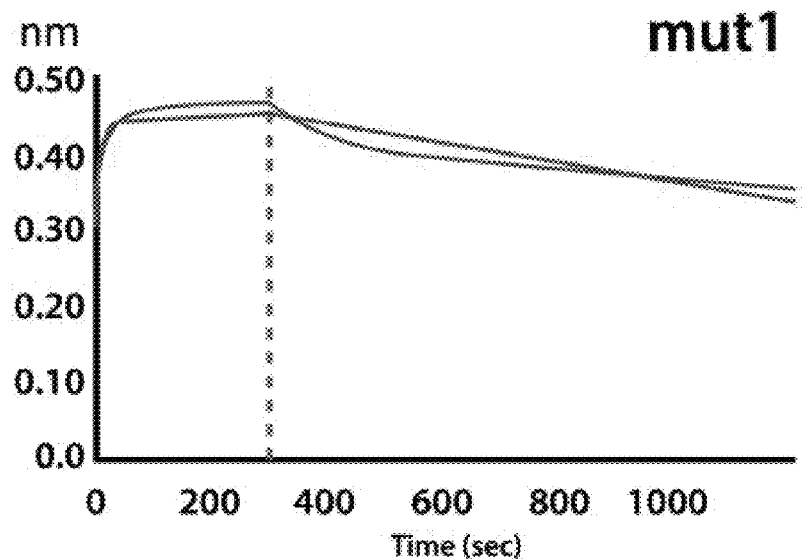
Figure 11B:
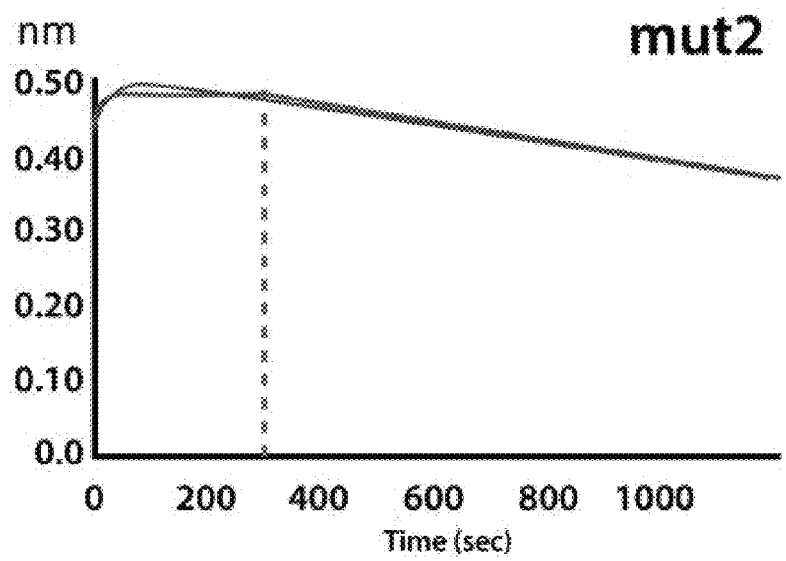

Comparative Analysis of Kinetic Parameters of VHHFab Antibodies Comprising Mutations in FR1 and FR2 of VHH Variable Domain Comparative $k_{off}$ screening for anti-IL-17A VHHFab candidates was performed according to the standard protocol using Pall Forte Bio Octet Red 96 system (refer to Example 8). The significant reduction of $k_{off}$ was found for mut1, mut2 and mut4, and less significant reduction—for mut3, as compared to the native 3VHHFab (FIGS. 10 A-C and 11 A-B).

Example 10

Comparative Analysis of Thermal-Aggregation Characteristics of Full-Size 3VHHIgG1VK4B11 Antibodies Comprising Mutations in FR1 and FR2 of VHH Variable Domain Comparative analysis of aggregation characteristics for anti-IL-17A VHHIgG1 candidates was performed using the following procedure. The preparation of VHHIgG1 antibody (10 mg/ml) in PBS buffer was heated for 6 hours at 50° C. Aggregation induced by thermal stress was evaluated by means of size-exclusion HPLC. The test was performed on 1100 HPLC System (Agilent) using Tosoh TSK-Gel G3000SWXL column, 7.8 mm×30 cm, Cat. No. 08541 with Tosoh TSKgel Guard SWXL pre-column, 6.0 mm×4.0 cm, cm (particles of 7 m, Cat. No. 08543). Isocratic elution with mobile phase containing 50 mM sodium phosphate buffer and 0.3 M NaCl (pH 7.0) was performed under 0.5 ml/min flow rate with the detection at 214 nm and 280 nm wavelengths. Antibody samples were diluted with PBS (pH 7.5) to a concentration of ~1 mg/ml. Injection volume was 10 μl. Gel filtration standard mixture (Bio-Rad, Cat. No. 151-1901) was used to calibrate the column prior to the test.

Figure 12A:
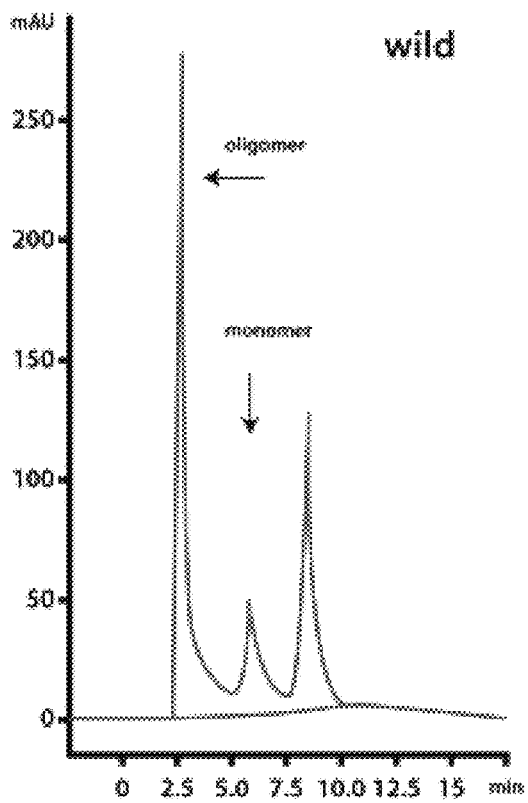
FIGS. 12A-12C and 13A-13B show Affinity of three VHH mutants.
Figure 12B:
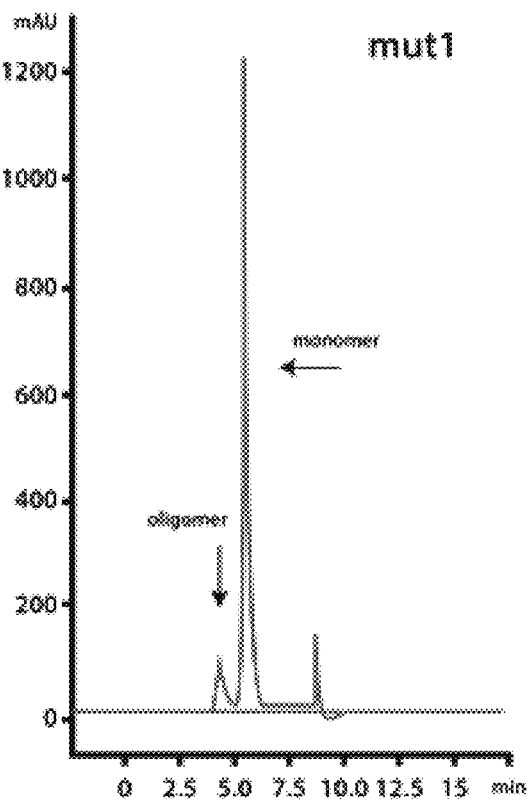
Figure 12C:
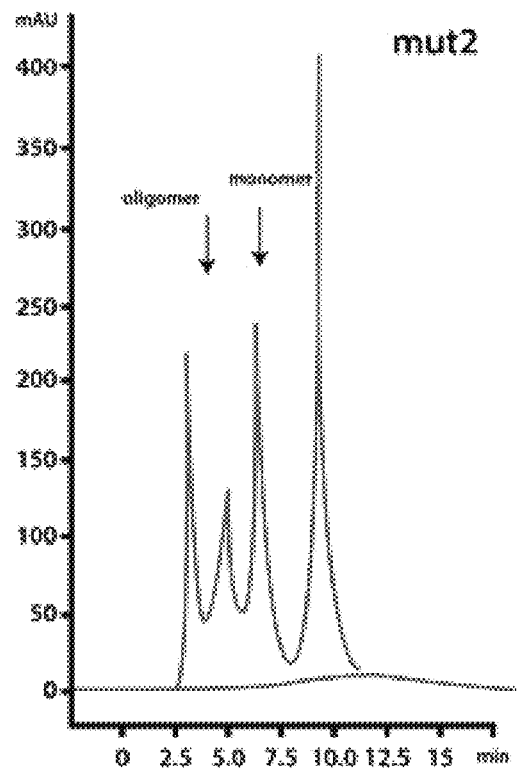

Chromatograms presented in FIGS. 12 A-C and 13 A-B and the summary Table 3 demonstrate that all mutants aggregate to various extents under the thermal stress, wherein the minimum stability was observed for the native variant and the maximum stability was revealed for mut1 comprising E44G+R45L substitutions typical for the classical VH structure.

In addition, comparative study of thermal stability of obtained preparations was performed using Thermofluor procedure (also referred to as Thermal shift assay) that determines the protein melting point measuring the changes in the fluorescence of a specific dye SYPROOrange that binds to hydrophobic surfaces of unfolded protein [35]. StepOneReal-TimePCRSystem (Applied Biosystems) apparatus and recommended protocol were used to study the mutant products. The study results are shown in Table 3. They rather correlate to the results obtained in the thermal stress test, which confirms the stability of mut1 and mut4 in comparison to the wild 3VHHIgG1VK4B 11.

TABLE

Thermal stability study of mutants

| Product | Monomer percentage (%) before thermal stress | Monomer percentage (%) after thermal stress | Difference ~Δ% | Melting point (Thermofluor), ° C. |
|---|---|---|---|---|
| Wild 3VHHIgG1 VK4B11 | 60 | 13 | 47 | 46 ± 1 |
| mut1 | 95 | 95 | 0 | 64 ± 1 |
| mut2 | 65 | 13 | 52 | 42 ± 1 |
| mut3 | 40 | 32 | 8 | ND |
| mut4 | 89 | 80 | 9 | 53 ± 1 |

Example 11

Figure 14:
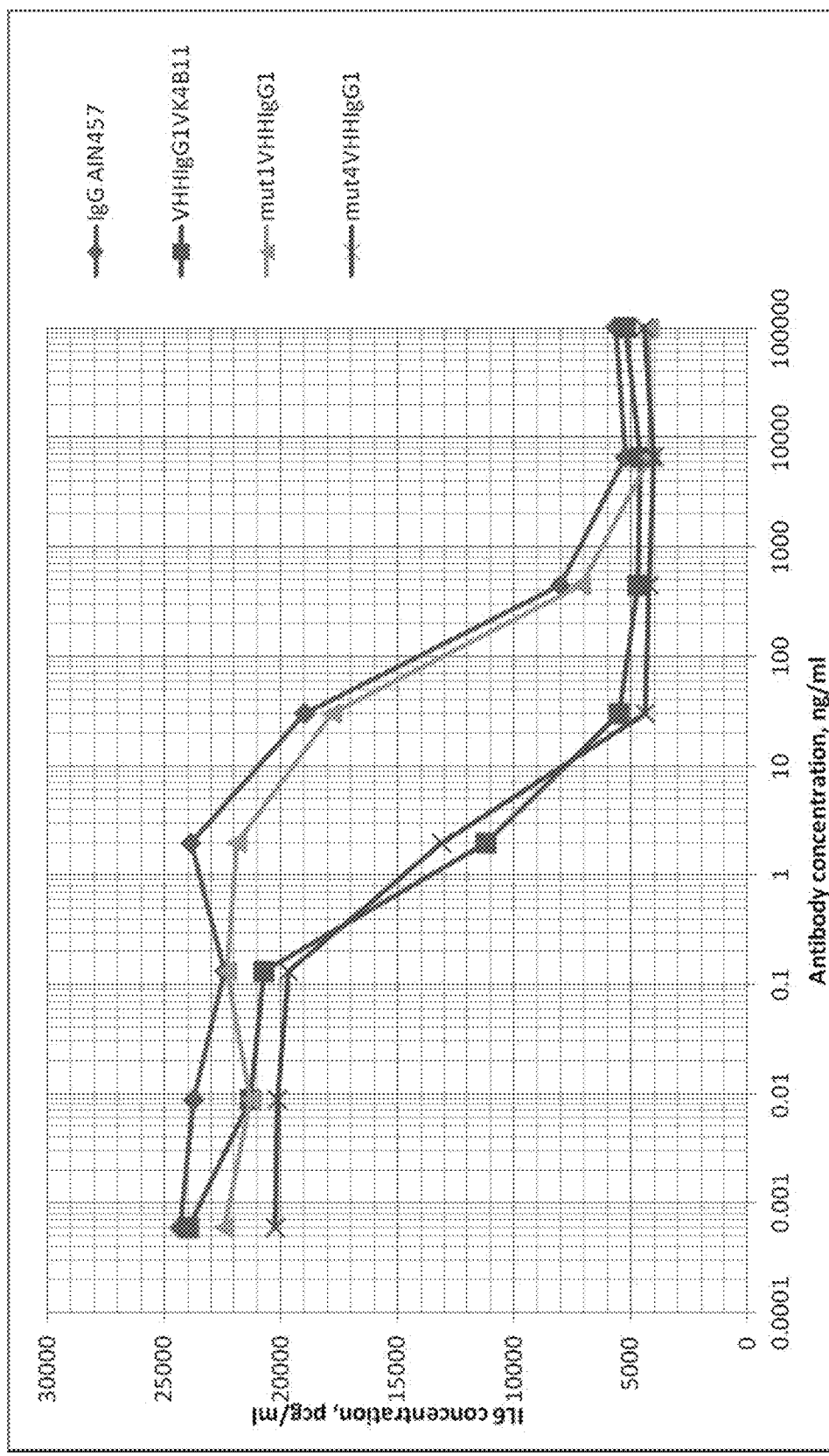
FIG. 14 shows the Cell test for suppression of IL-6 production by inhibiting IL-17A with VHHIgG1VK4B11, mut1VHHIgG1 and mut4VHHIgG1 antagonists.

Cell Test of Anti-IL17A 3VHHIgG1VK4B11 Mutants Blocking the Ability of IL-17A to Induce IL-6 Production The ability of IL-17 to induce the production of IL-6 by human HT1080 cells (ATCC:CCL-121) was used to analyze the neutralizing activity of VHHIgG1 candidates mut1 and mut4 regarding human recombinant IL-17A. Cells were grown on DMEM culture medium with added 10% inactivated fetal serum, gentamycin and glutamine. Aliquots of $5*10^4$ cells/well were seeded in 96-well culture plates. Cells were allowed to adhere for 5 hours. The mixture of 40 ng/ml recombinant IL-17 and 20 ng/ml TNF-α was incubated with VHHIgG1 dilutions for 1 hour at 37° C. Then cytokine/antibody mixture was added to the cells and left overnight. The production of IL-6 by HT1080 cell culture was proportional to the amount of IL-17 added. The amount of released IL-6 in cell supernatant samples was evaluated by ELISA technique using DuoSet ELISA Development System Human IL6 (RD System, Cat. No. DY206). Results obtained from evaluation of antagonistic properties of VHHIgG1 candidates are presented in FIG. 14 in comparison with AIN457 (anti-IL-17A antibody by Novartis). The $IC_{50}$ value for mutt was almost 30 times higher than that for the native variant, while mut4 variant almost completely maintained its inhibiting capacity. The value of $IC_{50}$ for mut4 candidate was 30±10 pM. Based on the results obtained in the present study and the overall physical-chemical and biological characteristics, said candidate was selected for further development and optimization.

Example 12

Engineering of mut4VHHFab Antibodies Comprising Human Light Chains

Total RNA of B-lymphocytes collected from 55 human donors was isolated using RNeasy Mini Kit in accordance with appropriate protocol (QIAGEN). RNA concentration was measured using Nanovue kit (GE Healthcare), and the quality of isolated RNA was tested by 1.5% agarose gel electrophoresis.

Reverse transcription reaction conducted using MMLV RT kit (Evrogen) according to the recommended protocol with MMuLV reverse transcriptase and random hexamer primers.

Figure 15:
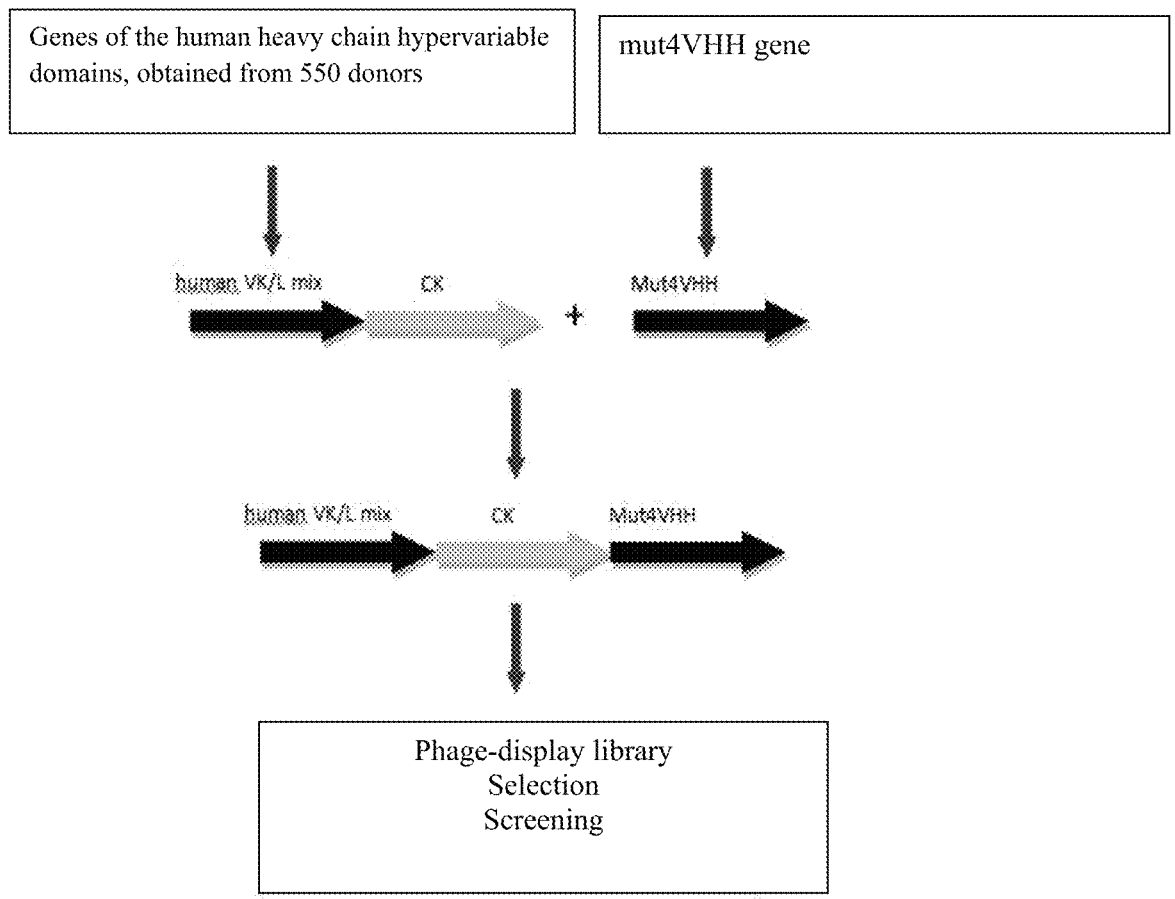
FIG. 15 illustrates isolation of chimeric variants of mut4 VHHFab comprising human light chains.

Reverse transcription products were used as a matrix in a two-stage polymerase chain reaction to obtain the genes of variant domains flanked with restriction sites; reaction was performed using oligonucleotide kit and protocols described in [27]. Chimeric Fab specific against IL-17A were generated according to the procedure described in WO93/06213 based on phagemid pH5, as specified above. Genes encoding variable domains of the human light chains and genes encoding the variable domain of mut4VHH were put together in one fragment by means of sequential reactions of restriction, ligation and amplification as shown in FIGS. 15 and 16. In this case, the estimated count of matrix molecules in all reactions was no less than $10^{12}$. The DNA product obtained (VL-CK-VH) was treated with NheI/Eco91I restriction enzymes and ligated into original phagemid pH 5. Ligation products were transformed into SS320 electrocompetent cells prepared in accordance with protocols described in [30]. The repertoire of chimeric mut4 VHH Fab-library based on mixed kappa and lambda human chains was $2.8*10^9$ transformants. Chimeric phage-displayed Fab-libraries were prepared in accordance with the procedure described above [27].

Selection of phage-displayed chimeric Fab-libraries was performed under the conditions described above (refer to Example 5), except for additional incubation of IL 17A-bound phage antibodies in the presence of 20 µg/ml dissolved IL-17A at a temperature of 37° C. for 12 hours.

After the second round of selection on IL-17A, significant enrichment of the library was observed. Obtained pooled clones of enriched chimeric mut4 VHH Fab-libraries were used in the screening for IL-17A according to the standard protocol (refer to Example 6). Final positive clones were subject to sequencing. FIG. 16 shows four sequences of the variable domains of human light chains VKIA7, CVK3c8, VK3c18 and VK4c1E12 that were combined with high-affinity mut4 VHHFab. These sequences belong to different kappa human germ lines VK1, VK3 and VK4 comprising the minimum number of somatic mutations. It should be noted that human sequence VK4c1E12 shows high homology to the previously selected llama light chain VK4B 1, yet has characteristic distinctions.

Example 13

Comparative Analysis of Thermal-Aggregation Characteristics of Full-Size mut4VHHIgG1 Antibodies Comprising Various Light Chain Variants Genes of the variable domain of the heavy VHH chains of mut4 VHH candidate were cloned in pEE-Hc plasmid, and genes of variable domains of human light chains VK1A7, VK3c18, VK3A4 and VK4E12 were cloned in pEE-Lc plasmid for the joint transient expression in CHO-EBNA cells, as described in Example 3. Further, the obtained antibodies were exposed to the thermal stress and their aggregation profile was investigated as shown in Example 9. Results obtained are presented in a summary tabulation (Table 4).

TABLE 4

Thermal stability of mut4 VHHIgG1 full-size antibodies

| Sample name | Structural family of the light chain | % Monomer before the thermal stress | % Monomer after the thermal stress | Difference ~Δ % | Formation of visible aggregates during the purification | Melting point (Thermofluor) |
|---|---|---|---|---|---|---|
| mut4VHHIgG1VK3c8 | VK3 | 96 | 82 | 14 | + | 58 C. |
| mut4VHHIgG1VK3c18 | VK3 | 91 | 81 | 10 | ++ | 61 C. |
| mut4VHHIgG1VK3A4 | VK3 | 71 | 69 | 2 | + | 61 C. |
| mut4VHHIgG1VK1A7 | VK1 | 95 | 88 | 7 | − | 63 C. |
| mut4VHHIgG1VK4E12 | VK4 | 90 | 49 | 41 | ++ | 59 C. |

In addition, the comparative thermal stability study of products obtained was conducted using Thermofluor procedure similar to that described in Example 11. Based on the data obtained, the conclusion can be made that the selected mut4VHH pairs comprising human light chains were more stable than the native variant comprising VVK4B11 llama light chain. Thus, in the comparative study the best aggregation stability parameters were demonstrated for mut4 VHHIgG1VK1A7 and mut4 VHHIgG1VK3c18 combinations.

Example 14

Cell Test of Blocking the Ability of IL-17A to Induce IL-6 Production Using Mut4 VHHIgG1VK3c8 and Mut4 VHHIgG1VK1A7

Figure 17:
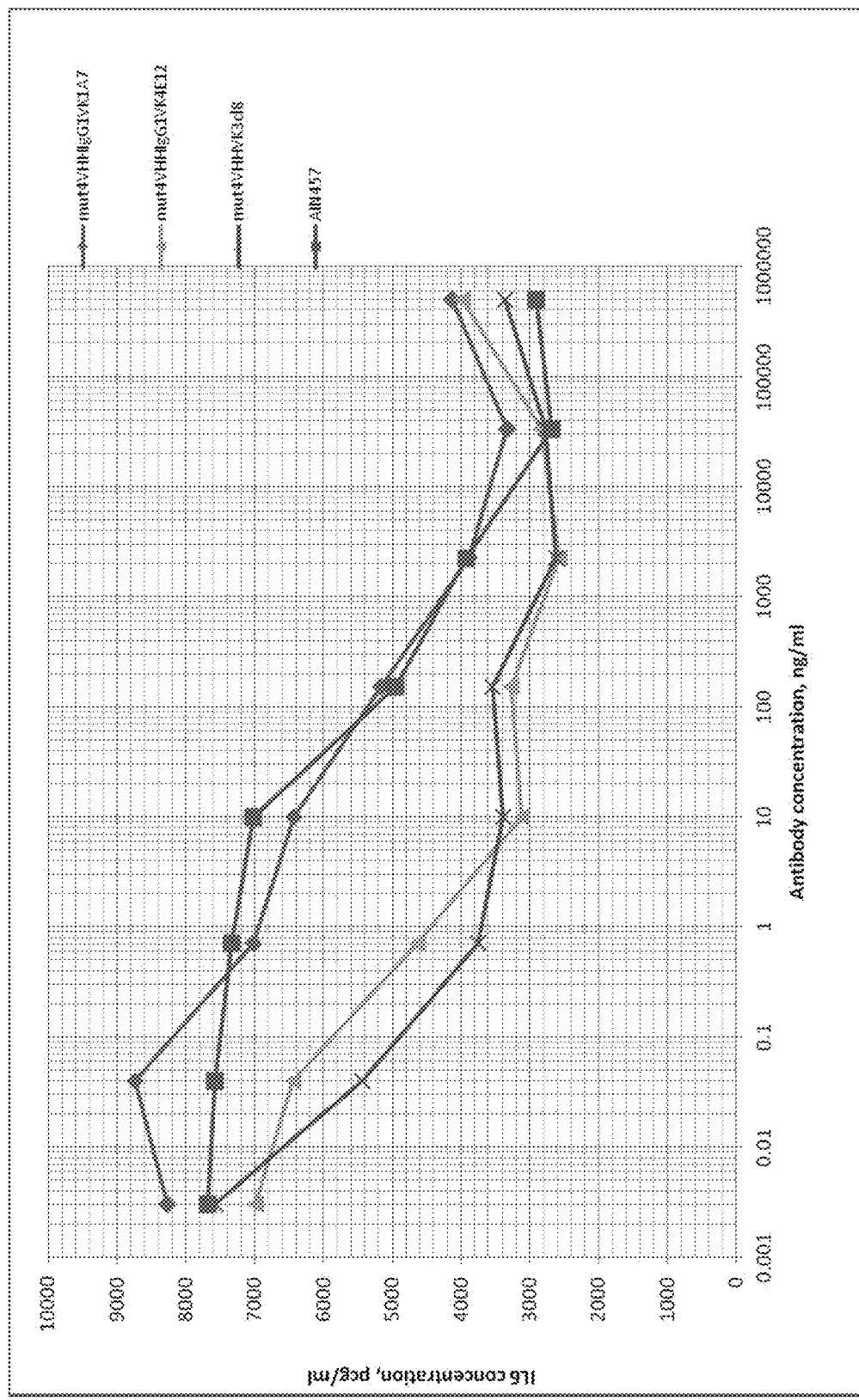
FIG. 17 shows the Cell test for suppression of IL-6 production by inhibiting IL-17A with mut4 VHHIgG1VK3c8, mut4 VHHIgG1VK1A7 and mut4 VHHIgG1VK4E12 antagonists.

The ability of IL-17 to induce the production of IL-6 by human HT1080 cells (ATCC:CCL-121) was used to analyze the neutralizing capacity of VHHIgG1 candidates mut4 VHHIgG1VK3c8 and mut4 VHHIgG1VK1A7 regarding human recombinant IL-17 (refer to Example 12). FIG. 17 shows the results obtained for the blocking test. It should be noted that mut4 VHHIgG1VK1A7 variant (characterized by maximum stability) demonstrated the significant drop of $IC_{50}$ value, while mut4 VHHIgG1VK3c8 variant (medium stability) has demonstrated the inhibition several times exceeding that observed for more stable mut4 VHHIgG1VK1A7 variant.

Example 15

Figure 18:
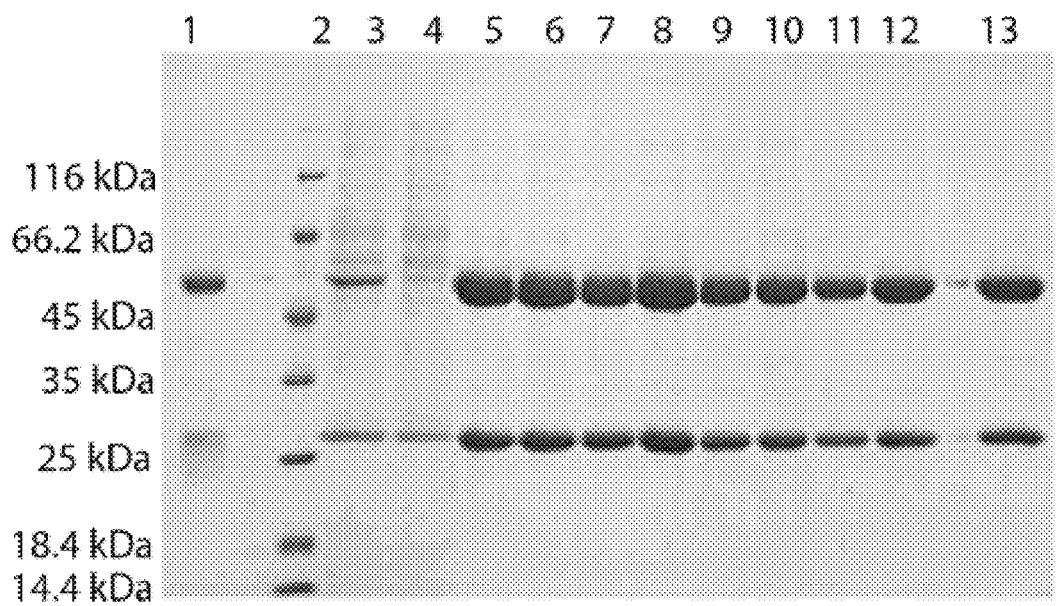
FIGS. 18 and 19 illustrate the Protein electrophoresis under denaturant conditions performed for products comprising antibodies with mutations in positions 44 and 45 of m4 VHHc8.
Figure 19:
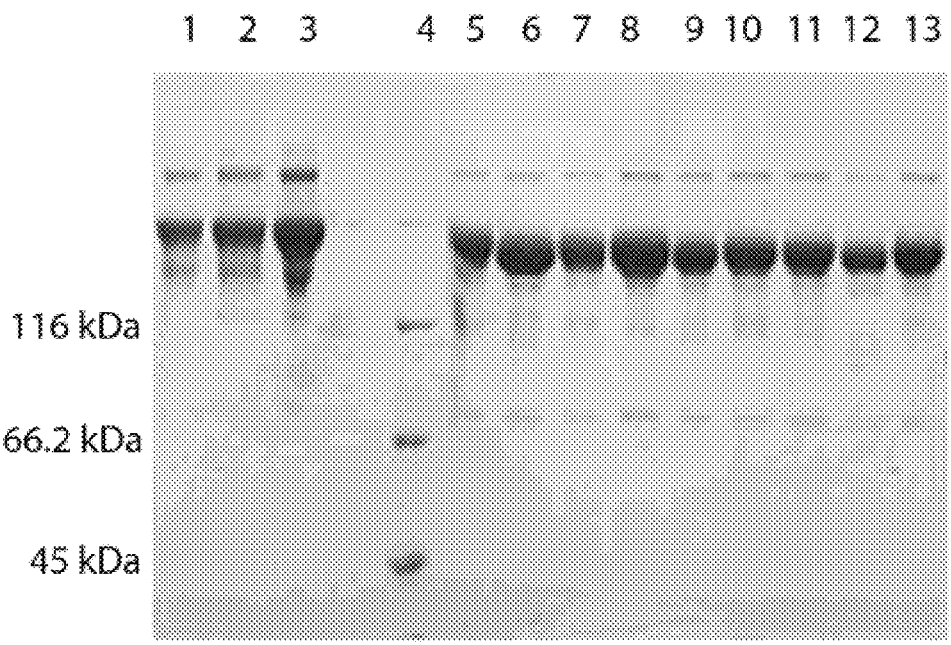

Engineering of Mut4 VHHIgG1 Full-Size Antibodies Comprising Various Mutations at Positions 44 and 45 in FR2 of VHH Variable Domain, and Comparative Analysis of Aggregation and Functional Characteristics Thereof For the purpose of further improvement of the aggregation stability, the method of oligonucleotide-directed mutagenesis was used to introduce substitutions at positions 44 and 45 in the FR2 region of VHH for mut4 VHHIgG1VK3c8 candidate (hereafter referred to as m4VHHc8). The study did not include the variants with aromatic, aliphatic or positive amino acids at position 44, as they are potentially immunogenic and structurally forbidden. Mutants were transiently expressed as described in Example 3 (FIGS. 18 and 19). Yet the amount of the product for different mutants varied from one experiment to another, it should be noted that yields within the same experiment were of comparable size for all substitutions. Obtained mutant variants were exposed to the thermal stress. Table 5 demonstrates the results obtained for different mutants. It can be seen that the less stable mutants are 44G45G and 44G45D the stability of which is lower than that for the initial 44G45R combination within m4VHHc8. Such variants as 44G45N, 44V45T, 44D45T, 44T45T and 44D45V significantly remained their stability. All other combinations demonstrated the adding effect that resulted in the increased aggregation stability ofm4VHHc8, and the most stable were the variants comprising aromatic or aliphatic groups at position 45. However, the variants comprising small hydrophilic and hydrophobic amino acids at both positions, such as 44G45V, 44G45T, 44V45V, 44A45V, 44T45V, 44A45T and 44S45T, has also demonstrated the significant stability.

TABLE 5

Results obtained for the transient expression and thermal stress study of mutants comprising substitutions at positions 44 and 45 of FR2 region ofm4VHHc8.

| No. | Mutant at position 44 + 45 of FR2 region of m4VHHc8 | | Monomer. initial* | Monomer. %, heated* | ~Δ % | Production yield for the product ** (номер эксперимента) ≈, mg/L | IC50, picomole***as defined by the cell IL6 test |
|---|---|---|---|---|---|---|---|
| 1 | 44G | 45R | 96 | 81 | 15 | 41 (1) | 50 |
| 2 | 44G | 45F | 98 | 98 | 0 | 22 (3) | 1100 |
| 3 | 44G | 45W | 97 | 97 | 0 | 57 (2) | 1200 |
| 4 | 44G | 45Y | 97 | 97 | 0 | 33 (2) | 650 |
| 5 | 44G | 45P | 98 | 98 | 0 | 41 (1) | 800 |
| 6 | 44G | 45I | 97 | 97 | 0 | 20 (3) | 950 |
| 7 | 44G | 45 L | 97 | 97 | 0 | 25 (3) | 1000 |
| 8 | 44G | 45G | 96 | 50 | 46 | 21 (3) | ND |
| 9 | 44G | 45N | 90 | 77 | 13 | 26 (2) | ND |
| 10 | 44G | 45S | 93 | 85 | 8 | 45 (2) | 100 |
| 11 | 44G | 45D | 90 | 40 | 50 | 23 (3) | ND |
| 12 | 44G | 45A | 93 | 89 | 4 | 27 (3) | 100 |
| 13 | 44G | 45H | 93 | 93 | 2 | 25 (3) | 150 |
| 14 | 44G | 45V | 93 | 93 | 0 | 35 (1) | 250 |
| 15 | 44G | 45Q | 91 | 84 | 7 | 36 (1) | ND |
| 16 | 44G | 45T | 93 | 93 | 0 | 46 (1) | 100 |
| 17 | 44V | 45T | 95 | 84 | 11 | 64( 4) | ND |
| 18 | 44D | 45T | 95 | 83 | 12 | 72 (4) | ND |
| 19 | 44T | 45T | 96 | 86 | 10 | 75 (4) | 150 |
| 20 | 44A | 45T | 95 | 93 | 2 | 74 (4) | 150 |
| 21 | 44S | 45T | 96 | 94 | 2 | 63 (4) | 150 |
| 22 | 44V | 45V | 95 | 95 | 0 | 71 (4) | 150 |
| 23 | 44D | 45V | 96 | 88 | 12 | 28 (4) | 150 |
| 24 | 44A | 45V | 95 | 95 | 0 | 72 (4) | 100 |
| 25 | 44T | 45V | 96 | 95 | 1 | 73 (4) | 150 |
| 26 | AIN457 | | 95 | 95 | 0 | 0 | 1100 |

*Error in different batches is up to 5%
** Varies significantly depending on the experiment; more correct comparison is provided for products within the same batch
***Error in different batches is up to 50%

Figure 20A:
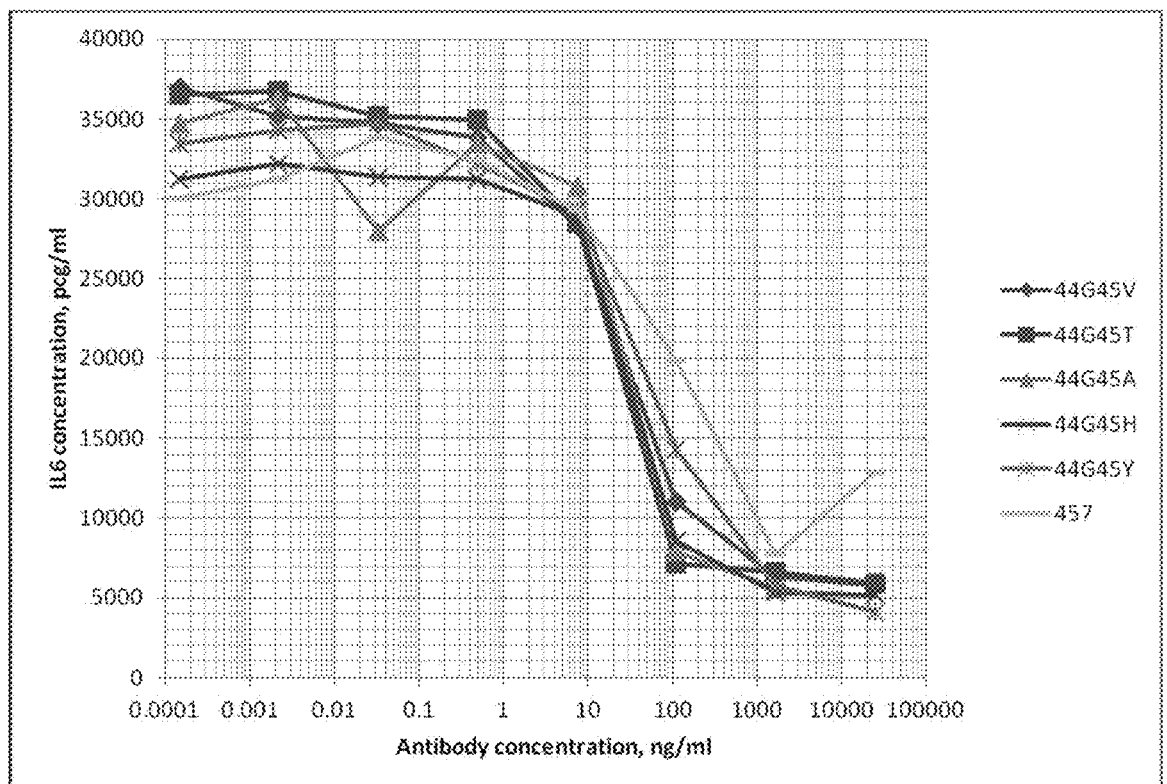
FIGS. 20A-20B show the Comparative cell test for suppression of IL-6 production by inhibiting IL-17A with m4VHHc8 antagonists comprising mutations in FR2 at positions 44 and 45.
Figure 20B:
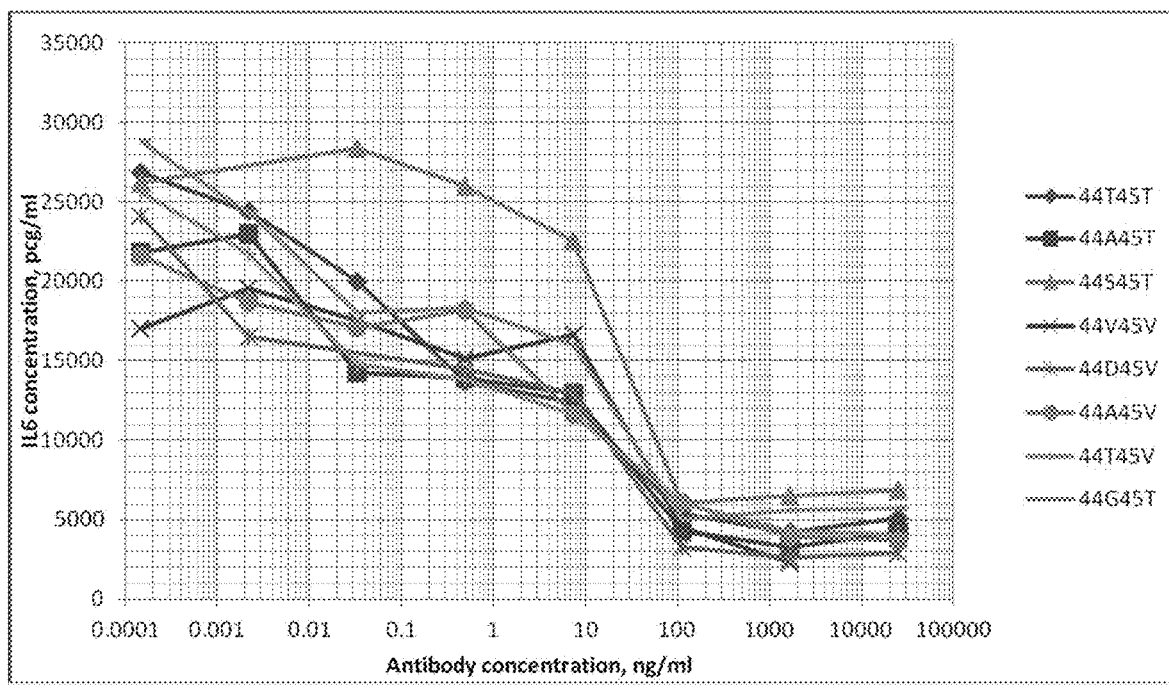
Figure 21:
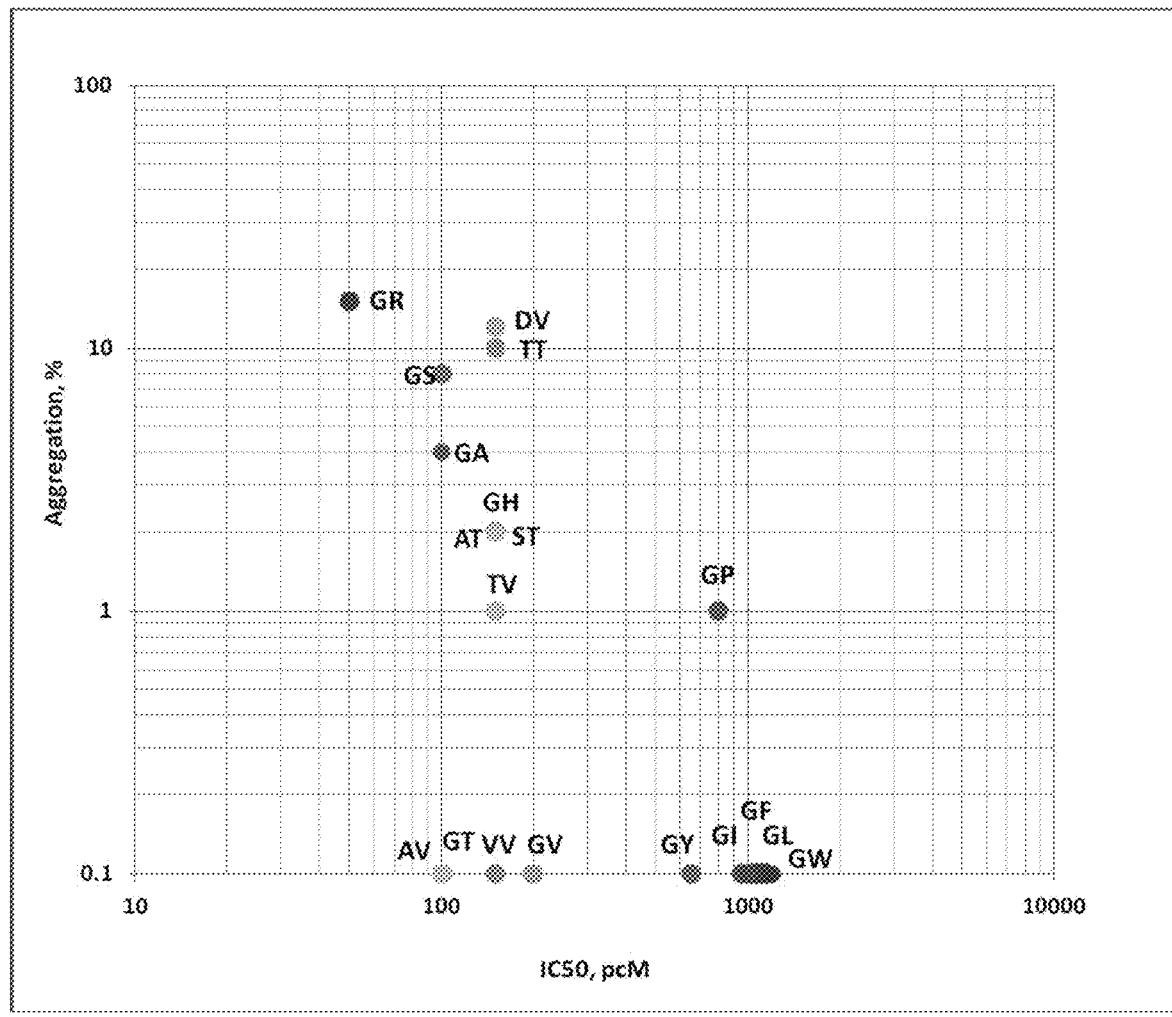
FIG. 21 illustrates Diagram showing the stability and functional properties of different mutations at positions 44 and 45 in FR2 of m4VHHc8 that determine the interaction of the light and heavy chain variable domains. Dashed thick lines correspond to the combinations providing the maximum balanced aggregation stability and functional activity values; Dashed thin lines correspond to the suitable aggregation stability values with the high affinity remained.
Figure 22:
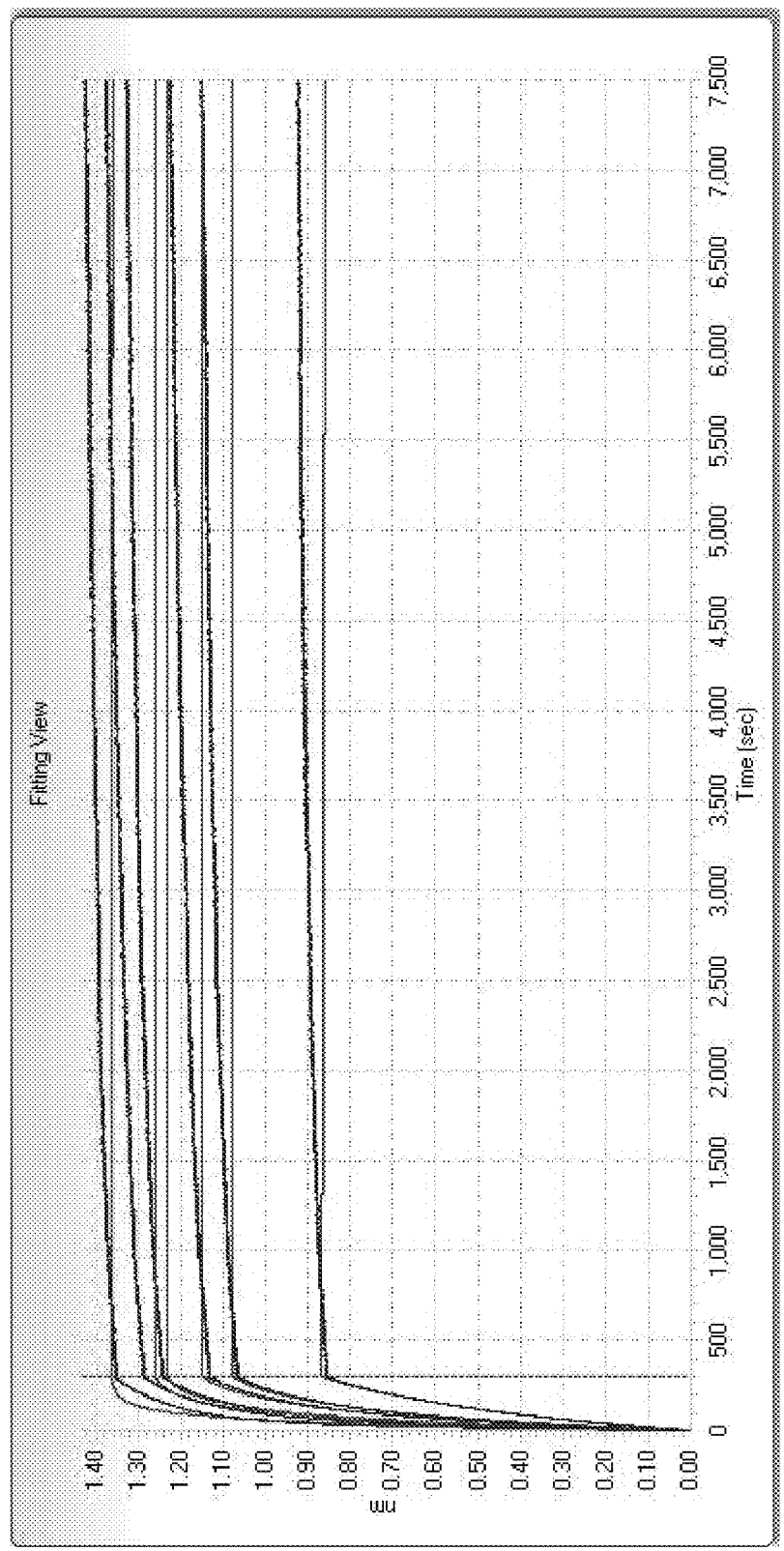
FIG. 22 shows the Determination of kinetic parameters of BCD109 interaction with IL-17A of various origins.

To evaluate the neutralizing activity in the cell test as described in Example 12, experiments were performed with various mutants (FIGS. 20A and 20B). Test results are shown in Table 5. It was shown that the small amino acids at VHH FR2 positions 44 and 45 demonstrated high antagonistic activity, while the large ones (aliphatic and aromatic) introduced at position 45 resulted in 10-fold reduction of $IC_{50}$. FIG. 21 presents the diagram of stability and functional properties for mutants comprising various amino acid substitutions that determine the interaction of the variable domain of the heavy and light chains.

Example 16

Scanning Mutagenesis of CDRs antiIL17A 3VHH Domain

Mutations to individual positions of candidate's CDRs were inserted by means of NNK randomization technique [26] using Q5® Site-Directed Mutagenesis Kit (NEB) in accordance with the protocol. Plasmid pLL-Fab was used as a matrix. PCR products were fractioned on low-melting agarose and purified on appropriate columns. After ligation, DNA was transformed to *E. coli* expression strain BL2 gold (Stratagene). The individual clones obtained were then gained by Fab expression in 96-well plates, as described above. Supernatants containing mutant Fab arms were analyzed by ELISA under the conditions described above and using the high-performance Genetix Q-pix2xt and Tecan Freedom EVO200 systems. The concentration of immobilized IL-17A was 0.2 µg/ml. Bound Fab arms were stained with 1:5000 diluted Goat anti-Human IgG (Fab')2 (HRP)

conjugate (Pierce) and TMB+H2O2/H2SO4 dye; absorption was measured at 450 nm wavelength.

Results obtained by scanning mutagenesis are presented in Table 6. The Table shows within-CDR substitutions that correspond to ≤30% reduction of mutant Fab/human Il-17A binding signal when compared to the wild type sequence. Thus, such individual mutants or any combinations thereof are the field of the invention.

TABLE 6

Scanning mutagenesis

| Mutation position | Positive amino acids in mutants |
|---|---|
| HCDR3 | |
| V94 | S, T, A, K, D, G |
| R95 | K |
| R96 | Y, H, W, K, D, G |
| R97 | A, L, M, S, H, V |
| F98 | — |
| D99 | E, G, A, R, V, K, Q |
| G100 | N, S |
| T100a | G, P, V, R, S, N, K |
| S100b | V, M, T, L, T, A, H, G, I, C |
| Y100c | W, S |
| Y100d | R, L, W, K, A, G, Q, I, V |
| T100e | A, L, S |
| G100f | A, L, T, P, N, Q, F, I, D |
| D107 | — |
| HCDR2 | |
| A50 | G, L |
| S52 | — |
| P52a | A |
| S53 | — |
| G54 | — |
| G55 | S, R, P, D, I, T, E, K, A, L |
| D56 | — |
| R57 | — |
| I58 | — |
| HCDR1 | |
| S32 | N, K, R, E, W, M, Q, D, F, V, L, A |
| P33 | S |
| M34 | I |
| G35 | L, A, I, S, R, V, N, Q, M |

Thus, the screening was performed for BCD109 antibody CDR amino acid positions that are tolerant to amino acid substitutions. It was demonstrated that the present panel of amino acid substitutions does not significantly change the antibody affinity to human IL-17A. Said substitution panel can be used to improve various properties of the candidate.

Example 17

Engineering of BCD109 Candidate and Evaluation of its Affinity to IL-17A of Various Origins BCD109 antibody was obtained from m4VHHc8 variant comprising 44G45T substitutions (described in Example 16) by introducing humanizing mutations Q5V and R89V to VHH that do not change either the stability or IC$_{50}$ (no data provided), and three additive mutations in CH2 domain FcIgG1, 232Y/234T/236E, intended to improve the antibody pharmacokinetics. The antibody has been transiently expressed.

The affinity of BCD109 binding to human, monkey and rat IL-17A was investigated on OctetRed 96 system (ForteBio). BCD109 was non-specifically immobilized on the surface of amine reactive second-generation sensors (AR2G) according to the standard protocol described in the manufacturer's manual. The test was conducted at a temperature of 30° C. and using PBS with 0.1% Tween-20 and 0.1% BSA as a working buffer.

Human, monkey and rat IL-17A was titrated with the working buffer from a concentration of 126 nM to 2 nM with an increment of 2.

Figures 13A, 13B:
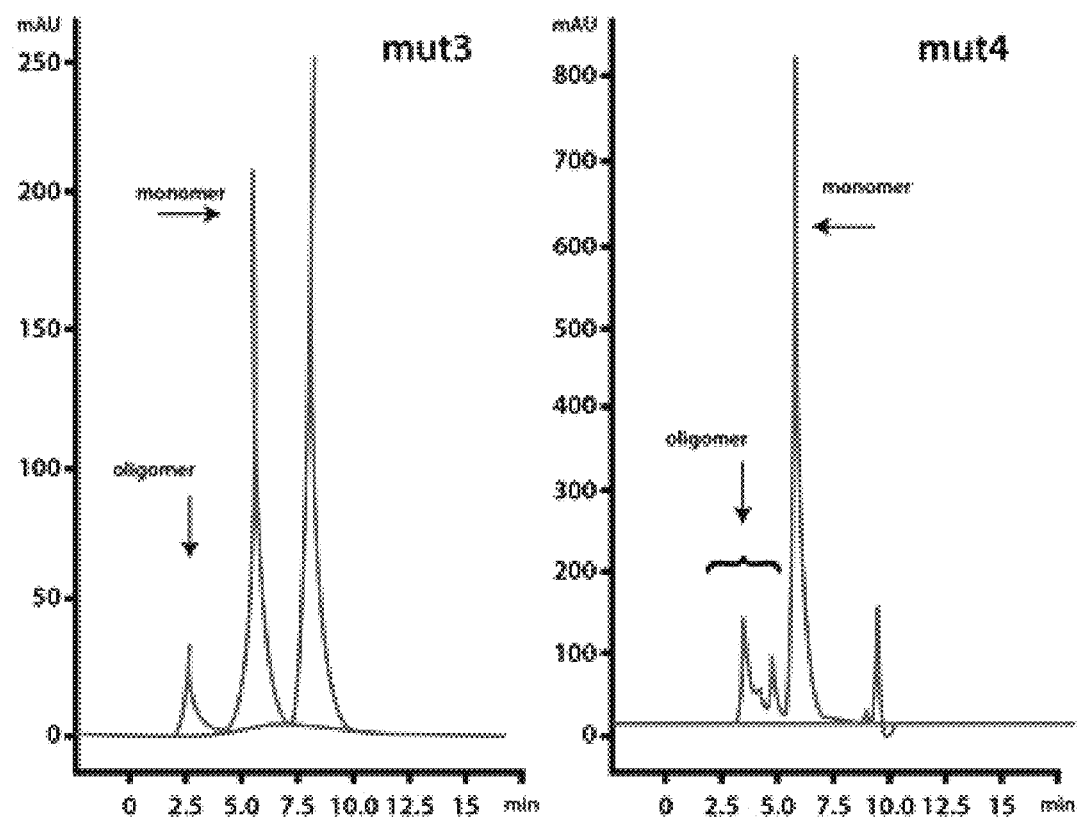

Binding curves (after subtracting a reference signal) were analyzed using Octet Data Analysis software (Version 7.0) in accordance with the standard procedure and using 1:1 interaction model. The results are presented in FIG. 13A.

It can be seen that BCD109 binds to human and monkey IL-17A with picomolar affinity (FIGS. 23A and 23B). Moreover, the candidate does not interact with rat IL-17A (no curves are presented).

Example 18

Determination of the Aggregation Stability of BCD109 Under Thermal Stress

BCD109 preparation of 10 mg/ml in PBS was heated for 6 hours at a temperature of 50° C. in accordance with the protocol described in Example 9.

Figure 24:
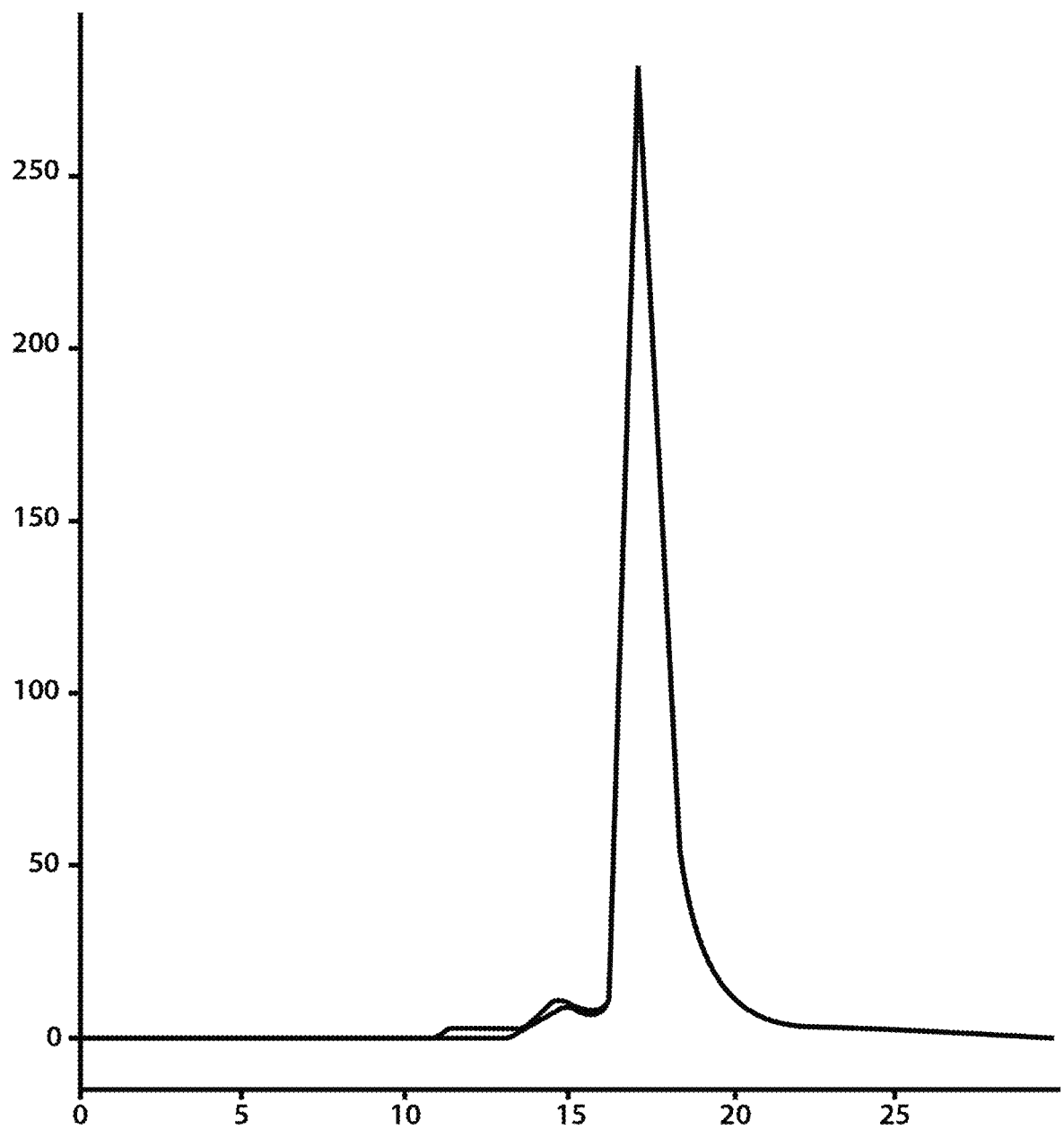
FIG. 24 shows Chromatogram of BCD109 antibodies obtained before and after the thermal stress. "a" is the chromatographic profile obtained with the antibody before heating and "b" is the chromatographic profile obtained with the antibody after heating. Protein concentration were aligned and equaled 10 mg/mL in PBS.

Results represented in FIG. 24 show that BCD109 antibody remains stable under thermal stress: aggregate content was less than 5%.

Example 19

Obtainment of a Pharmaceutical Composition Comprising the Antibody of the Invention BCD109 antibody in a concentration of 50 mg/ml was dissolved in q.s. water for injection and pH was brought to 5.5 with citric acid. Solution was filtered (filtration sterilization) and sealed into ampoules.

The product obtained was stable for 6 months with no sedimentation.

Alternatively, BCD109 was dissolved in water containing mannitol as a lyoprotectant, filtered (filtration sterilization) and then subject to freeze-drying. The powder obtained was dispensed to sterile vials. Vials were corked with rubber stoppers and sealed with aluminum caps. The antibody product can be recovered from the lyophilizate with water for injection.

REFERENCES

1. Porter R. R. 1973. Structural studies of immunoglobulins. *Science*. 180, 713-716.
2. Padlan E. A. 1994. Anatomy of the antibody molecule. *Mol. Immunol*. 31, 169-217.
3. Dwek R. A., Sutton B. J., Perkins S. J., Rademacher T. W. 1984. Structure-function relationships in immunoglobulins. *Biochem. Soc. Symp*. 49, 123-136.
4. Burton D. R. 1985. Immunoglobulin G: functional sites. *Mol. Immunol*. 22, 161-206.
5. Hamers Casterman C., Atarhouch T., Muyldermans S., Robinson G., Hamers C., Bajyana Songa E., Bendahman N., Hamers R. 1993. Naturally occurring antibodies devoid of light chains. *Nature*. 363, 446-448.
6. S. V. Tillib *Molecular Biology*, 2011, 45, No. 1, 77-85. Camel nanlantibodies—efficient instrument for investigations, diagnostics and therapy.
7. Nguyen V. K., Hamers R., Wyns L., Muyldermans S. 1999. Loss of splice consensus signal is responsible for the removal of the entire CH1 domain of the functional camel IGG2A heavy-chain antibodies. *Mol. Immunol*. 36, 515-524.

8. Woolven B. P., Frenken L., van der Logt P., Nicholls P. J. 1999. The structure of the llama heavy chain constant genes reveals a mechanism for heavy-chain antibody formation. *Immunogenetics.* 50, 98-101.
9. Nguyen V. K., Hamers R., Wyns L., Muyldermans S. 2000. Camel heavy-chain antibodies: diverse germline VHH and specific mechanisms enlarge the antigen-binding repertoire. *EMBO J.* 19, 921-931.
10. De Genst E., Saerens D., Muyldermans S., Conrath K. 2006. Antibody repertoire development in camelids. *Develop. Comp. Immunol.* 30, 187-198.
11. Muyldermans S., Cambillau C., Wyns L. 2001. Recognition of antigens by single-domain antibody fragments: the superfluous luxury of paired domains. *TIBS.* 26, 230-235.
12. De Genst E., Silence K., Decanniere K., Loris R., Kinne J., Muyldermans S. 2006. Molecular basis for the preferential cleft recognition by dromedary heavy chain antibodies. *Proc. Natl. Acad. Sci. USA.* 103, 4586-4591.
13. Kabat E., Wu T. T., Perry H. M., Gottesman K. S., Foeller C. 1991. Sequence of proteins of immunological interest. *US Public Health Services.* NIH, Bethesda, Md., Publication no. 91-3242.
14. Nguyen V. K., Desmyter A., Muyldermans S. 2001. Functional heavy-chain antibodies in camelidae. *Adv. Immunol.* 79, 261-296.
15. Muyldermans S., Baral T. N., Retamozzo V. C., et al. 2009. Camelid immunoglobulins and nanobody technology. *Vet. Immunol. Immunopathol.* 128 (1-3), 178-183.
16. de Genst E., Silence K., Decanniere K., Loris R., Kinne J., Wyns L., Muyldermans S. 2005. Strong in vivo maturation compensates for structurally restricted H3 loops in antibody repertoires. *J. Biol. Chem.* 280, 14114-14121.
17. Lauwereys M., Ghahroudi M., Desmyter A., Kinne J., Holzer W., De Genst E., Wyns L., Muyldermans S. 1998. Potent enzyme inhibitors derived from dromedary heavy chain antibodies. *EMBO J.* 17, 3512-3520.
18. Kontermann R E. 2009 Strategies to extend plasma half-lives of recombinant antibodies. BioDrugs.; 23(2): 93-109.
19. Ken Coppieters, Torsten Dreier, Karen Silence, Hans de Haard, Marc Lauwereys, Peter Casteels, Els Beirnaert, Heidi Jonckheere, 2006 Formatted anti-tumor necrosis factor alpha VHH proteins derived from camelids show superior potency and targeting to inflamed joints in a murine model of collagen-induced arthritis Arthritis & Rheumatology; 54(6): 1856-66.
20. Gabrielle Richard, Ashley J Meyers, Michael D McLean, Mehdi Arbabi-Ghahroudi, Roger MacKenzie, J Christopher Hall 2013. In Vivo Neutralization of a-Cobratoxin with High-Affinity Llama Single-Domain Antibodies ($V_HHs$) and a $V_H$-Fc Antibody. PLoS One 22; 8(7): e69495.
21. Jan Terje Andersen, Maria Gonzalez-Pajuelo, Stian Foss, Ole J. B. Landsverk, Debora Pinto, Alexander Szyroki, Hans J. de Haard, Michael Saunders, Peter Vanlandschoot Inger Sandlie 2012, Selection of Nanobodies that Target Human Neonatal Fc Receptor. *Scientific Reports,* 3, 1118.
22. Vincke C[1], Loris R, Saerens D, Martinez-Rodriguez S, Muyldermans S, Conrath K. 2009 General strategy to humanize a camelid single-domain antibody and identification of a universal humanized nanobody scaffold. J Biol Chem. January 30; 284(5): 3273-84.
23. Barthelemy P A, Raab H, Appleton B A, Bond C J, Wu P, Wiesmann C, Sidhu S S. 2008 Comprehensive analysis of the factors contributing to the stability and solubility of autonomous human VH domains. J Biol Chem. February 8; 283(6):3639-54.
24. Conrath K, Vincke C, Stijlemans B, Schymkowitz J, Decanniere K, Wyns L, Muyldermans S, Loris R. Antigen binding and solubility effects upon the veneering of a camel VHH in framework-2 to mimic a VH. J Mol Biol. 2005 Jul. 1; 350 (1): 112-25.
25. Hermeling S, Crommelin D J, Schellekens H, Jiskoot W (2004) Structure-immunogenicity relationships of therapeutic proteins. Pharm Res 21:897-903
26. Handbook of pharmaceutical manufacturing formulations. Volume 6. Sterile products/Sarfaraz K. Niazi, 2004.
27. J. de Haard H., van Neer N., Anneke Reurs, E. Hufton S., Roovers R., Henderikx P., de Bruïne A., Arends J.-W. and Hoogenboom H. A Large Non-immunized Human Fab Fragment Phage Library That Permits Rapid Isolation and Kinetic Analysis of High Affinity Antibodies. J Biol Chem. 1999 Jun. 25 274(26):18218-30.
28. WO 2010/001251.
29. Koch-Nolte F., Reyelt J., Schößow B., Schwarz N., Scheuplein F., Rothenburg S., Haag F., Alzogaray V., Cauerhff A. and Goldbaum F. Single domain antibodies from llama effectively and specifically block T cell ecto-ADP-ribosyltransferase ART2.2 in vivo. FASEB J., 2007 November; 21(13):3490-8.
30. Sidhu S., Lowman H., Cunningham B., Wells J. Phage display for selection of novel binding peptides. J. Methods Enzymol. 2000; 328: 333-63.
31. Marks J., Hoogenboom H., Bonnert T., McCafferty J., Griffiths A., Winter G. By-passing immunization: Human antibodies from V-gene libraries displayed on phage. J Mol Biol. 1991 Dec. 5; 222(3):581-97.
32. Vaughan T., Williams A., Pritchard K., Osbourn J., Pope A., Earnshaw J., McCafferty J., Hodits R., Wilton J. and Johnson K. Human Antibodies with Sub-nanomolar Affinities Isolated from a Large Non-immunized Phage Display Library. Nat Biotechnol. 1996 March; 14 (3): 309-14.
34. Environ Microbiol. 2006 February; 72(2):1141-7; MAbs. 2012 May-June; 4(3): 341-8.
35. Cummings M., Farnum M., and Nelen M. Universal Screening Methods and Applications of ThermoFluor®. J Biomol Screen 2006 11(7): 854-863.

The invention claimed is:

1. A method for treatment of an IL-17A-mediated disease or disorder, comprising administering to a patient in need thereof an antibody or a fragment thereof that specifically binds to human IL-17A and comprises a heavy chain variable domain $V_{HH}$, and a light chain variable domain $V_L$ comprising the amino acid sequence of SEQ ID NO: 8, wherein the $V_{HH}$ comprises:
   a) HCDR1, HCDR2 and HCDR3 comprising the amino acid sequences of SEQ ID NO: 4, SEQ ID NO: 5 and SEQ ID NO: 6, respectively; or
   b) a variant of a), comprising one amino acid substitution selected from the group consisting of:
   the amino acid at the 6th position of SEQ ID NO: 4 is N, K, R, E, W, M, Q, D, F, V, L or A;
   the amino acid at the 7th position of SEQ ID NO: 4 is S;
   the amino acid at the 8th position of SEQ ID NO: 4 is I;
   the amino acid at the 9th position of SEQ ID NO: 4 is L, A, I, S, R, V, N, Q or M;
   the amino acid at the 1st position of SEQ ID NO: 5 is G or L;
   the amino acid at the 4th position of SEQ ID NO: 5 is A;
   the amino acid at the 7th position of SEQ ID NO: 5 is S, R, P, D, I, T, E, K, A, L or W;
   the amino acid at the 3rd position of SEQ ID NO: 6 is K, S, A, T, D or G;
   the amino acid at the 4th position of SEQ ID NO: 6 is K;
   the amino acid at the 5th position of SEQ ID NO: 6 is G, Y, H, D, W or K;
   the amino acid at the 6th position of SEQ ID NO: 6 is A, V, S, L M or H;
   the amino acid at the 8th position of SEQ ID NO: 6 is E, G, A, R, V, K or Q;
   the amino acid at the 9th position of SEQ ID NO: 6 is S or N;
   the amino acid at the 10th position of SEQ ID NO: 6 is G, S, P, V, R, N or K;
   the amino acid at the 11th position of SEQ ID NO: 6 is V, M, C, T, L, Y, A, H, G or I;
   the amino acid at the 12th position of SEQ ID NO: 6 is W or S;
   the amino acid at the 13th position of SEQ ID NO: 6 is R, V, L, A, W, K, G, Q or I;
   the amino acid at the 14th position of SEQ ID NO: 6 is L, A or S; and
   the amino acid at the 15th position of SEQ ID NO: 6 is T, L, P, N, A, Q, F, I or D.

2. The method according to claim 1, wherein the HCDR1, HCDR2 and HCDR3 of the administered antibody or fragment thereof comprises the amino acid sequences of SEQ ID NO: 4, SEQ ID NO: 5 and SEQ ID NO: 6, respectively.

3. The method according to claim 1, wherein the heavy chain variable domain $V_{HH}$ of the administered antibody or fragment thereof comprises the amino acid sequence of SEQ ID NO: 7.

4. The method according to claim 1, wherein the antibody comprises a heavy chain comprising the heavy chain variable domain VHH, and the heavy chain comprises the amino acid sequence of SEQ ID NO: 9.

5. The method according to claim 1, wherein the antibody comprises a light chain comprising the light chain variable domain VL, and the light chain comprises the amino acid sequence of SEQ ID NO: 10.

6. The method according to claim 1, wherein the IL-17A-mediated disease or disorder is selected from: rheumatoid arthritis, psoriatic arthritis, spondyloarthropathy, systemic lupus erythematosus, asthma, allergic disorders, psoriasis, scleroderma, sarcoidosis, uveitis, acute respiratory distress syndrome, arthropathy, psoriatic arthropathy, pemphigus, pemphigoid, connective tissue disease associated with interstitial lung disease, ankylosing spondylitis associated with lung disease, obliterating bronchiolitis, systemic scleroderma, Sjogren's Syndrome, vitiligo, allergic contact dermatitis, lateral amyotrophic sclerosis, inflammatory response to bypass, contact dermatitis, demyelinating disease, eczema, urticaria, alopecia areata, atopic dermatitis, autoimmune dermatitis, chronic obstructive pulmonary disease (COPD), dermatomyositis, erythema multiform, keratitis, polymyositis, polymyalgia rheumatica (PMR), scleritis and ankylosing spondylitis.

7. The method according to claim 1, further comprising the administration of a TNF-α inhibitor.

8. A method for treatment of an IL-17A-mediated disease or disorder, comprising administering to a patient in need thereof an antibody or a fragment thereof that specifically binds to human IL-17A and comprises a heavy chain variable domain $V_{HH}$, and a light chain variable domain $V_L$ comprising the amino acid sequence of SEQ ID NO: 8, wherein the $V_{HH}$ comprises HCDR1, HCDR2 and HCDR3 comprising the amino acid sequences of SEQ ID NO: 4, SEQ ID NO: 5 and SEQ ID NO: 6, respectively.

9. The method according to claim 8, wherein the heavy chain variable domain $V_{HH}$ of the administered antibody or fragment thereof comprises the amino acid sequence of SEQ ID NO: 7.

10. The method according to claim 8, wherein the antibody comprises a heavy chain comprising the heavy chain variable domain VHH, and the heavy chain comprises the amino acid sequence of SEQ ID NO: 9.

11. The method according to claim 8, wherein the antibody comprises a light chain comprising the light chain variable domain VL, and the light chain comprises the amino acid sequence of SEQ ID NO: 10.

12. The method according to claim 8, wherein the IL-17A-mediated disease or disorder is selected from: rheumatoid arthritis, psoriatic arthritis, spondyloarthropathy, systemic lupus erythematosus, asthma, allergic disorders, psoriasis, scleroderma, sarcoidosis, uveitis, acute respiratory distress syndrome, arthropathy, psoriatic arthropathy, pemphigus, pemphigoid, connective tissue disease associated with interstitial lung disease, ankylosing spondylitis associated with lung disease, obliterating bronchiolitis, systemic scleroderma, Sjogren's Syndrome, vitiligo, allergic contact dermatitis, lateral amyotrophic sclerosis, inflammatory response to bypass, contact dermatitis, demyelinating disease, eczema, urticaria, alopecia areata, atopic dermatitis, autoimmune dermatitis, chronic obstructive pulmonary disease (COPD), dermatomyositis, erythema multiform, keratitis, polymyositis, polymyalgia rheumatica (PMR), scleritis and ankylosing spondylitis.

13. The method according to claim 8, further comprising the administration of a TNF-α inhibitor.

14. A method for treatment of an IL-17A-mediated disease or disorder, comprising administering to a patient in need thereof an antibody or a fragment thereof that specifically binds to human IL-17A and comprises a heavy chain variable domain $V_{HH}$ comprising the amino acid sequence of SEQ ID NO: 7, and a light chain variable domain $V_L$ comprising the amino acid sequence of SEQ ID NO: 8.

15. The method according to claim 14, wherein the antibody comprises a heavy chain comprising the heavy chain variable domain VHH, and the heavy chain comprises the amino acid sequence of SEQ ID NO: 9.

16. The method according to claim 14, wherein the antibody comprises a light chain comprising the light chain variable domain VL, and the light chain comprises the amino acid sequence of SEQ ID NO: 10.

17. The method according to claim 14, wherein the IL-17A-mediated disease or disorder is selected from: rheumatoid arthritis, psoriatic arthritis, spondyloarthropathy, systemic lupus erythematosus, asthma, allergic disorders, psoriasis, scleroderma, sarcoidosis, uveitis, acute respiratory distress syndrome, arthropathy, psoriatic arthropathy, pemphigus, pemphigoid, connective tissue disease associated with interstitial lung disease, ankylosing spondylitis associated with lung disease, obliterating bronchiolitis, systemic scleroderma, Sjogren's Syndrome, vitiligo, allergic contact dermatitis, lateral amyotrophic sclerosis, inflammatory response to bypass, contact dermatitis, demyelinating disease, eczema, urticaria, alopecia areata, atopic dermatitis, autoimmune dermatitis, chronic obstructive pulmonary disease (COPD), dermatomyositis, erythema multiform, keratitis, polymyositis, polymyalgia rheumatica (PMR), scleritis and ankylosing spondylitis.

18. The method according to claim 14, further comprising the administration of a TNF-α inhibitor.

* * * * *

SEQUENCE LISTING

<160> NUMBER OF SEQ ID NOS: 25

<210> SEQ ID NO 1
<211> LENGTH: 9
<212> TYPE: PRT
<213> ORGANISM: Lama glama
<220> FEATURE:
<223> OTHER INFORMATION: Synthesised sequence
<220> FEATURE:

```
<221> NAME/KEY: VARIANT
<222> LOCATION: (6)..(6)
<223> OTHER INFORMATION: Xaa may be Ser, Asn, Lys, Arg, Glu, Trp, Gln,
      Asp, Ala, Val or Phe
<220> FEATURE:
<221> NAME/KEY: VARIANT
<222> LOCATION: (7)..(7)
<223> OTHER INFORMATION: Xaa may be Pro or Ser
<220> FEATURE:
<221> NAME/KEY: VARIANT
<222> LOCATION: (8)..(8)
<223> OTHER INFORMATION: Xaa may be Met or Ile
<220> FEATURE:
<221> NAME/KEY: VARIANT
<222> LOCATION: (9)..(9)
<223> OTHER INFORMATION: Xaa may be Gly, Asn, Ser, Ala, Leu, Ile, Arg,
      Val or Gln

<400> SEQUENCE: 1

Gly Thr Phe Ala Thr Xaa Xaa Xaa Xaa
1               5

<210> SEQ ID NO 2
<211> LENGTH: 18
<212> TYPE: PRT
<213> ORGANISM: Lama glama
<220> FEATURE:
<223> OTHER INFORMATION: Synthesised sequence
<220> FEATURE:
<221> NAME/KEY: VARIANT
<222> LOCATION: (1)..(1)
<223> OTHER INFORMATION: Xaa may be Ala, Gly or Leu
<220> FEATURE:
<221> NAME/KEY: VARIANT
<222> LOCATION: (4)..(4)
<223> OTHER INFORMATION: Xaa may be Asp or Glu
<220> FEATURE:
<221> NAME/KEY: VARIANT
<222> LOCATION: (5)..(5)
<223> OTHER INFORMATION: Xaa may be Pro or Ala
<220> FEATURE:
<221> NAME/KEY: VARIANT
<222> LOCATION: (8)..(8)
<223> OTHER INFORMATION: Xaa may be Gly, Ser, Thr, Leu, Arg, Asp, Glu,
      Lys, Ala or Trp

<400> SEQUENCE: 2

Xaa Ile Ser Xaa Xaa Ser Gly Xaa Asp Arg Ile Tyr Ala Asp Ser Val
1               5                   10                  15

Lys Gly

<210> SEQ ID NO 3
<211> LENGTH: 19
<212> TYPE: PRT
<213> ORGANISM: Lama glama
<220> FEATURE:
<223> OTHER INFORMATION: Synthesised sequence
<220> FEATURE:
<221> NAME/KEY: VARIANT
<222> LOCATION: (3)..(3)
<223> OTHER INFORMATION: Xaa may be Lys, Ser, Thr, Val, Asp or Gly
<220> FEATURE:
<221> NAME/KEY: VARIANT
<222> LOCATION: (4)..(4)
<223> OTHER INFORMATION: Xaa may be Arg or Lys
<220> FEATURE:
<221> NAME/KEY: VARIANT
<222> LOCATION: (5)..(5)
<223> OTHER INFORMATION: Xaa may be Gly, Arg, Tyr, His, Asp, Trp or Lys
<220> FEATURE:
<221> NAME/KEY: VARIANT
<222> LOCATION: (6)..(6)
<223> OTHER INFORMATION: Xaa may be Arg, Ala, Val, Ser, Leu, or His
<220> FEATURE:
```

```
<221> NAME/KEY: VARIANT
<222> LOCATION: (8)..(8)
<223> OTHER INFORMATION: Xaa may be Asp, Glu, Gly, Ala, Arg, Val, Lys or
      Gln
<220> FEATURE:
<221> NAME/KEY: VARIANT
<222> LOCATION: (9)..(9)
<223> OTHER INFORMATION: Xaa may be Gly, Ser or Asn
<220> FEATURE:
<221> NAME/KEY: VARIANT
<222> LOCATION: (10)..(10)
<223> OTHER INFORMATION: Xaa may be Gly, Thr, Pro, Val, Arg, Asn or Lys
<220> FEATURE:
<221> NAME/KEY: VARIANT
<222> LOCATION: (11)..(11)
<223> OTHER INFORMATION: Xaa may be Val, Ser, Thr, Leu, Tyr, Ala, His,
      Gly or Ile
<220> FEATURE:
<221> NAME/KEY: VARIANT
<222> LOCATION: (12)..(12)
<223> OTHER INFORMATION: Xaa may be Tyr, Trp or Ser
<220> FEATURE:
<221> NAME/KEY: VARIANT
<222> LOCATION: (13)..(13)
<223> OTHER INFORMATION: Xaa may be Arg, Val, Leu, Tyr, Ala, Trp, Lys,
      Gly, Gln or Ile
<220> FEATURE:
<221> NAME/KEY: VARIANT
<222> LOCATION: (14)..(14)
<223> OTHER INFORMATION: Xaa may be Thr, Leu, Ala or Ser
<220> FEATURE:
<221> NAME/KEY: VARIANT
<222> LOCATION: (15)..(15)
<223> OTHER INFORMATION: Xaa may be Thr, Leu, Gly, Pro, Asn, Ala, Gln,
      Phe, Ile or Asp

<400> SEQUENCE: 3

Cys Ala Xaa Xaa Xaa Xaa Phe Xaa Xaa Xaa Xaa Xaa Xaa Xaa Xaa Asp
1               5                   10                  15

Tyr Asp Ser

<210> SEQ ID NO 4
<211> LENGTH: 9
<212> TYPE: PRT
<213> ORGANISM: Lama glama
<220> FEATURE:
<223> OTHER INFORMATION: Synthesised sequence

<400> SEQUENCE: 4

Gly Thr Phe Ala Thr Ser Pro Met Gly
1               5

<210> SEQ ID NO 5
<211> LENGTH: 17
<212> TYPE: PRT
<213> ORGANISM: Lama glama
<220> FEATURE:
<223> OTHER INFORMATION: Synthesised sequence

<400> SEQUENCE: 5

Ala Ile Ser Pro Ser Gly Gly Asp Arg Ile Tyr Ala Asp Ser Val Lys
1               5                   10                  15

Gly

<210> SEQ ID NO 6
<211> LENGTH: 19
<212> TYPE: PRT
<213> ORGANISM: Lama glama
<220> FEATURE:
<223> OTHER INFORMATION: Synthesised sequence
```

```
<400> SEQUENCE: 6

Cys Ala Val Arg Arg Phe Asp Gly Thr Ser Tyr Tyr Thr Gly Asp
1               5                   10                  15

Tyr Asp Ser

<210> SEQ ID NO 7
<211> LENGTH: 125
<212> TYPE: PRT
<213> ORGANISM: Lama glama
<220> FEATURE:
<223> OTHER INFORMATION: Synthesised sequence

<400> SEQUENCE: 7

Gln Val Gln Leu Val Gln Ser Gly Gly Gly Leu Val Gln Ala Gly
1               5                   10                  15

Ser Leu Arg Leu Ser Cys Ala Ala Ser Gly Thr Phe Ala Thr Ser
            20                  25                  30

Pro Met Gly Trp Leu Arg Gln Ala Pro Gly Lys Gly Thr Glu Phe Val
        35                  40                  45

Ala Ala Ile Ser Pro Ser Gly Gly Asp Arg Ile Tyr Ala Asp Ser Val
    50                  55                  60

Lys Gly Arg Phe Thr Ile Ser Arg Asp Asn Ala Gly Tyr Phe Ile Tyr
65                  70                  75                  80

Leu Gln Met Asn Ser Leu Lys Pro Glu Asp Thr Ala Val Tyr Tyr Cys
                85                  90                  95

Ala Val Arg Arg Arg Phe Asp Gly Thr Ser Tyr Tyr Thr Gly Asp Tyr
            100                 105                 110

Asp Ser Trp Gly Gln Gly Thr Leu Val Thr Val Ser Ser
        115                 120                 125

<210> SEQ ID NO 8
<211> LENGTH: 109
<212> TYPE: PRT
<213> ORGANISM: Homo sapiens
<220> FEATURE:
<223> OTHER INFORMATION: Synthesised sequence

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Tyr Ser Pro
                85                  90                  95

Val Thr Phe Gly Gln Gly Thr Lys Val Glu Ile Lys Arg
            100                 105

<210> SEQ ID NO 9
<211> LENGTH: 455
<212> TYPE: PRT
<213> ORGANISM: Lama glama
<220> FEATURE:
<223> OTHER INFORMATION: Synthesised sequence
```

<400> SEQUENCE: 9

Gln Val Gln Leu Val Gln Ser Gly Gly Gly Leu Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Gly Thr Glu Phe Val
        35                  40                  45

Ala Ala Ile Ser Pro Ser Gly Gly Asp Arg Ile Tyr Ala Asp Ser Val
50                  55                  60

Lys Gly Arg Phe Thr Ile Ser Arg Asp Asn Ala Gly Tyr Phe Ile Tyr
65                  70                  75                  80

Leu Gln Met Asn Ser Leu Lys Pro Glu Asp Thr Ala Val Tyr Tyr Cys
                85                  90                  95

Ala Val Arg Arg Arg Phe Asp Gly Thr Ser Tyr Tyr Thr Gly Asp Tyr
            100                 105                 110

Asp Ser Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Tyr Ile Thr Arg Glu Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser

```
                    405                 410                 415
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 10
<211> LENGTH: 215
<212> TYPE: PRT
<213> ORGANISM: Homo sapiens
<220> FEATURE:
<223> OTHER INFORMATION: Synthesised sequence

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Tyr Ser Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 11
<211> LENGTH: 120
<212> TYPE: PRT
<213> ORGANISM: Lama glama
<220> FEATURE:
<223> OTHER INFORMATION: 1VHH

<400> SEQUENCE: 11

Gln Val Gln Leu Gln Gln Ser Gly Gly Gly Ser Val Gln Thr Gly Gly
1               5                   10                  15

Ser Leu Thr Leu Thr Cys Ala Ala Ser Gly Leu Thr Phe Glu Ala Asn
            20                  25                  30
```

```
Ser Leu Gly Trp Phe Arg Gln Ser Pro Gly Lys Glu Arg Glu Phe Val
            35                  40                  45

Ala Ala Val Ser Phe Thr Lys Arg Ile Asp Tyr Ala Asp Ser Val Lys
 50                  55                  60

Gly Arg Phe Phe Ile Ser Arg Asp Asn Thr Met Asn Thr Val Tyr Leu
 65                  70                  75                  80

Gln Met Asn Ser Leu Lys Pro Glu Asp Thr Gly Ile Tyr Thr Cys Ala
                 85                  90                  95

Ala Asp Pro Leu Leu Ile Ser Asn Lys Arg Ala Asn Ile Trp Gly Gln
            100                 105                 110

Gly Thr Met Val Thr Val Ser Ser
            115                 120
```

<210> SEQ ID NO 12
<211> LENGTH: 113
<212> TYPE: PRT
<213> ORGANISM: Lama glama
<220> FEATURE:
<223> OTHER INFORMATION: 2VHH

<400> SEQUENCE: 12

```
Gln Val Gln Leu Val Gln Ser Gly Gly Gly Leu Val Gln Pro Gly Gly
 1               5                  10                  15

Ser Leu Arg Leu Ser Cys Ala Ala Ser Pro Arg Val Ile Ser Ile His
            20                  25                  30

Asp Met Ala Trp Tyr Arg Gln Ala Pro Gly Lys Glu Arg Glu Leu Val
            35                  40                  45

Ala Gly Ile Thr Thr Arg Gly Ile Thr Asp Tyr Gly Tyr Ser Val Lys
 50                  55                  60

Gly Arg Phe Thr Ile Ser Arg Asp Asp Ala Lys Asn Thr Leu Phe Leu
 65                  70                  75                  80

Gln Met Asn Asp Leu Lys Pro Glu Asp Thr Ala Val Tyr Tyr Cys Asn
                 85                  90                  95

Leu Arg His Tyr Glu Val Trp Gly Gln Gly Thr Leu Val Thr Val Ser
            100                 105                 110

Ser
```

<210> SEQ ID NO 13
<211> LENGTH: 125
<212> TYPE: PRT
<213> ORGANISM: Lama glama
<220> FEATURE:
<223> OTHER INFORMATION: 3VHH

<400> SEQUENCE: 13

```
Gln Val Gln Leu Gln Gln Ser Gly Gly Gly Ser Val Gln Ala Gly Gly
 1               5                  10                  15

Ser Leu Arg Leu Ser Cys Ala Ala Ser Gly Gly Thr Phe Ala Thr Ser
            20                  25                  30

Pro Met Gly Trp Phe Arg Gln Ala Pro Gly Lys Glu Arg Glu Gly Val
            35                  40                  45

Ala Ala Ile Ser Pro Ser Gly Gly Asp Arg Ile Tyr Asp Asp Ser Val
 50                  55                  60

Lys Gly Arg Phe Thr Ile Ser Arg Asp Asn Ala Gly Tyr Phe Ile Tyr
 65                  70                  75                  80

Leu Gln Met Asn Ser Leu Lys Pro Glu Asp Thr Ala Arg Tyr Tyr Cys
                 85                  90                  95
```

-continued

Ala Val Arg Arg Arg Phe Asp Gly Thr Ser Tyr Tyr Thr Gly Asp Tyr
              100                 105                 110

Asp Ser Trp Gly Gln Gly Thr Leu Val Thr Val Ser Ser
        115                 120                 125

<210> SEQ ID NO 14
<211> LENGTH: 113
<212> TYPE: PRT
<213> ORGANISM: Lama glama
<220> FEATURE:
<223> OTHER INFORMATION: VK4B11

<400> SEQUENCE: 14

Asp Val Val Met Thr Gln Ser Pro Ser Ser Val Thr Ala Ser Ala Gly
1               5                   10                  15

Glu Thr Val Thr Ile Asn Cys Lys Ser Gln Ser Val Ala Tyr Lys
            20                  25                  30

Ser Asn Gln Lys Asn Tyr Leu Ala Trp Tyr Gln Gln Arg Pro Gly Gln
        35                  40                  45

Ser Pro Arg Leu Leu Ile Tyr Tyr Ala Ser Thr Arg Thr Ser Gly Val
    50                  55                  60

Pro Asp Arg Phe Ser Gly Ser Gly Ser Thr Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Tyr Ser Ala Pro Tyr Ser Phe Gly Ser Gly Thr Lys Leu Glu Ile
            100                 105                 110

Lys

<210> SEQ ID NO 15
<211> LENGTH: 111
<212> TYPE: PRT
<213> ORGANISM: Lama glama
<220> FEATURE:
<223> OTHER INFORMATION: VLB5

<400> SEQUENCE: 15

Ala Val Leu Thr Gln Leu Ser Ser Met Ser Gly Ser Pro Gly Gln Thr
1               5                   10                  15

Val Thr Ile Thr Cys Thr Gly Ser Ile Thr Asn Ile Gly Gln Tyr Arg
            20                  25                  30

Val Asn Trp Tyr Gln His Leu Pro Gly Thr Ala Pro Lys Leu Leu Ile
        35                  40                  45

Tyr Ser Asn Ala Asn Arg Val Ser Gly Val Pro Asp Arg Phe Ser Gly
    50                  55                  60

Ser Lys Ser Gly Ser Thr Ala Ser Leu Thr Ile Ala Gly Val Gln Ala
65                  70                  75                  80

Glu Asp Glu Ala Asp Tyr Tyr Cys Ser Ala Trp Asp Gly Ser Leu Asn
                85                  90                  95

Gly Tyr Val Phe Gly Gly Gly Thr Lys Val Thr Val Leu Gln Arg
            100                 105                 110

<210> SEQ ID NO 16
<211> LENGTH: 112
<212> TYPE: PRT
<213> ORGANISM: Lama glama
<220> FEATURE:
<223> OTHER INFORMATION: VLF4

<400> SEQUENCE: 16

```
Gln Ala Val Leu Thr Gln Pro Pro Ser Val Ser Gly Ser Pro Gly Gln
1               5                   10                  15

Thr Val Thr Ile Ser Cys Thr Gly Thr Ser Asp Asp Val Gly Ser Gly
            20                  25                  30

Asn Tyr Val Ser Trp Tyr Gln Gln Val Pro Gly Met Ala Pro Lys Leu
        35                  40                  45

Leu Ile Tyr Asn Ala Gly Thr Arg Arg Ala Gly Ile Thr Gly Arg Phe
    50                  55                  60

Ser Ala Ser Lys Ser Gly Asn Thr Ala Ser Leu Thr Ile Ser Gly Leu
65              70                  75                  80

Gln Ser Glu Asp Glu Ala Asp Tyr Tyr Cys Ala Ser Tyr Arg Lys Ile
                85                  90                  95

Asn Lys Tyr Val Phe Gly Gly Gly Thr Lys Leu Thr Val Leu Gln Arg
            100                 105                 110
```

<210> SEQ ID NO 17
<211> LENGTH: 125
<212> TYPE: PRT
<213> ORGANISM: Lama glama
<220> FEATURE:
<223> OTHER INFORMATION: Wild 3VHHFab

<400> SEQUENCE: 17

```
Gln Val Gln Leu Gln Gln Ser Gly Gly Gly Ser Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Glu Arg Glu Phe Val
        35                  40                  45

Ala Ala Ile Ser Pro Ser Gly Gly Asp Arg Ile Tyr Asp Asp Ser Val
    50                  55                  60

Lys Gly Arg Phe Thr Ile Ser Arg Asp Asn Ala Gly Tyr Phe Ile Tyr
65              70                  75                  80

Leu Gln Met Asn Ser Leu Lys Pro Glu Asp Thr Ala Arg Tyr Tyr Cys
                85                  90                  95

Ala Val Arg Arg Arg Phe Asp Gly Thr Ser Tyr Tyr Thr Gly Asp Tyr
            100                 105                 110

Asp Ser Trp Gly Gln Gly Thr Leu Val Thr Val Ser Ser
            115                 120                 125
```

<210> SEQ ID NO 18
<211> LENGTH: 125
<212> TYPE: PRT
<213> ORGANISM: Lama glama
<220> FEATURE:
<223> OTHER INFORMATION: mut1

<400> SEQUENCE: 18

```
Gln Val Gln Leu Gln Gln Ser Gly Gly Gly Ser Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Gly Leu Glu Phe Val
        35                  40                  45

Ala Ala Ile Ser Pro Ser Gly Gly Asp Arg Ile Tyr Ala Asp Ser Val
    50                  55                  60

Lys Gly Arg Phe Thr Ile Ser Arg Asp Asn Ala Gly Tyr Phe Ile Tyr
```

```
                65                  70                  75                  80
Leu Gln Met Asn Ser Leu Lys Pro Glu Asp Thr Ala Arg Tyr Tyr Cys
                    85                  90                  95

Ala Val Arg Arg Arg Phe Asp Gly Thr Ser Tyr Tyr Thr Gly Asp Tyr
                100                 105                 110

Asp Ser Trp Gly Gln Gly Thr Leu Val Thr Val Ser Ser
            115                 120                 125
```

```
<210> SEQ ID NO 19
<211> LENGTH: 125
<212> TYPE: PRT
<213> ORGANISM: Lama glama
<220> FEATURE:
<223> OTHER INFORMATION: mut2

<400> SEQUENCE: 19

Gln Val Gln Leu Gln Gln Ser Gly Gly Gly Leu Val Gln Ala Gly Gly
1               5                   10                  15

Ser Leu Arg Leu Ser Cys Ala Ala Ser Gly Gly Thr Phe Ala Thr Ser
                20                  25                  30

Pro Met Gly Trp Leu Arg Gln Ala Pro Gly Lys Gly Arg Glu Trp Val
            35                  40                  45

Ala Ala Ile Ser Pro Ser Gly Gly Asp Arg Ile Tyr Ala Asp Ser Val
        50                  55                  60

Lys Gly Arg Phe Thr Ile Ser Arg Asp Asn Ala Gly Tyr Phe Ile Tyr
65                  70                  75                  80

Leu Gln Met Asn Ser Leu Lys Pro Glu Asp Thr Ala Arg Tyr Tyr Cys
                85                  90                  95

Ala Val Arg Arg Arg Phe Asp Gly Thr Ser Tyr Tyr Thr Gly Asp Tyr
                100                 105                 110

Asp Ser Trp Gly Gln Gly Thr Leu Val Thr Val Ser Ser
            115                 120                 125
```

```
<210> SEQ ID NO 20
<211> LENGTH: 125
<212> TYPE: PRT
<213> ORGANISM: Lama glama
<220> FEATURE:
<223> OTHER INFORMATION: mut3

<400> SEQUENCE: 20

Gln Val Gln Leu Gln Gln Ser Gly Gly Gly Ser Val Gln Ala Gly Gly
1               5                   10                  15

Ser Leu Arg Leu Ser Cys Ala Ala Ser Gly Gly Thr Phe Ala Thr Ser
                20                  25                  30

Pro Met Gly Trp Leu Arg Gln Ala Pro Gly Lys Glu Leu Glu Phe Val
            35                  40                  45

Ala Ala Ile Ser Pro Ser Gly Gly Asp Arg Ile Tyr Ala Asp Ser Val
        50                  55                  60

Lys Gly Arg Phe Thr Ile Ser Arg Asp Asn Ala Gly Tyr Phe Ile Tyr
65                  70                  75                  80

Leu Gln Met Asn Ser Leu Lys Pro Glu Asp Thr Ala Arg Tyr Tyr Cys
                85                  90                  95

Ala Val Arg Arg Arg Phe Asp Gly Thr Ser Tyr Tyr Thr Gly Asp Tyr
                100                 105                 110

Asp Ser Trp Gly Gln Gly Thr Leu Val Thr Val Ser Ser
            115                 120                 125
```

<210> SEQ ID NO 21
<211> LENGTH: 125
<212> TYPE: PRT
<213> ORGANISM: Lama glama
<220> FEATURE:
<223> OTHER INFORMATION: mut4

<400> SEQUENCE: 21

Gln Val Gln Leu Gln Gln Ser Gly Gly Gly Leu Val Gln Ala Gly Gly
1               5                   10                  15

Ser Leu Arg Leu Ser Cys Ala Ala Ser Gly Gly Thr Phe Ala Thr Ser
            20                  25                  30

Pro Met Gly Trp Leu Arg Gln Ala Pro Gly Lys Gly Arg Glu Phe Val
        35                  40                  45

Ala Ala Ile Ser Pro Ser Gly Gly Asp Arg Ile Tyr Ala Asp Ser Val
    50                  55                  60

Lys Gly Arg Phe Thr Ile Ser Arg Asp Asn Ala Gly Tyr Phe Ile Tyr
65                  70                  75                  80

Leu Gln Met Asn Ser Leu Lys Pro Glu Asp Thr Ala Arg Tyr Tyr Cys
                85                  90                  95

Ala Val Arg Arg Phe Asp Gly Thr Ser Tyr Tyr Thr Gly Asp Tyr
            100                 105                 110

Asp Ser Trp Gly Gln Gly Thr Leu Val Thr Val Ser Ser
        115                 120                 125

<210> SEQ ID NO 22
<211> LENGTH: 107
<212> TYPE: PRT
<213> ORGANISM: Lama glama
<220> FEATURE:
<223> OTHER INFORMATION: VK1A7

<400> SEQUENCE: 22

Glu Ile Val Leu Thr Gln Ser Pro Ala Ser Leu Ser Ala Ser Val Gly
1               5                   10                  15

Asp Arg Val Asp Ile Thr Cys Gln Ala Ser Gln Ser Ile Asn Asn Lys
            20                  25                  30

Ile Ala Trp Tyr Gln Gln Lys Pro Gly Lys Pro Lys Val Leu Ile
        35                  40                  45

Tyr Ala Ala Ser Lys Leu Pro Thr Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Thr Tyr Tyr Cys Leu Gln Asp Tyr Asn Trp Pro Trp
                85                  90                  95

Thr Phe Gly Ala Gly Thr Lys Leu Glu Ile Lys
            100                 105

<210> SEQ ID NO 23
<211> LENGTH: 108
<212> TYPE: PRT
<213> ORGANISM: Lama glama
<220> FEATURE:
<223> OTHER INFORMATION: VK3cl8

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser

```
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Tyr Ser Pro
                85                  90                  95

Val Thr Phe Gly Gln Gly Thr Lys Val Glu Ile Lys
                100                 105

<210> SEQ ID NO 24
<211> LENGTH: 108
<212> TYPE: PRT
<213> ORGANISM: Lama glama
<220> FEATURE:
<223> OTHER INFORMATION: VK3cl18

<400> SEQUENCE: 24

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ser Tyr Tyr Tyr Pro
                85                  90                  95

Val Thr Phe Gly Gln Gly Thr Lys Val Glu Ile Lys
                100                 105

<210> SEQ ID NO 25
<211> LENGTH: 113
<212> TYPE: PRT
<213> ORGANISM: Lama glama
<220> FEATURE:
<223> OTHER INFORMATION: VK4E12

<400> SEQUENCE: 25

Asp Ile Gln Leu Thr Gln Ser Pro Ser Ser Leu Ser Ala Ser Ala Gly
 1               5                  10                  15

Glu Thr Ala Ser Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80
```

```
Ile Ser Ser Leu Gln Ser Glu Asp Ala Ala Val Tyr Tyr Cys Gln Gln
                85              90                  95

Gly Tyr Ser Thr Pro His Thr Phe Gly Gln Gly Thr Lys Val Glu Ile
            100             105                 110

Lys
```